US012721624B2

(12) United States Patent
Mozloom, Jr. et al.

(10) Patent No.: US 12,721,624 B2
(45) Date of Patent: Sep. 1, 2026

(54) SURGICAL STAPLER WITH FIRING LOCKOUT FEATURE COUPLED TO END EFFECTOR RETAINER

(71) Applicant: Cilag GmbH International, Zug (CH)

(72) Inventors: Joseph T. Mozloom, Jr., Cincinnati, OH (US); William C. Ryle, Covington, KY (US); Douglas Marriott, Maineville, OH (US); Joseph R. Lawrence, San Diego, CA (US); Ioannis Girousis, San Diego, CA (US); Sebastian C. Beck, San Diego, CA (US); Michael D. Auld, Milford, OH (US); Mark T. Larson, Cincinnati, OH (US); Jason T. Clement, Roseville, MN (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/650,836

(22) Filed: Apr. 30, 2024

(65) Prior Publication Data

US 2025/0331851 A1 Oct. 30, 2025

(51) Int. Cl.
*A61B 17/064* (2006.01)
*A61B 17/072* (2006.01)
(Continued)

(52) U.S. Cl.
CPC ...... *A61B 17/072* (2013.01); *A61B 17/07207* (2013.01); *A61B 90/03* (2016.02); (Continued)

(58) Field of Classification Search
CPC ........ A61B 17/072; A61B 2017/00075; A61B 2017/07257; A61B 2017/07271; A61B 2017/07278; A61B 2017/07285
See application file for complete search history.

(56) References Cited

U.S. PATENT DOCUMENTS 5,129,570 A 7/1992 Schulze et al.
5,465,895 A 11/1995 Knodel et al.
(Continued)

FOREIGN PATENT DOCUMENTS

CN 202982103 U 6/2013
CN 103860222 A 6/2014
(Continued)

OTHER PUBLICATIONS

U.S. Appl. No. 18/650,562; and U.S. Appl. No. 18/650,653.
(Continued)

*Primary Examiner* — Eyamindae C Jallow
(74) *Attorney, Agent, or Firm* — FBT Gibbons LLP

(57) ABSTRACT

An apparatus includes a body (700), a shaft (600A), an end effector (200), and a lockout assembly (1100). The end effector includes a cartridge jaw (202), an anvil jaw (204), a knife (206) and a distal retainer (1110). The lockout assembly includes a sensor (1120) and a lockout (1140). The lockout is vertically constrained. The sensor is associated with a first pivot (1124) and a second pivot. The first pivot is grounded with respect to a channel (1114). The second pivot is a moving pivot. The lockout assembly includes an unlocked and locked position. The second pivot is positioned above the first pivot when the lockout assembly is in the unlocked position with the lockout providing no interference with respect to actuation of the knife. The first pivot and the second pivot are positioned at substantially the same height when the lockout assembly is in the locked position.

20 Claims, 40 Drawing Sheets

(51) Int. Cl.
*A61B 90/00* (2016.01)
*A61B 17/00* (2006.01)

(52) U.S. Cl.
CPC ............... *A61B 2017/00022* (2013.01); *A61B 2017/00075* (2013.01); *A61B 2017/07257* (2013.01); *A61B 2017/07271* (2013.01); *A61B 2017/07278* (2013.01); *A61B 2017/07285* (2013.01); *A61B 2090/034* (2016.02)

(56) References Cited

U.S. PATENT DOCUMENTS

| | | | |
|---|---|---|---|
| 6,988,649 | B2 | 1/2006 | Shelton, IV et al. |
| 7,380,695 | B2 | 6/2008 | Doll et al. |
| 7,380,696 | B2 | 6/2008 | Shelton, IV et al. |
| 7,404,508 | B2 | 7/2008 | Smith et al. |
| 7,434,715 | B2 | 10/2008 | Shelton, IV et al. |
| 7,721,930 | B2 | 5/2010 | McKenna et al. |
| 7,810,692 | B2 | 10/2010 | Hall et al. |
| 7,832,408 | B2 | 11/2010 | Shelton, IV et al. |
| 7,845,537 | B2 | 12/2010 | Shelton, IV et al. |
| 8,083,120 | B2 | 12/2011 | Shelton, IV et al. |
| 8,210,411 | B2 | 7/2012 | Yates et al. |
| 8,408,439 | B2 | 4/2013 | Huang et al. |
| 8,453,914 | B2 | 6/2013 | Laurent et al. |
| 8,708,213 | B2 | 4/2014 | Shelton, IV et al. |
| 9,060,770 | B2 | 6/2015 | Shelton, IV et al. |
| 9,186,142 | B2 | 11/2015 | Fanelli et al. |
| 9,517,065 | B2 | 12/2016 | Simms et al. |
| 9,526,499 | B2 | 12/2016 | Kostrzewski et al. |
| 9,622,746 | B2 | 4/2017 | Simms et al. |
| 9,717,497 | B2 | 8/2017 | Zerkle et al. |
| 9,717,498 | B2 | 8/2017 | Aranyi et al. |
| 9,757,126 | B2 | 9/2017 | Cappola |
| 9,795,379 | B2 | 10/2017 | Leimbach et al. |
| 9,808,248 | B2 | 11/2017 | Hoffman |
| 9,839,487 | B2 | 12/2017 | Dachs, II |
| 10,011,018 | B2 | 7/2018 | McGrogan et al. |
| 10,092,292 | B2 | 10/2018 | Boudreaux et al. |
| 10,175,127 | B2 | 1/2019 | Collins et al. |
| 10,182,815 | B2 | 1/2019 | Williams et al. |
| 10,245,036 | B1 | 4/2019 | Schaller |
| 10,303,641 | B2 | 5/2019 | Collins et al. |
| 10,307,170 | B2 | 6/2019 | Parfett et al. |
| 10,314,577 | B2 | 6/2019 | Laurent et al. |
| 10,335,147 | B2 | 7/2019 | Rector et al. |
| 10,485,621 | B2 | 11/2019 | Morrissette et al. |
| 10,492,785 | B2 | 12/2019 | Overmyer et al. |
| 10,517,595 | B2 | 12/2019 | Hunter et al. |
| 10,537,400 | B2 | 1/2020 | Dachs, II et al. |
| 10,588,633 | B2 | 3/2020 | Shelton, IV et al. |
| 10,610,313 | B2 | 4/2020 | Bailey et al. |
| 10,667,809 | B2 | 6/2020 | Bakos et al. |
| 10,695,057 | B2 | 6/2020 | Shelton, IV et al. |
| 10,806,530 | B2 | 10/2020 | Liao et al. |
| 10,835,245 | B2 | 11/2020 | Swayze et al. |
| 10,863,988 | B2 | 12/2020 | Patel et al. |
| 10,959,726 | B2 | 3/2021 | Williams et al. |
| 11,020,138 | B2 | 6/2021 | Ragosta |
| 11,026,755 | B2 | 6/2021 | Weir et al. |
| 11,076,926 | B2 | 8/2021 | Ragosta et al. |
| 11,147,552 | B2 | 10/2021 | Burbank et al. |
| 11,166,773 | B2 | 11/2021 | Ragosta et al. |
| 11,197,668 | B2 | 12/2021 | Shelton, IV et al. |
| 11,234,700 | B2 | 2/2022 | Ragosta et al. |
| 11,259,884 | B2 | 3/2022 | Burbank |
| 11,311,293 | B2 | 4/2022 | Roberts et al. |
| 11,317,917 | B2* | 5/2022 | Shelton, IV ......... A61B 17/072 |
| 11,439,390 | B2 | 9/2022 | Patel et al. |
| 11,452,524 | B2 | 9/2022 | Chavan et al. |
| 11,478,242 | B2 | 10/2022 | Shelton, IV et al. |
| 11,504,124 | B2 | 11/2022 | Patel et al. |
| 11,529,140 | B2 | 12/2022 | Shelton, IV et al. |
| 11,540,826 | B2 | 1/2023 | Nalagatla et al. |
| 11,717,287 | B2 | 8/2023 | Williams et al. |
| 11,779,332 | B2 | 10/2023 | Shelton, IV et al. |
| 11,864,762 | B2 | 1/2024 | Wixey |
| 11,944,297 | B2 | 4/2024 | Shelton, IV et al. |
| 11,957,336 | B2 | 4/2024 | Shelton, IV et al. |
| 11,974,741 | B2 | 5/2024 | Moubarak et al. |
| 11,986,182 | B2 | 5/2024 | Shelton, IV et al. |
| 11,986,184 | B2 | 5/2024 | Patel et al. |
| 12,089,844 | B2 | 9/2024 | Patel et al. |
| 2004/0232200 | A1 | 11/2004 | Shelton, IV et al. |
| 2006/0185682 | A1 | 8/2006 | Marczyk |
| 2007/0102475 | A1 | 5/2007 | Ortiz et al. |
| 2010/0065604 | A1 | 3/2010 | Weng |
| 2010/0301095 | A1 | 12/2010 | Shelton, IV et al. |
| 2012/0209314 | A1 | 8/2012 | Weir et al. |
| 2013/0327808 | A1 | 12/2013 | Chen et al. |
| 2014/0224686 | A1 | 8/2014 | Aronhalt et al. |
| 2014/0263550 | A1 | 9/2014 | Aranyi et al. |
| 2015/0265275 | A1 | 9/2015 | Chen et al. |
| 2015/0272576 | A1 | 10/2015 | Cappola |
| 2015/0297228 | A1 | 10/2015 | Huitema et al. |
| 2015/0316431 | A1 | 11/2015 | Collins et al. |
| 2015/0374363 | A1 | 12/2015 | Laurent, IV et al. |
| 2016/0157863 | A1 | 6/2016 | Williams et al. |
| 2016/0361126 | A1 | 12/2016 | Schena et al. |
| 2017/0020617 | A1 | 1/2017 | Weir et al. |
| 2017/0265865 | A1 | 9/2017 | Burbank |
| 2017/0265954 | A1 | 9/2017 | Burbank et al. |
| 2017/0290584 | A1 | 10/2017 | Jasemian et al. |
| 2017/0296172 | A1* | 10/2017 | Harris .................. A61B 17/072 |
| 2017/0296190 | A1 | 10/2017 | Aronhalt et al. |
| 2017/0333037 | A1 | 11/2017 | Wellman et al. |
| 2018/0126504 | A1* | 5/2018 | Shelton, IV ........... A61B 90/08 |
| 2018/0168651 | A1 | 6/2018 | Shelton, IV et al. |
| 2018/0168756 | A1 | 6/2018 | Liao et al. |
| 2018/0271608 | A1 | 9/2018 | Ragosta et al. |
| 2018/0310935 | A1 | 11/2018 | Wixey |
| 2018/0325606 | A1 | 11/2018 | Weir et al. |
| 2018/0344419 | A1 | 12/2018 | Dachs, II et al. |
| 2019/0008509 | A1* | 1/2019 | Shelton, IV ..... A61B 17/07207 |
| 2019/0038371 | A1 | 2/2019 | Wixey et al. |
| 2019/0076142 | A1 | 3/2019 | Wixey |
| 2019/0076143 | A1 | 3/2019 | Smith |
| 2019/0099181 | A1 | 4/2019 | Shelton, IV et al. |
| 2019/0167266 | A1 | 6/2019 | Patel et al. |
| 2019/0183503 | A1 | 6/2019 | Shelton, IV et al. |
| 2019/0192158 | A1 | 6/2019 | Scott et al. |
| 2019/0200989 | A1 | 7/2019 | Burbank et al. |
| 2019/0239967 | A1 | 8/2019 | Ragosta et al. |
| 2019/0261984 | A1* | 8/2019 | Nelson ............. A61B 17/07207 |
| 2019/0262088 | A1 | 8/2019 | Burbank |
| 2020/0138529 | A1 | 5/2020 | Ragosta et al. |
| 2020/0268381 | A1 | 8/2020 | Roberts et al. |
| 2020/0397430 | A1 | 12/2020 | Patel et al. |
| 2020/0405301 | A1 | 12/2020 | Shelton, IV et al. |
| 2021/0330322 | A1 | 10/2021 | Laurent et al. |
| 2021/0378669 | A1 | 12/2021 | Shelton, IV et al. |
| 2021/0393340 | A1 | 12/2021 | Beckman et al. |
| 2021/0401433 | A1 | 12/2021 | Freidel et al. |
| 2022/0133318 | A1 | 5/2022 | Hudson et al. |
| 2022/0211370 | A1 | 7/2022 | Roberts et al. |
| 2023/0045998 | A1 | 2/2023 | Shelton, IV et al. |
| 2023/0049736 | A1 | 2/2023 | Shelton, IV et al. |
| 2023/0050358 | A1 | 2/2023 | Shelton, IV et al. |
| 2023/0050707 | A1 | 2/2023 | Shelton, IV et al. |
| 2023/0051222 | A1 | 2/2023 | Shelton, IV et al. |
| 2023/0051271 | A1 | 2/2023 | Shelton, IV et al. |
| 2023/0051361 | A1 | 2/2023 | Shelton, IV et al. |
| 2023/0051938 | A1 | 2/2023 | Shelton, IV et al. |
| 2023/0052307 | A1 | 2/2023 | Shelton, IV et al. |
| 2023/0121131 | A1 | 4/2023 | Swayze et al. |
| 2024/0065690 | A1 | 2/2024 | Jasemian et al. |
| 2024/0197317 | A1 | 6/2024 | Moubarak et al. |

FOREIGN PATENT DOCUMENTS

| | | | |
|---|---|---|---|
| EP | 3498191 | A2 | 6/2019 |
| WO | WO 2015/153642 | A1 | 10/2015 |
| WO | WO 2017/083125 | A1 | 5/2017 |
| WO | WO 2017/083129 | A1 | 5/2017 |

(56) References Cited

FOREIGN PATENT DOCUMENTS

| | | |
|---|---|---|
| WO | WO 2018/049198 A1 | 3/2018 |
| WO | WO 2018/049206 A1 | 3/2018 |
| WO | WO 2018/049211 A1 | 3/2018 |
| WO | WO 2018/049217 A1 | 3/2018 |
| WO | WO 2018/052806 A1 | 3/2018 |
| WO | WO 2018/052810 A1 | 3/2018 |
| WO | WO 2018/071497 A1 | 4/2018 |
| WO | WO 2018/071763 A1 | 4/2018 |
| WO | WO 2018/085529 A2 | 5/2018 |
| WO | WO 2018/175467 A1 | 9/2018 |
| WO | WO 2019/165403 A1 | 8/2019 |
| WO | WO 2020/131290 A1 | 6/2020 |

OTHER PUBLICATIONS

U.S. Appl. No. 18/588,094, entitled "Incompatible Staple Cartridge Use Prevention Features for Surgical Stapler," filed Feb. 27, 2024.

U.S. Appl. No. 18/588,684, entitled "Method of Surgical Stapling," filed Feb. 27, 2024.

U.S. Appl. No. 18/650,562, entitled "Surgical Stapler with Firing Lockout Feature Coupled to End Effector Knife," filed Apr. 30, 2024.

U.S. Appl. No. 18/650,653, entitled "Surgical Stapler with Firing Lockout Feature Coupled to End Effector Jaw," filed Apr. 30, 2024.

European Search Report and Written Opinion dated Feb. 14, 2024, for Application No. 23196507.0, 12 pages.

International Search Report and Written Opinion dated Jan. 23, 2023, for International Application No. PCT/IB2022/057609, 15 pages.

U.S. Appl. No. 18/883,569, entitled "Surgical Stapler with Rotatable Lockout Collar," filed Sep. 12, 2024.

U.S. Appl. No. 19/029,025, entitled "Surgical Tool Comprising a Firing Beam with an Arm," filed Jan. 17, 2025.

U.S. Appl. No. 19/188,629, entitled "Firing Beam Head Having a Rotatable Lock," filed Apr. 24, 2025.

* cited by examiner

SURGICAL STAPLER WITH FIRING LOCKOUT FEATURE COUPLED TO END EFFECTOR RETAINER

BACKGROUND

In some settings, endoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion that is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

The surgical stapling features of the present disclosure seek to inhibit firing of a surgical stapler end effector when the end effector is loaded with a spent staple cartridge that has already been fired, and/or when a staple cartridge is entirely absent from the end effector. Specifically, such features of the present disclosure place the end effector in a lockout state that inhibits firing in either of such scenario. While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate examples of the invention, and, together with the general description of the invention given above, and the detailed description of the examples given below, serve to explain the principles of the present invention.

DETAILED DESCRIPTION

Figure 1:
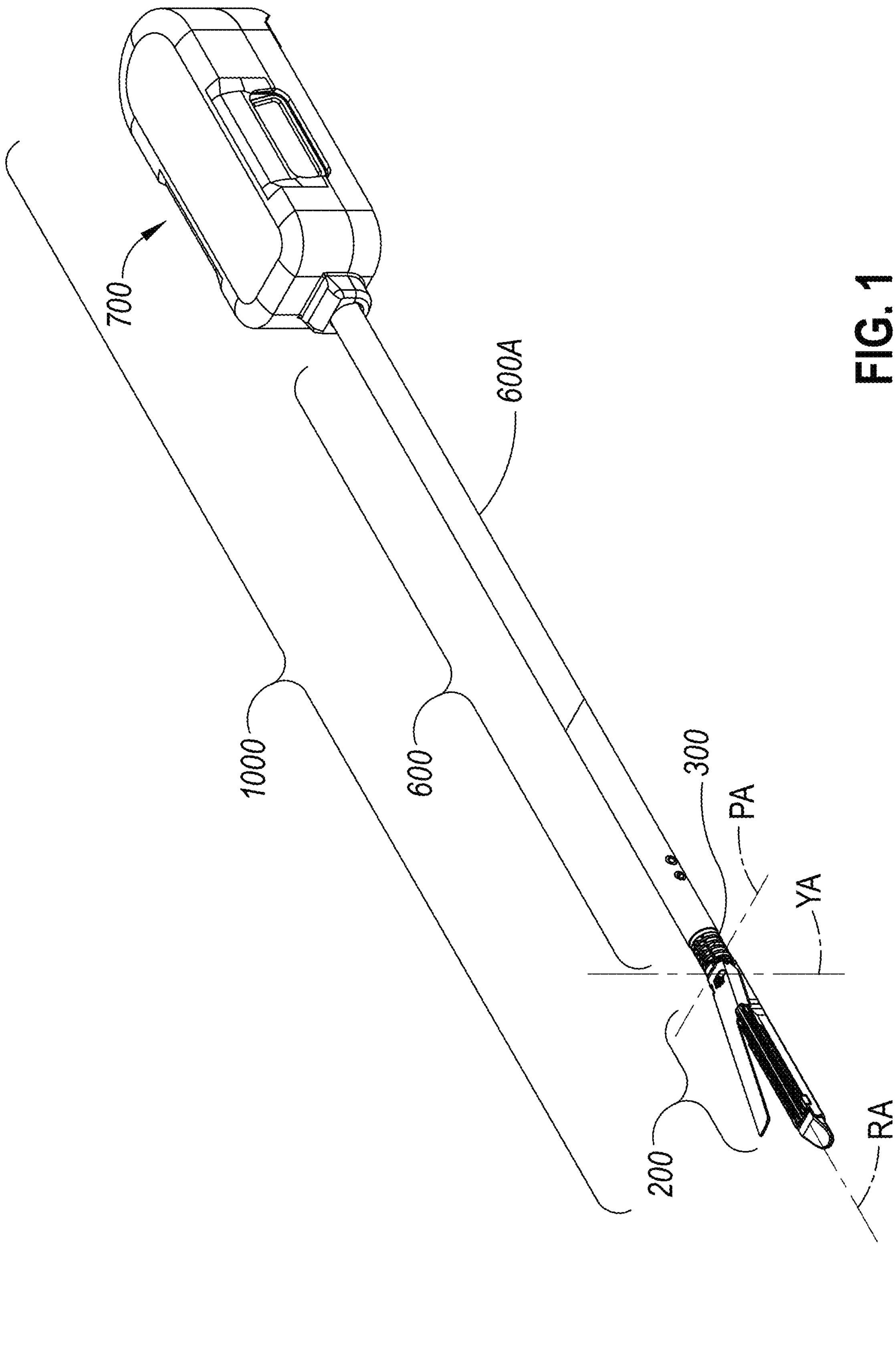
FIG. 1 is a perspective view of an illustrative surgical instrument having a housing, a shaft assembly, an articulation joint, and an end effector.

The following detailed description should be read with reference to the drawings, in which like elements in different drawings are identically numbered. The drawings, which are not necessarily to scale, depict selected versions and are not intended to limit the scope of the invention. The detailed description illustrates by way of example, not by way of limitation, the principles of the invention. This description will clearly enable one skilled in the art to make and use the invention, and describes several versions, adaptations, variations, alternatives and uses of the invention, including what is presently believed to be the best mode of carrying out the invention.

Numerous specific details are set forth to provide a thorough understanding of the overall structure, function, manufacture, and use of the versions as described in the specification and illustrated in the accompanying drawings. Well-known operations, components, and elements have not been described in detail so as not to obscure the versions described in the specification. The reader will understand that the versions described and illustrated herein are non-limiting examples, and thus it can be appreciated that the specific structural and functional details disclosed herein may be representative and illustrative. Variations and changes thereto may be made without departing from the scope of the claims.

The terms “comprise” (and any form of comprise, such as “comprises” and “comprising”), “have” (and any form of have, such as “has” and “having”), “include” (and any form of include, such as “includes” and “including”) and “contain” (and any form of contain, such as “contains” and “containing”) are open-ended linking verbs. As a result, a surgical system, device, or apparatus that “comprises,” “has,” “includes” or “contains” one or more elements possesses those one or more elements, but is not limited to possessing only those one or more elements. Likewise, an element of a system, device, or apparatus that “comprises,” “has,” “includes” or “contains” one or more features possesses those one or more features, but is not limited to possessing only those one or more features.

The terms “proximal” and “distal” are used herein with reference to a robotic platform manipulating the housing portion of the surgical instrument. The term “proximal” refers to the portion closest to the robotic platform and the term “distal” refers to the portion located away from the robotic platform. It will be further appreciated that, for convenience and clarity, spatial terms such as “vertical”, “horizontal”, “up”, and “down” may be used herein with respect to the drawings. However, surgical instruments are used in many orientations and positions, and these terms are not intended to be limiting and/or absolute.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures, and "substantially equal" values encompass nominally equal values.

Furthermore, the use of "couple", "coupled", or similar phrases should not be construed as being limited to a certain number of components or a particular order of components unless the context clearly dictates otherwise.

I. OVERVIEW OF ILLUSTRATIVE SURGICAL INSTRUMENT

Figure 2:
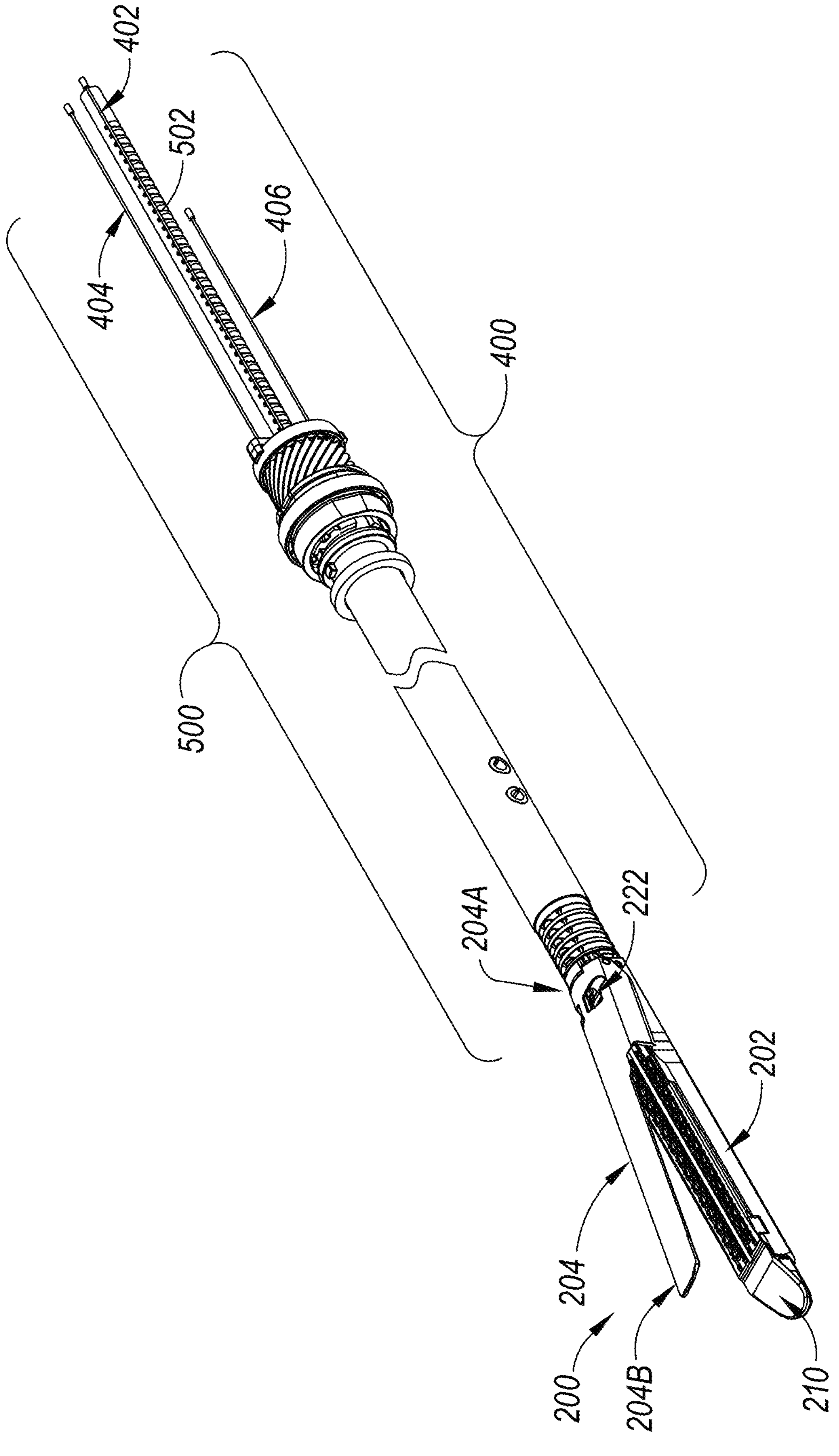
FIG. 2 is a partial perspective view of the surgical instrument of FIG. 1, with select components omitted from view to reveal portions of a cable articulation subsystem, a knife firing subsystem, and a roll subsystem of the surgical instrument.

FIGS. 1-2 show an illustrative surgical instrument 1000 that is configured to grasp, clamp, incise, and seal patient tissue with staples. The surgical instrument 1000 comprises an end effector 200, an articulation joint 300 (also referred to as a "continuum joint"), an articulation drive subsystem 400 configured to articulate the end effector 200 via the articulation joint 300, a knife firing subsystem 500 configured to actuate the end effector 200 between various positions (e.g., an open position, a grasping position, and a clamping position) and to incise and staple patient tissue, a roll subsystem 600 configured to rotate the end effector 200 about a roll axis RA, and a housing 700.

Figure 3:
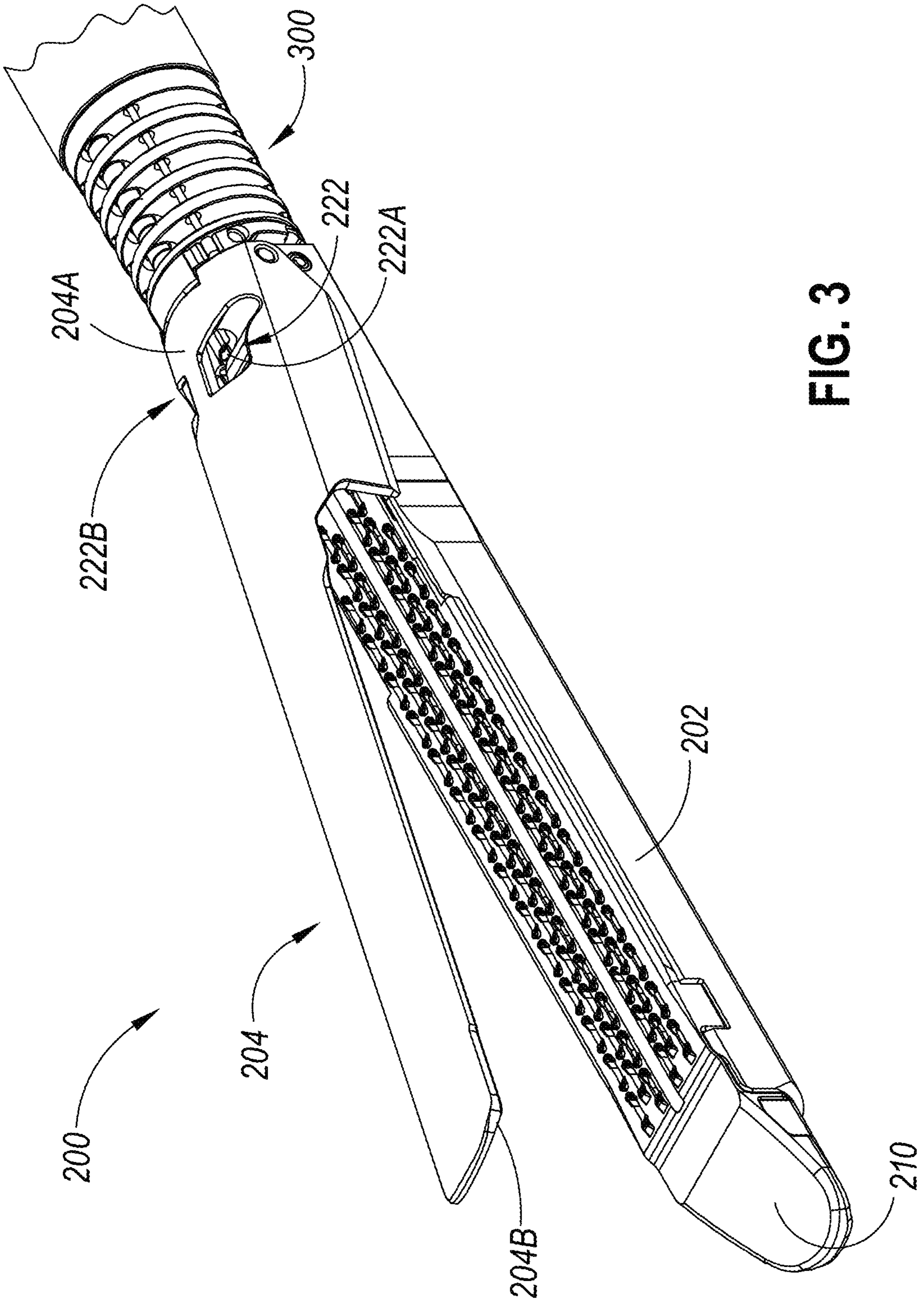
FIG. 3 is an enlarged perspective view of the end effector and the articulation joint of the surgical instrument of FIG. 1.
Figures 4, 5:
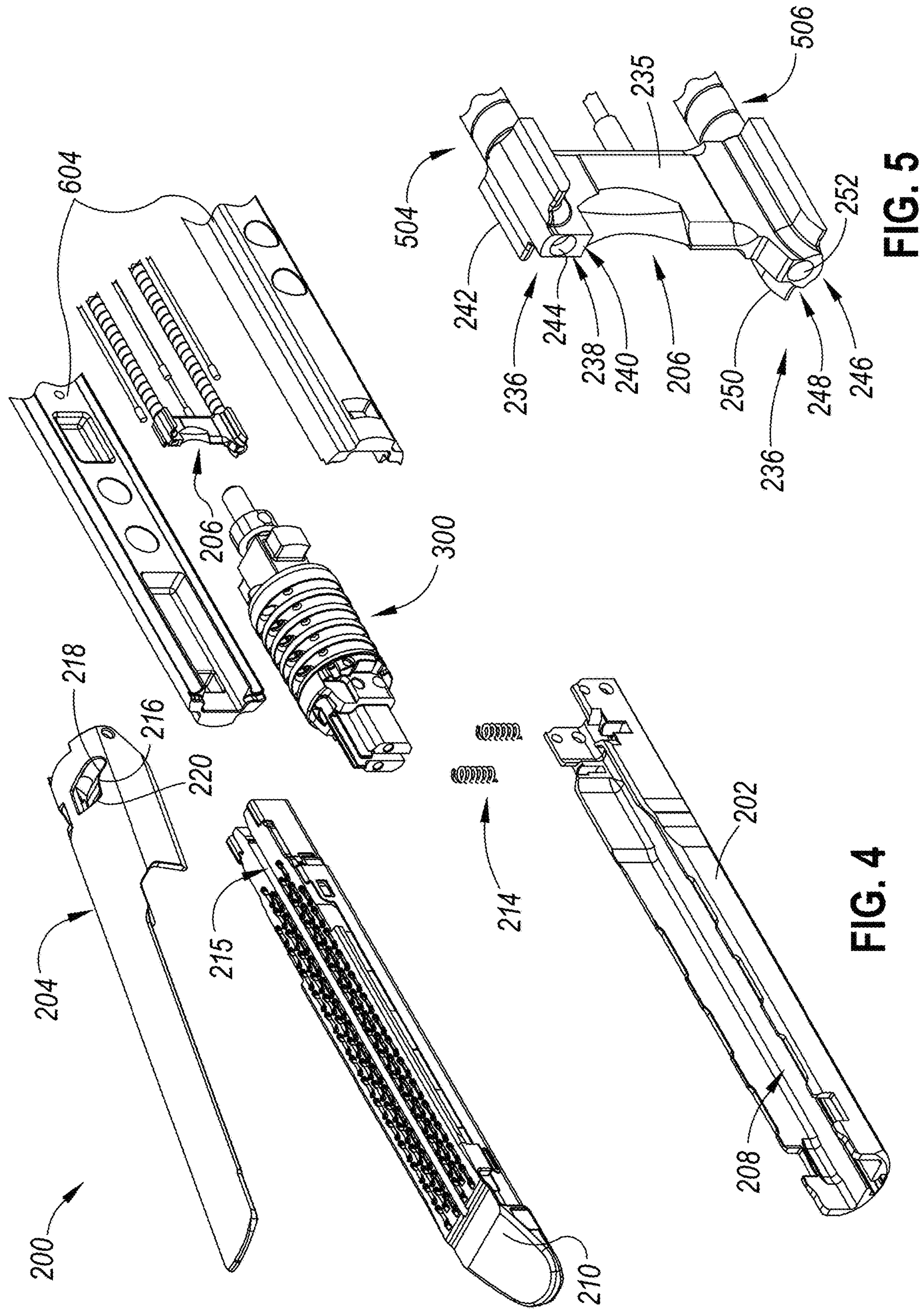
FIG. 4 is an exploded view of a distal end portion of the surgical instrument of FIG. 1.
FIG. 5 is an enlarged perspective view of a knife of the end effector of the surgical instrument of FIG. 1.
Figure 7:
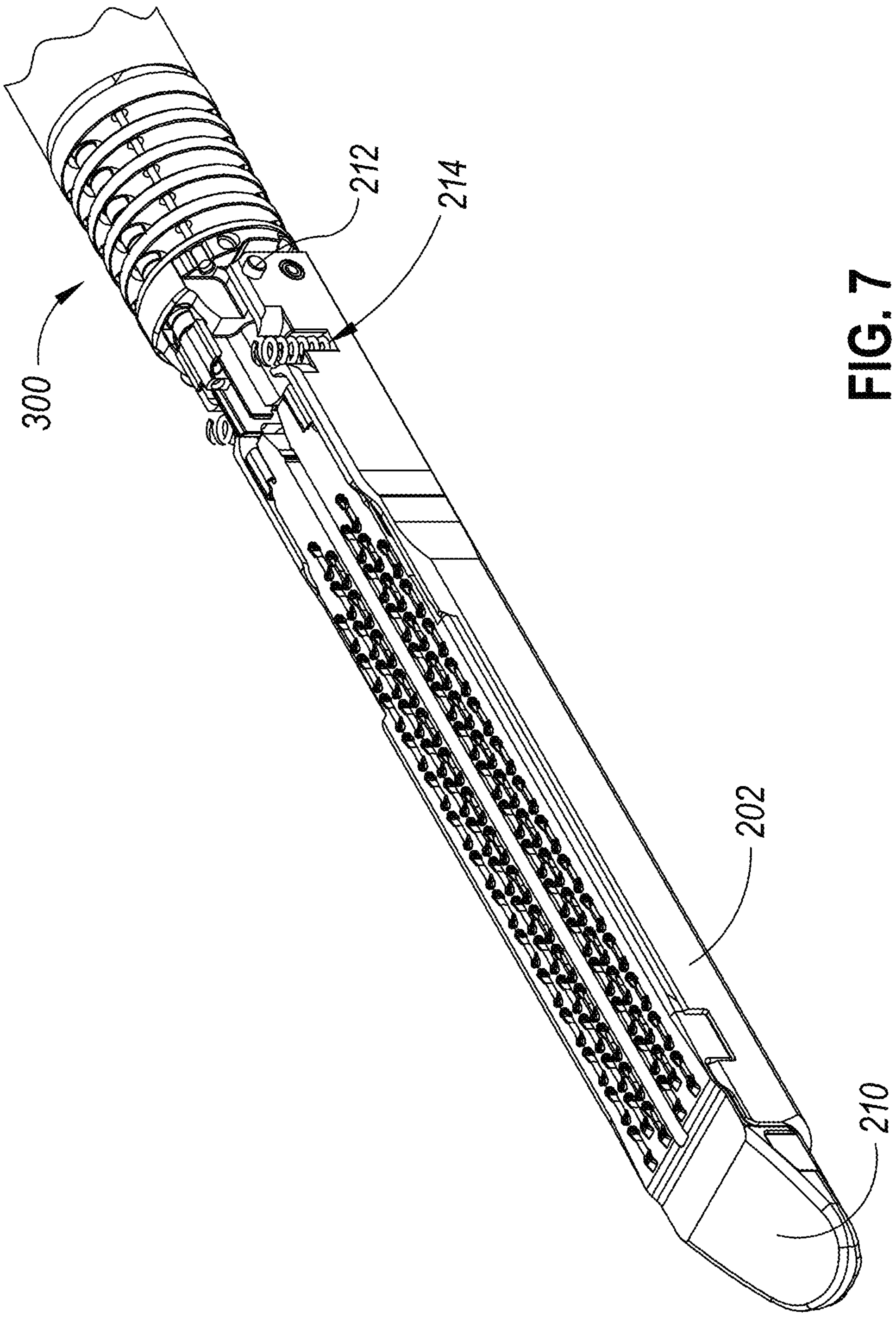
FIG. 7 is an enlarged perspective view of the end effector and the articulation joint of FIG. 3, with an anvil of the end effector omitted.

As shown best in FIGS. 3-4, the end effector 200 comprises a first jaw 202 (also known as a "cartridge jaw" or a "channel") and a second jaw 204 (also known as an "anvil jaw" or just "anvil") movable relative to the cartridge jaw 202 between an open position and a closed position. The cartridge jaw 202 and anvil 204 may be elongated in form. The cartridge jaw 202 defines an elongated channel 208 for receiving a staple cartridge 210 (also known as a "reload"). The anvil 204 has a proximal end 204A, a distal end 204B, and a ramp surface 216 defined at the proximal end 204A, which is described in greater detail below with respect to FIGS. 4 and 9A-9D. The cartridge jaw 202 and anvil 204 are pivotally coupled via a pivot pin 212 that extends through the cartridge jaw 202 and the anvil 204. As seen in FIG. 7, one or more biasing springs 214 extend between the cartridge jaw 202 and anvil 204 to bias the anvil 204 to the open position.

The ramp surface 216 may be visible via a kidney bean-shaped opening 222 (which may be formed as part of the manufacturing process to make the ramp surface 216) that has a first lateral end 222A and a second lateral end 222B. In other words, the kidney bean-shaped opening may be open at its lateral ends 222A, 222B (FIG. 3). As seen in FIG. 4, the ramp surface 216 forms a lower surface of the kidney bean-shaped opening 222. The ramp surface 216 can be arcuately shaped. For example, as shown particularly in FIGS. 4 and 9A-9D, it may be upwardly sloped at a first angle 218 and arcuately taper, in a distal direction, to a substantially horizontal second angle 220.

Figure 8A:
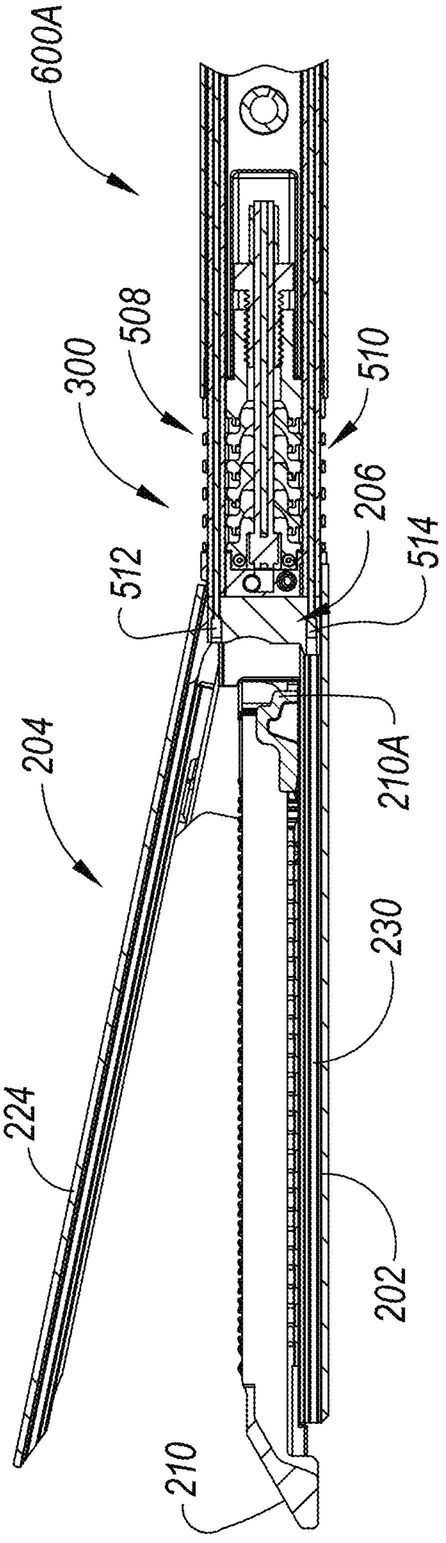
FIG. 8A is a side cross-sectional view of a distal end portion of the surgical instrument of FIG. 1, depicting the anvil in an open position.

The anvil 204 further defines a longitudinally extending upper knife channel 224 (see FIG. 8A, etc.). As shown particularly in FIG. 6, the upper knife channel 224 includes a centrally disposed cylindrical upper knife channel portion 226 and at least one lateral upper knife channel wing 228 that extends away from the upper knife channel portion 226. While the term 'cylindrical' is used, the channel portion 226 need not resemble a perfect cylinder.

Figure 17:
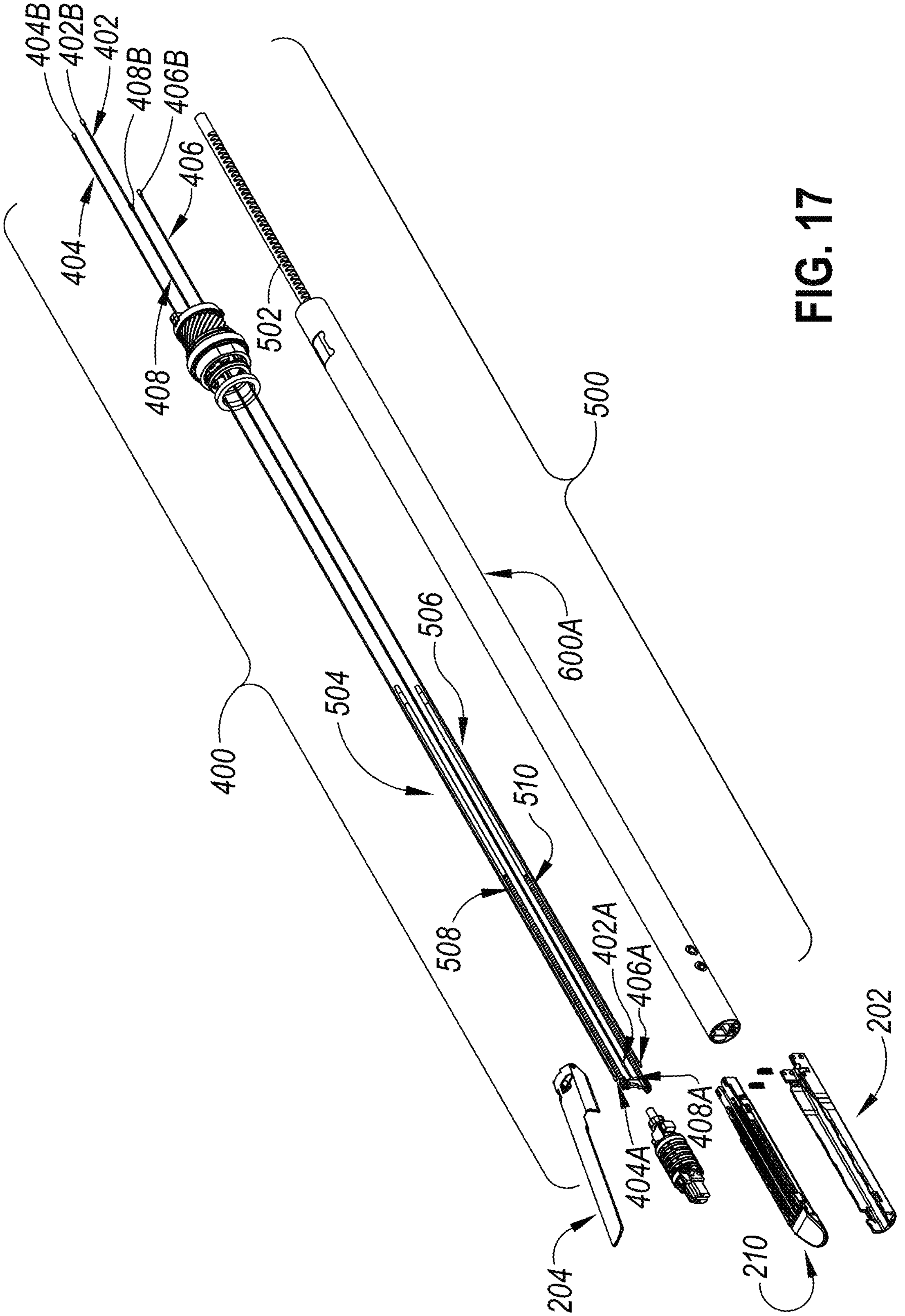
FIG. 17 is an exploded perspective view of a portion of the surgical instrument of FIG. 1, depicting portions of the cable articulation subsystem, the knife firing subsystem, and the roll subsystem.

As shown in FIGS. 2 and 17, the surgical instrument 1000 further comprises a knife firing subsystem 500 operable to close the anvil 204 during a closure stroke. After the end effector 200 is closed, the knife firing subsystem 500 is operable to incise and staple, with staples from the staple cartridge 210, the patient tissue captured between the staple cartridge 210 (which is retained by the cartridge jaw 202) and anvil 204 during a firing stroke.

As shown best in FIGS. 4-6, the knife firing subsystem 500, explained further below in greater detail, includes a knife 206 having a knife sled 236. The knife sled 236 functions as a firing driver by driving cartridge sled 210A distally through a firing stroke, as described below. In some instances, knife sled 236 may be referred to as an I-beam. The knife sled 236 includes an upper knife tab 238 and a lower knife tab 246. The upper knife tab 238 includes a centrally disposed cylindrical upper knife tab portion 240 and at least one upper knife tab lateral wing 242 that extends away from the upper knife tab portion 240. While the term 'cylindrical' is used, the tab portion need not resemble a perfect cylinder.

The upper knife tab 238 may include a pair of lateral wings 242 configured to slidably ride in the upper knife channel 224 to move the anvil 204 between the open position, the grasping position, and the clamping position. Accordingly, the end effector 200 employs "knife-based closure" in which closure of the anvil 204 relative to the channel 208 is driven by distal advancement of the knife 206. Each lateral wing 242 may include a ramped surface 242A that engages the anvil ramp surface 216. The upper knife tab portion 240 defines an upper knife tab opening 244 that is configured to receive a barrel crimp coupled to a center cable 512, which is described in greater detail below. The lower knife tab 246 includes a centrally disposed cylindrical lower knife tab portion 248 and at least one lower knife tab lateral wing 250 that extends away from the lower knife tab portion 248. While the term 'cylindrical' is used, the lower knife tab portion 248 need not resemble a perfect cylinder. In some versions, the lower knife tab 246 includes a pair of lateral wings 250. The lower knife tab portion 248 defines a lower knife tab opening 252 that is configured to receive a barrel crimp coupled to a center cable 514, as described in greater detail below.

The staple cartridge 210 may be generally constructed and operable in accordance with the teachings of U.S. patent application Ser. No. 18/588,684, entitled "Methods of Surgical Stapling," filed on Feb. 27, 2024, issued as U.S. Pat. No. 12,471,913 on Nov. 18, 2025, the disclosure of which is incorporated by reference herein in its entirety. In use, the end effector 200 is positioned relative to patient tissue such that the staple cartridge 210 is disposed on a first side of the tissue and the anvil 204 is positioned on an opposed second side of the tissue. The anvil 204 is then approximated toward the staple cartridge 210 to compress and clamp the tissue against the deck of the staple cartridge 210. Thereafter, the surgical instrument 1000 is fired so that the knife 206 advances distally through the staple cartridge to both cut the clamped tissue and simultaneously actuate staple drivers housed within the staple cartridge to drive an array of staples into the clamped tissue on either side of the cut line.

Figure 6:
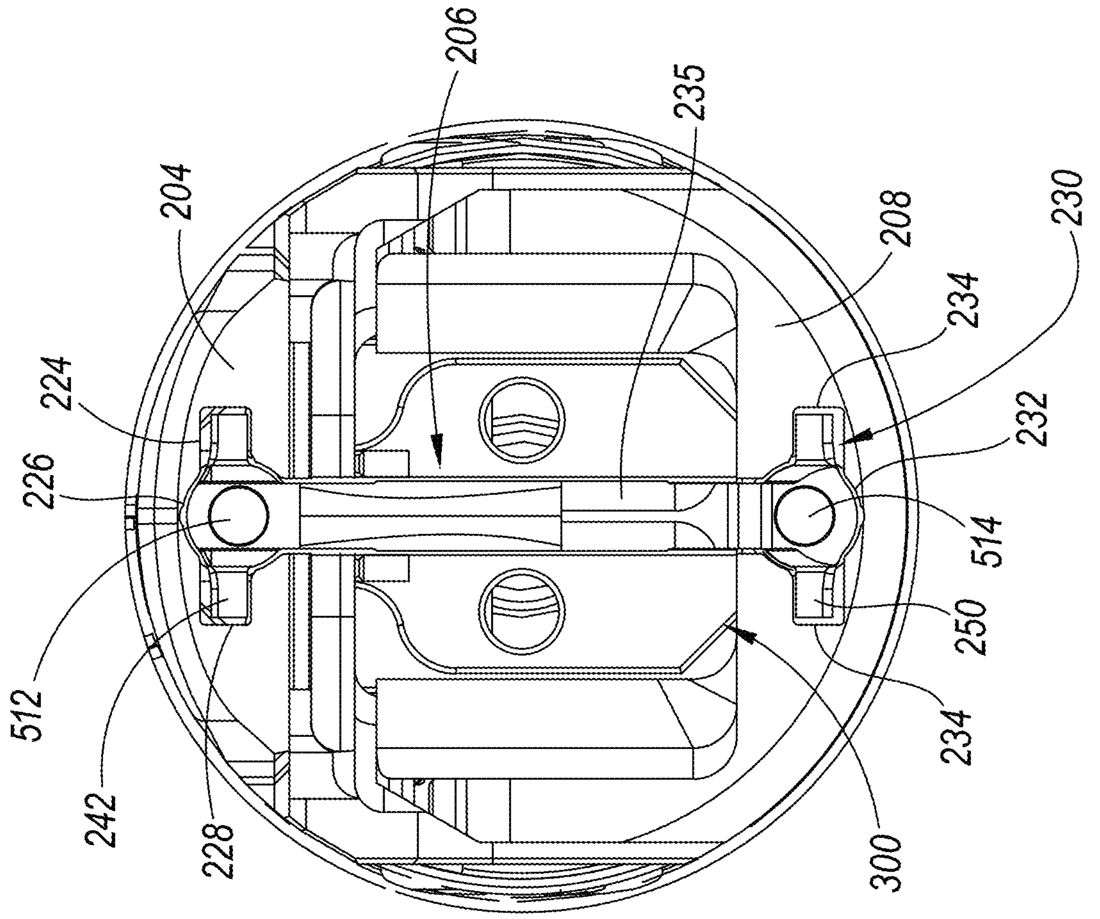
FIG. 6 is an end view of the end effector of FIG. 3.

Referring to FIG. 6, the lower knife channel 230 includes a centrally disposed cylindrical lower knife channel portion 232 and at least one lateral lower knife channel wing 234 that extends away from the lower knife channel portion 232.

While the term 'cylindrical' is used, the channel portion 232 need not resemble a perfect cylinder. Other arrangements of staple cavities and staples may be possible. For example, in some versions, a lower knife channel 230 can be defined in the cartridge jaw 202.

Figure 8B:
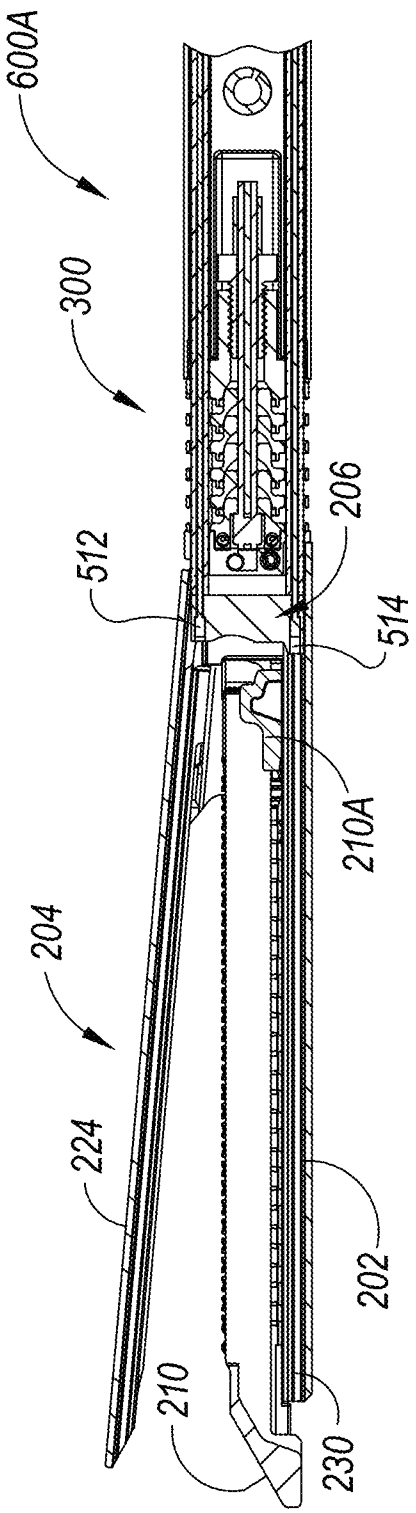
FIG. 8B is a side cross-sectional view of the distal end portion of the surgical instrument of FIG. 1, depicting the anvil in a grasping position with the knife partially advanced.
Figure 8C:
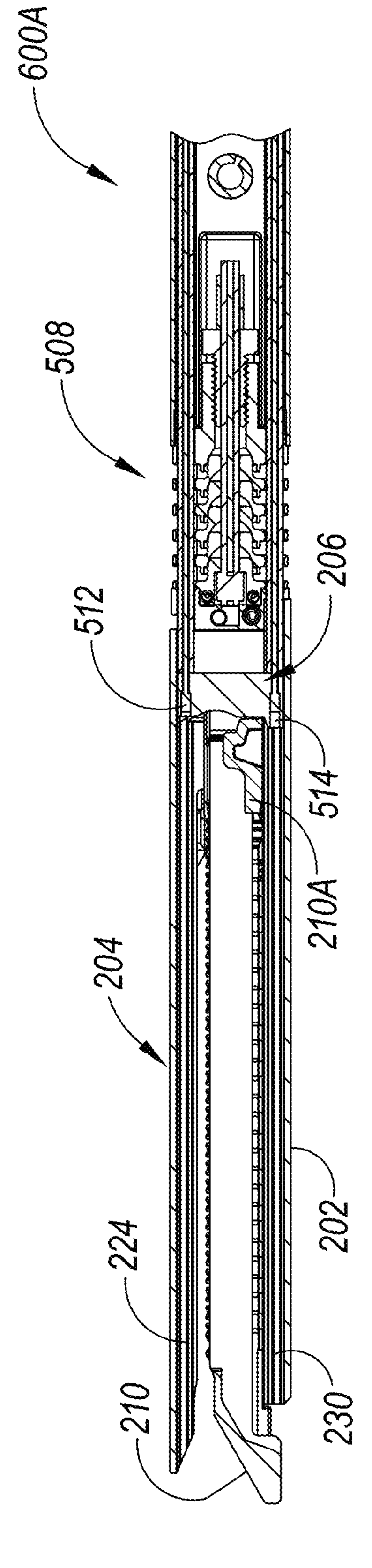
FIG. 8C is a side cross-sectional view of the distal end portion of the surgical instrument of FIG. 1, depicting the anvil in a clamping position with the knife partially advanced.
Figure 8D:
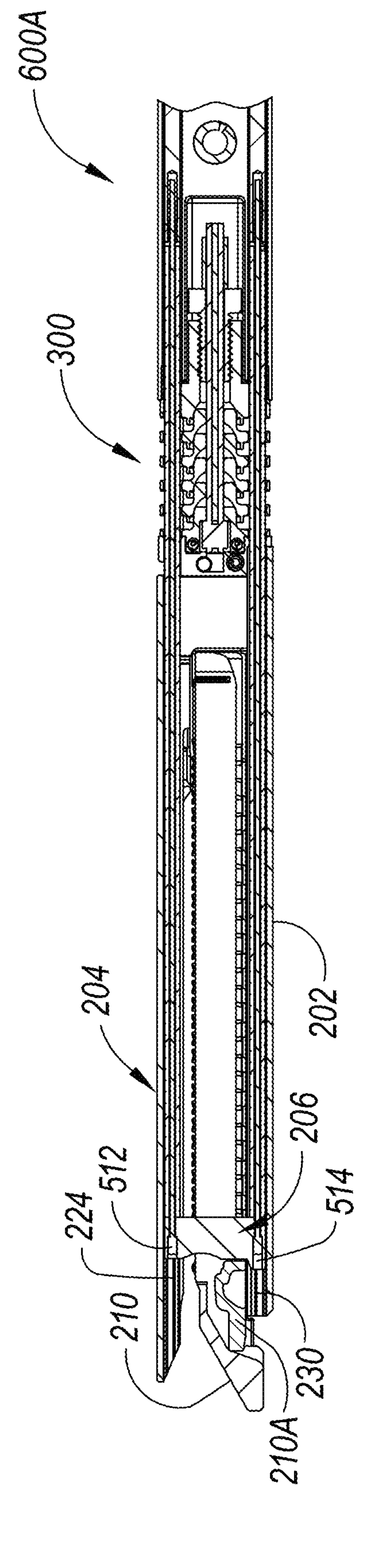
FIG. 8D is a side cross-sectional view of the distal end portion of the surgical instrument of FIG. 1, depicting the anvil in the clamping position with the knife fully advanced.

Further to the above, the knife sled 236 is moved distally and proximally by a firing rod 502. The firing rod 502 is configured to apply an indirect force to the knife sled 236, via push coils 508, 510 that directly engage the knife sled 236 (discussed in greater detail below), and push the knife sled 236 toward the distal end of the end effector 200 through a firing stroke. As the firing rod 502 is advanced distally, knife sled 236 rides in the lower knife channel 230 and the upper knife channel 224. At the onset of travel, the upper knife tab 238 rides along the anvil ramp surface 216. Specifically, as particularly seen in the sequence of FIGS. 8A-8D and 9A-9D, movement of the knife sled 236 distally causes the upper knife tab ramped surface 242A to slide along the anvil ramp surface 216. This movement first urges the anvil 204 closed to a position (e.g., FIGS. 8B and 9B) where a compressive force is applied to the tissue sufficient to grasp it (referred to as the grasping position). Continued movement of the knife sled 236 up the ramp surface 216 (e.g., see FIGS. 8C and 9C) results in a compressive force being applied to the tissue (referred to as the clamping position). As the anvil ramp surface 216 transitions to its substantially horizontally angled surface 220 (e.g., see FIGS. 8D and 9D), the upper knife tab 238 can slide within the upper knife channel 224 to drive the stapling and transection of the tissue.

Figure 18:
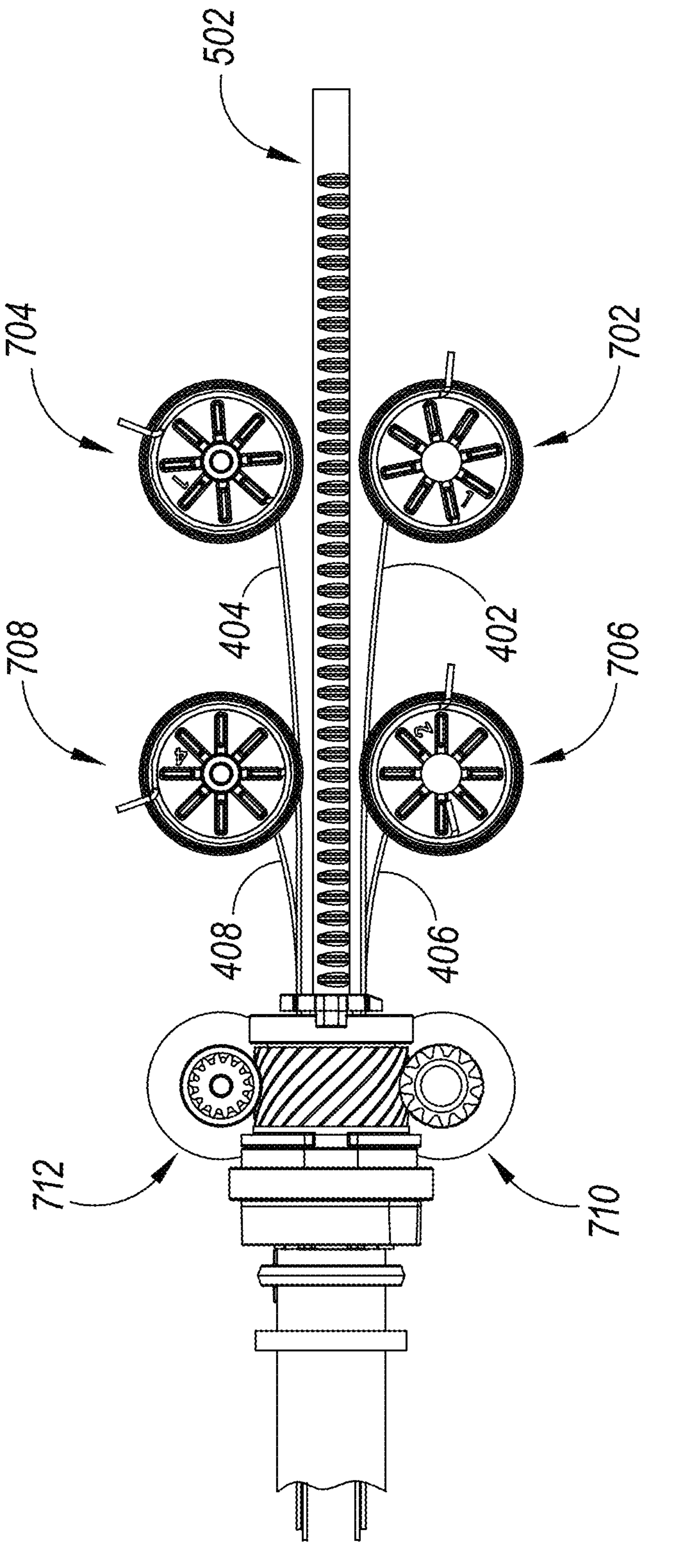
FIG. 18 is a top view of a proximal end of the surgical instrument of FIG. 1, depicting portions of the cable articulation subsystem, the knife firing subsystem, and the roll subsystem.
Figure 19:
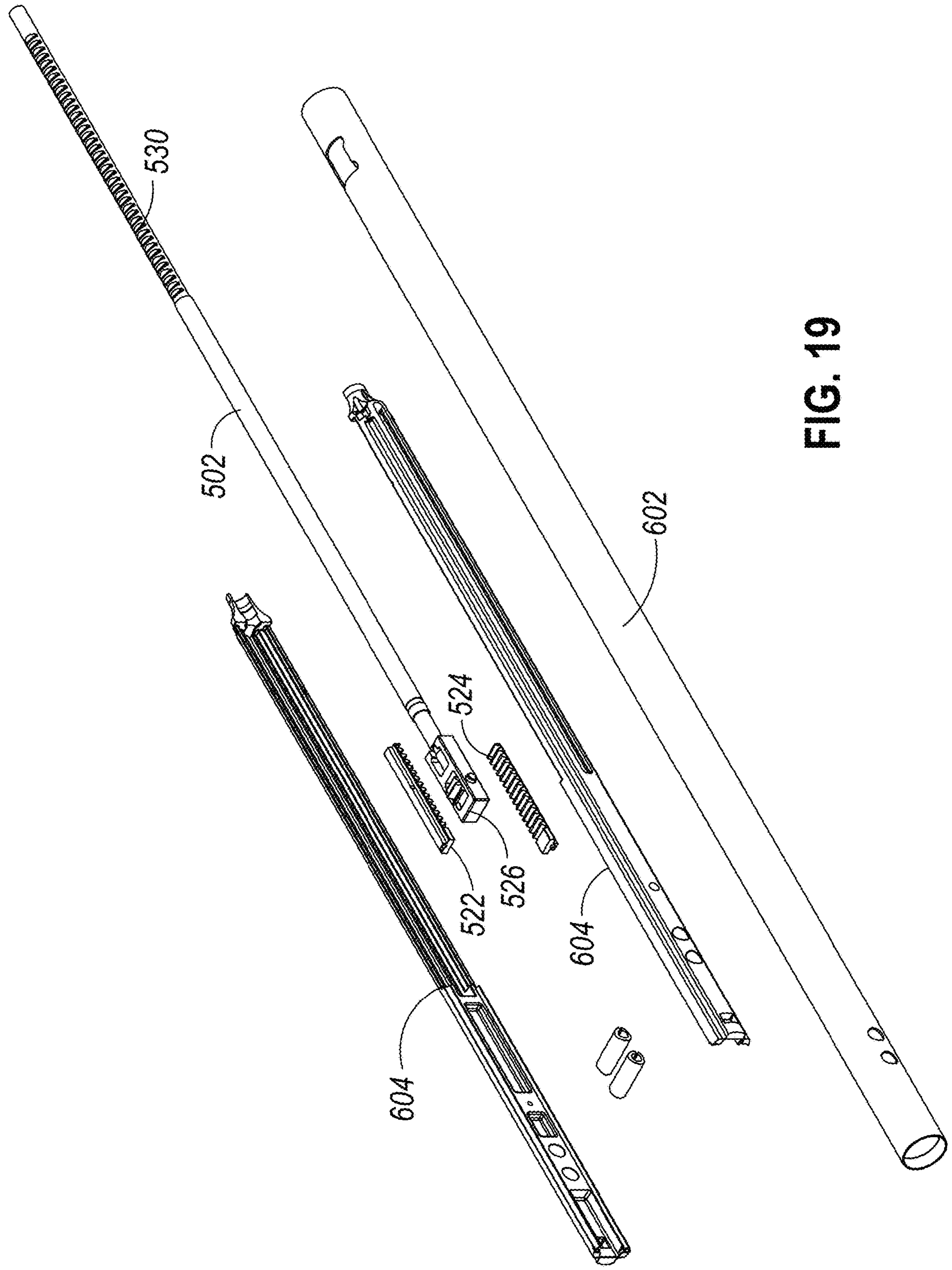
FIG. 19 is a perspective view of a shaft assembly, a differential, and a firing rod of the surgical instrument of FIG. 1.

As shown in FIG. 1, the surgical instrument 1000 further comprises a body exemplified as a housing 700 configured to engage a robotic platform (not shown). In other versions, the body may be configured as a handle configured to be gripped and manipulated by a clinician. As best shown in FIGS. 1 and 19, a shaft assembly 600A extends distally from the housing 700 and includes a rotatable outer shaft 602 and an inner shaft 604 arranged in two clamshell halves, with the outer shaft 602 being rotatably mounted to the housing 700 about a rotation joint (not shown), which may include one or more bearings. The inner shaft 604 is rotationally fixed to the outer shaft 602 and is configured such that articulation cables 402, 404, 406, 408 can be partially wound therearound without becoming tangled. As shown in FIG. 18, the housing 700 may house (1) a firing puck assembly 712 as part of the knife firing subsystem 500 operable to close the end effector 200, fire staples, and transect tissue, (2) a set of articulation puck assemblies 702, 704, 706, 708 as part of the articulation subsystem 400 operable to articulate the end effector 200 relative to the shaft assembly 600A, and (3) a shaft roll puck assembly 710 as part of the roll subsystem 600 configured to roll the outer shaft 602.

Referring to FIGS. 10-13, the articulation joint 300 comprises an array of joint discs 302 arranged longitudinally, and a center beam assembly 306 that cooperates with the joint discs 302 to provide articulation of the end effector 200 with at least two degrees of freedom (e.g., yaw and pitch), as described further below. Each joint disc 302 includes a central opening 304 that is configured to align coaxially with the central opening 304 of the other joint discs when the articulation joint 300 is in a straight, non-articulated state. The center beam assembly 306 extends longitudinally through the central openings 304 of joint discs 302 and applies a compressive axial force to the array of joints discs 302 to couple the joint discs 302 with one another. The joint discs 302 are nestably stacked with one another along the center beam assembly 306 such that longitudinally adjacent joint discs 302 movably interface with one another.

Figure 9B:
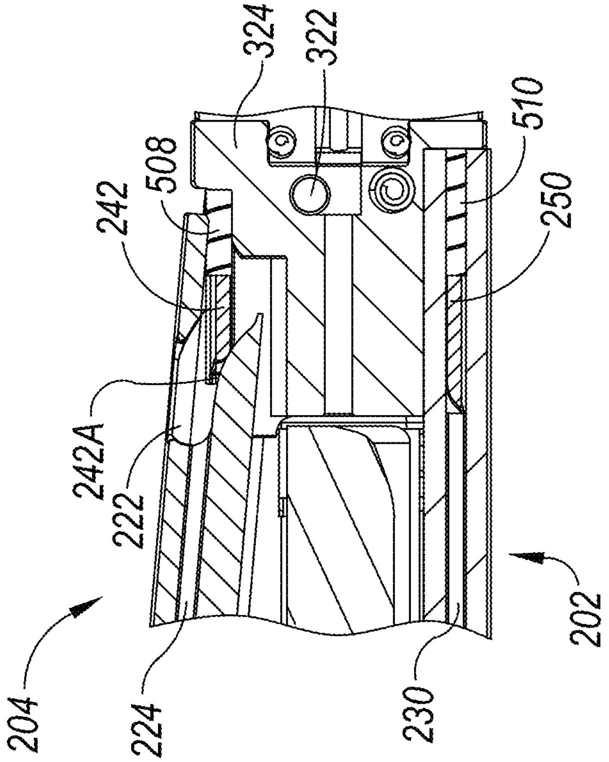
FIG. 9B is an enlarged side cross-sectional view of the proximal end portion of the end effector of the surgical instrument of FIG. 1, depicting the anvil in a grasping position with the knife partially advanced.
Figure 9A:
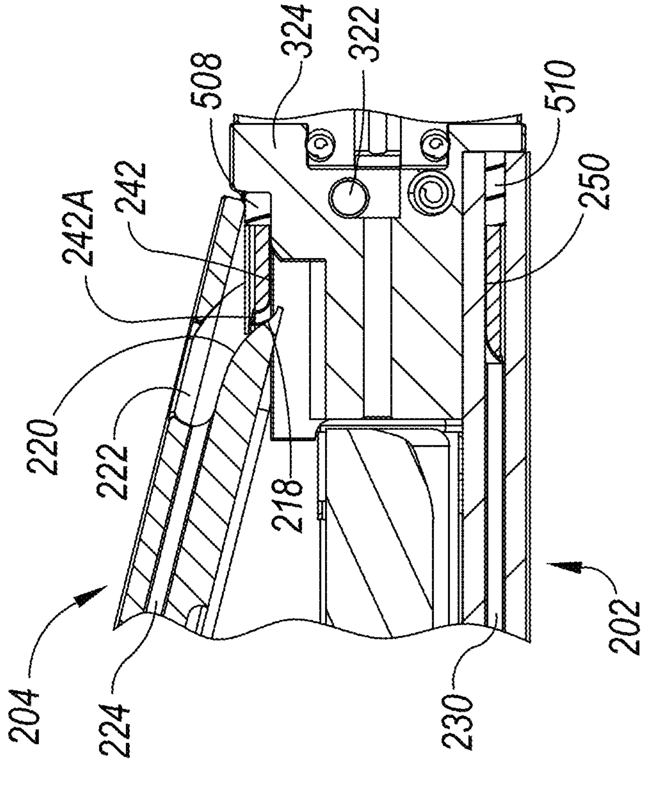
FIG. 9A is an enlarged side cross-sectional view of a proximal end portion of the end effector of the surgical instrument of FIG. 1, depicting the anvil in the open position.
Figure 9D:
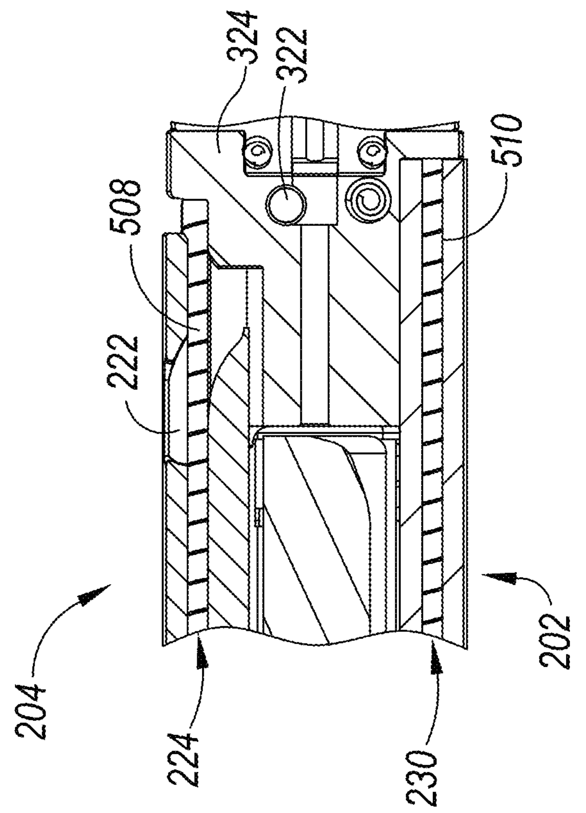
FIG. 9D is an enlarged side cross-sectional view of the proximal end portion of the end effector of the surgical instrument of FIG. 1, depicting the anvil in the clamping position with the knife fully advanced.
Figure 9C:
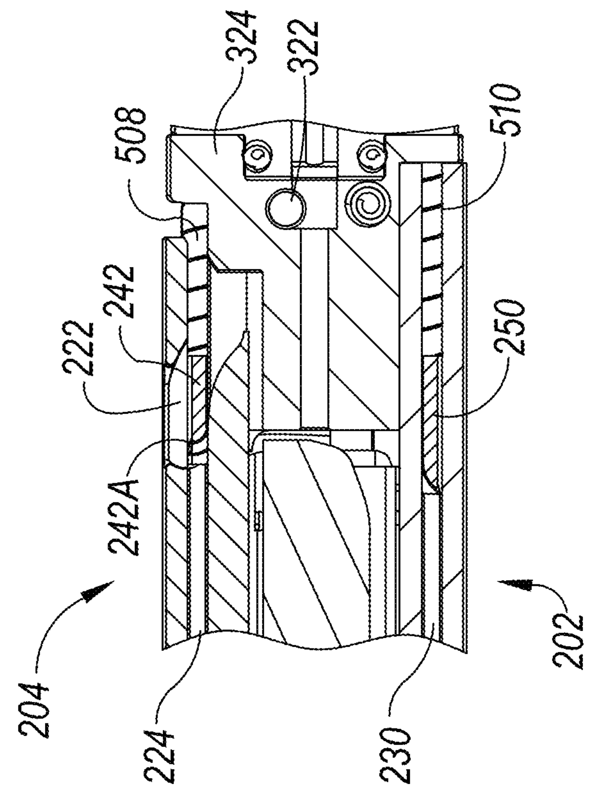
FIG. 9C is an enlarged side cross-sectional view of the proximal end portion of the end effector of the surgical instrument of FIG. 1, depicting the anvil in a clamping position with the knife partially advanced.
Figure 10:
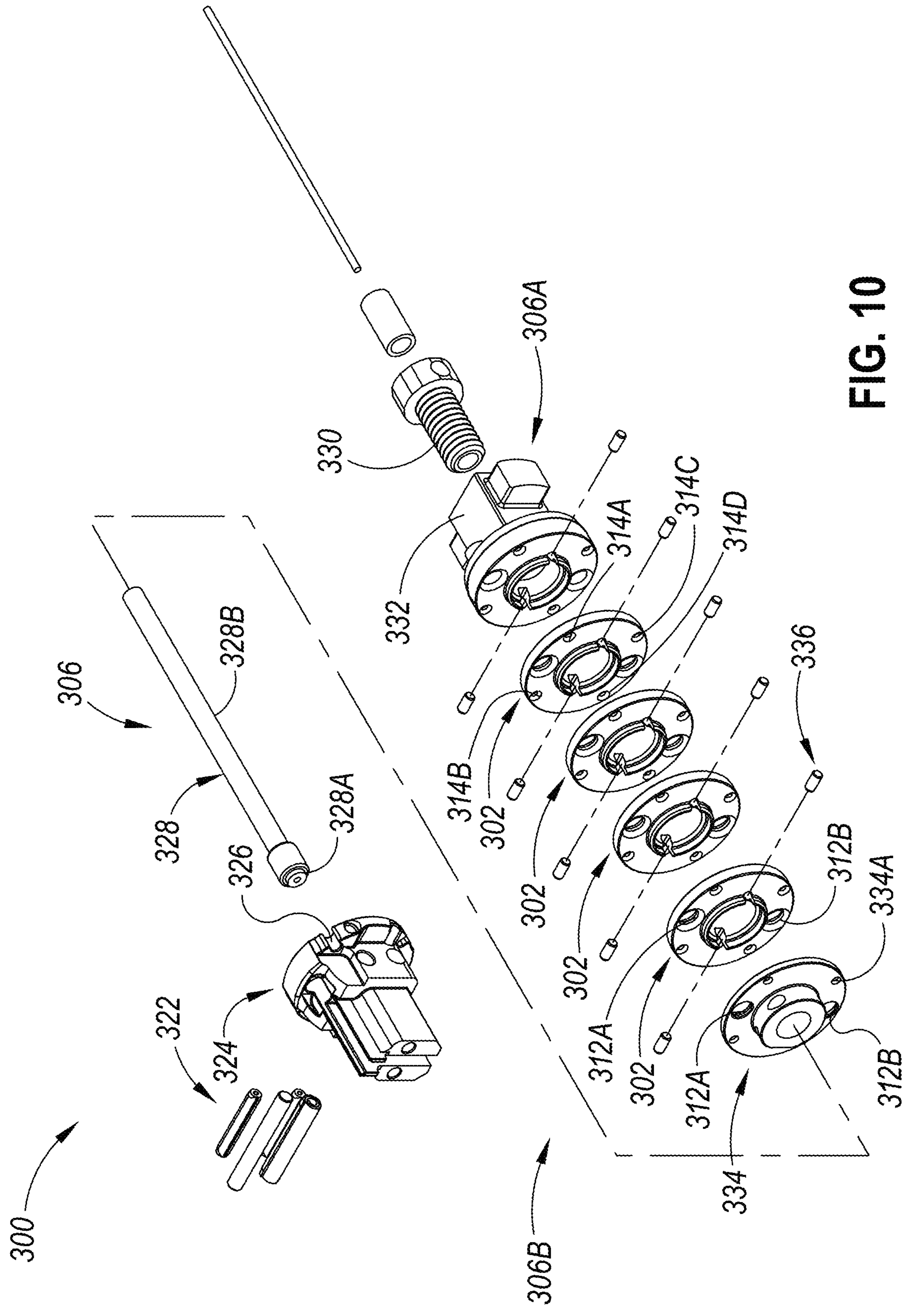
FIG. 10 is an exploded perspective view of the articulation joint of the surgical instrument of FIG. 1.
Figure 11:
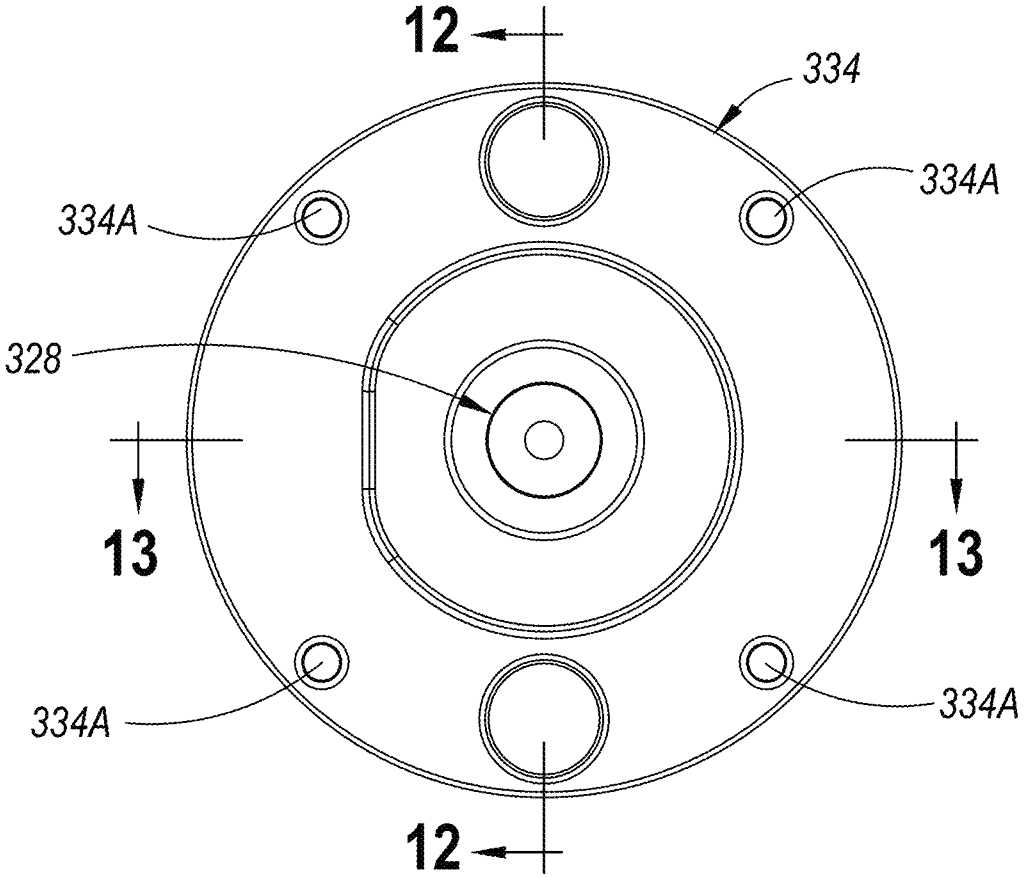
FIG. 11 is an end view of the articulation joint of FIG. 10.

As seen in FIGS. 9A-10, a distal end 306B of the center beam assembly 306 includes a distal retainer 324 that couples the distal end of the articulation joint 300 with a proximal end of the cartridge jaw 202 via one or more fasteners 322, thereby mechanically grounding and retaining the cartridge jaw 202 and thus the end effector 200 relative to the articulation joint 300. The distal retainer 324 includes a plurality of clearance pockets 326 that receive distal ends of articulation cables 402, 404, 406, 408. The distal end 306B further includes a distal retention disc 334 that defines a plurality of cable retention openings 334A. A proximal end 306A of the center beam assembly 306 includes a proximal retainer 332 that couples the proximal end of the articulation joint 300 with a distal end of the shaft assembly 600A.

Figure 12:
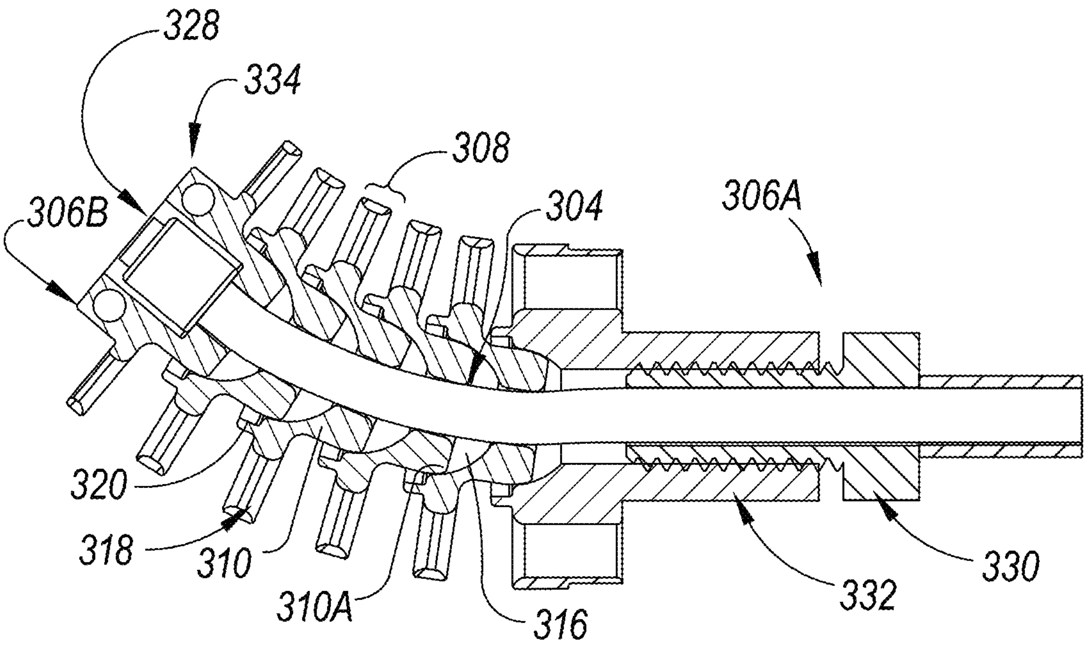
FIG. 12 is a cross-sectional view of a portion of the articulation joint of FIG. 10, taken along line 12-12 in FIG. 11.
Figure 13:
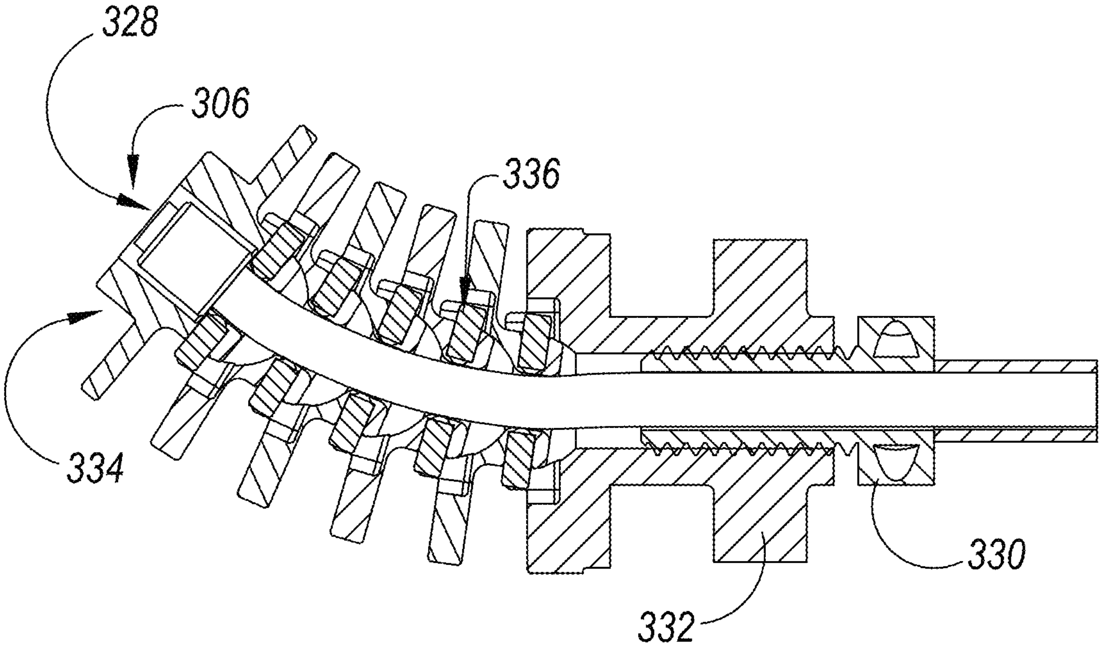
FIG. 13 is a cross-sectional view of a portion of the articulation joint of FIG. 10, taken along line 13-13 in FIG. 11.
Figure 14:
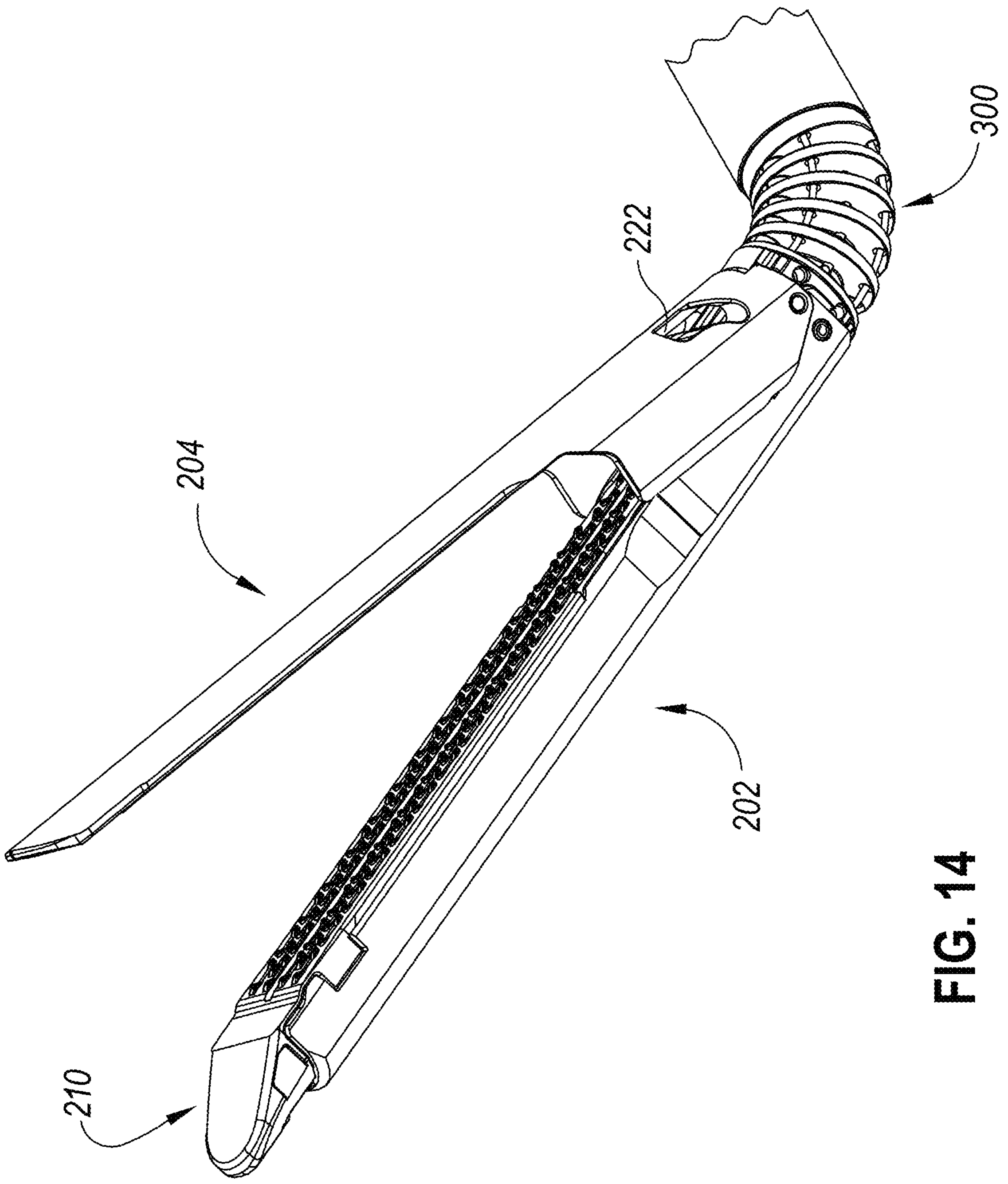
FIG. 14 is a perspective view of the distal end of the surgical instrument of FIG. 1, depicting the end effector articulated vertically and laterally with the anvil open.
Figure 15:
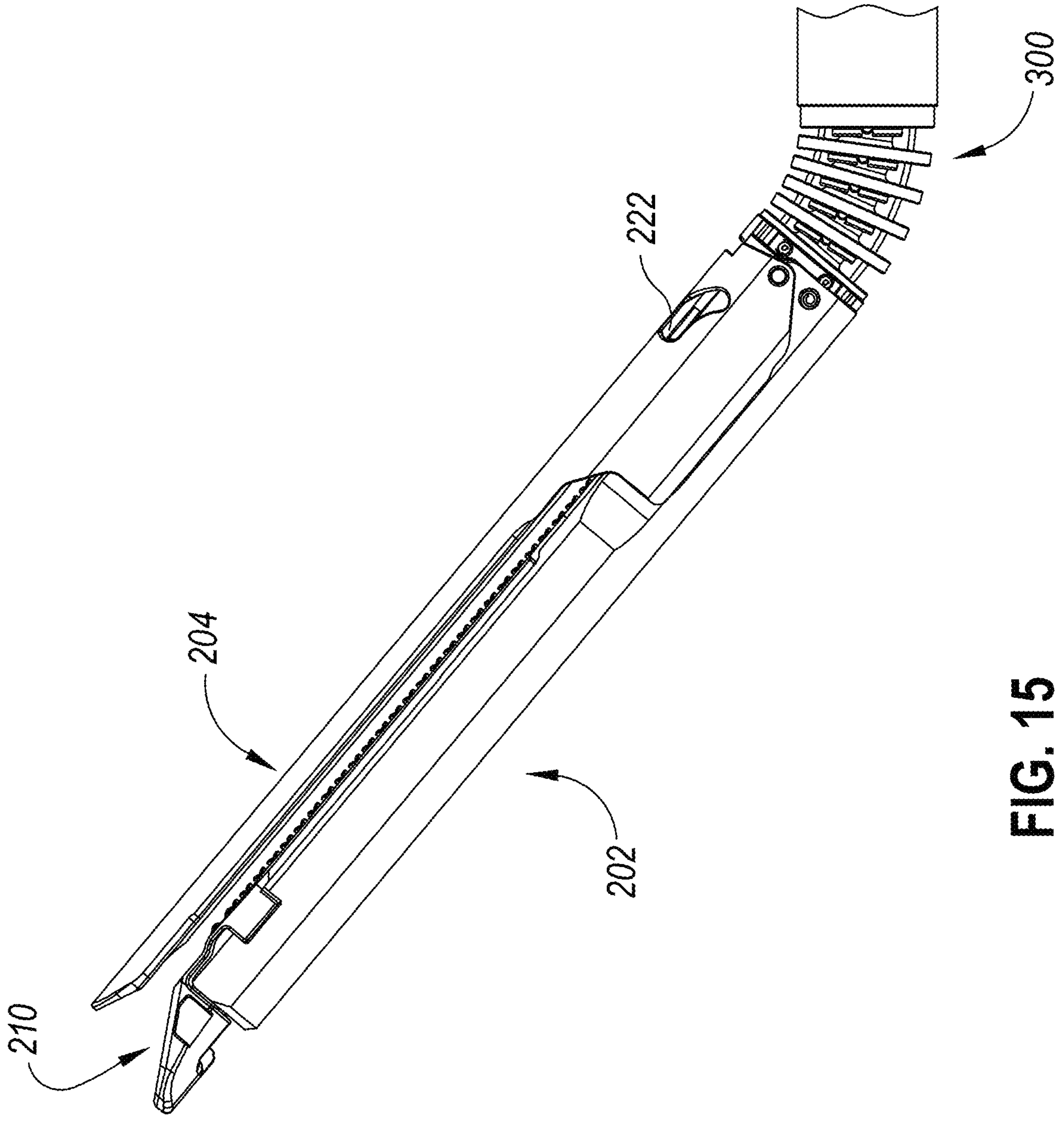
FIG. 15 is a side view of the distal end of the surgical instrument of FIG. 1, depicting the end effector articulated vertically with the anvil closed.
Figure 16:
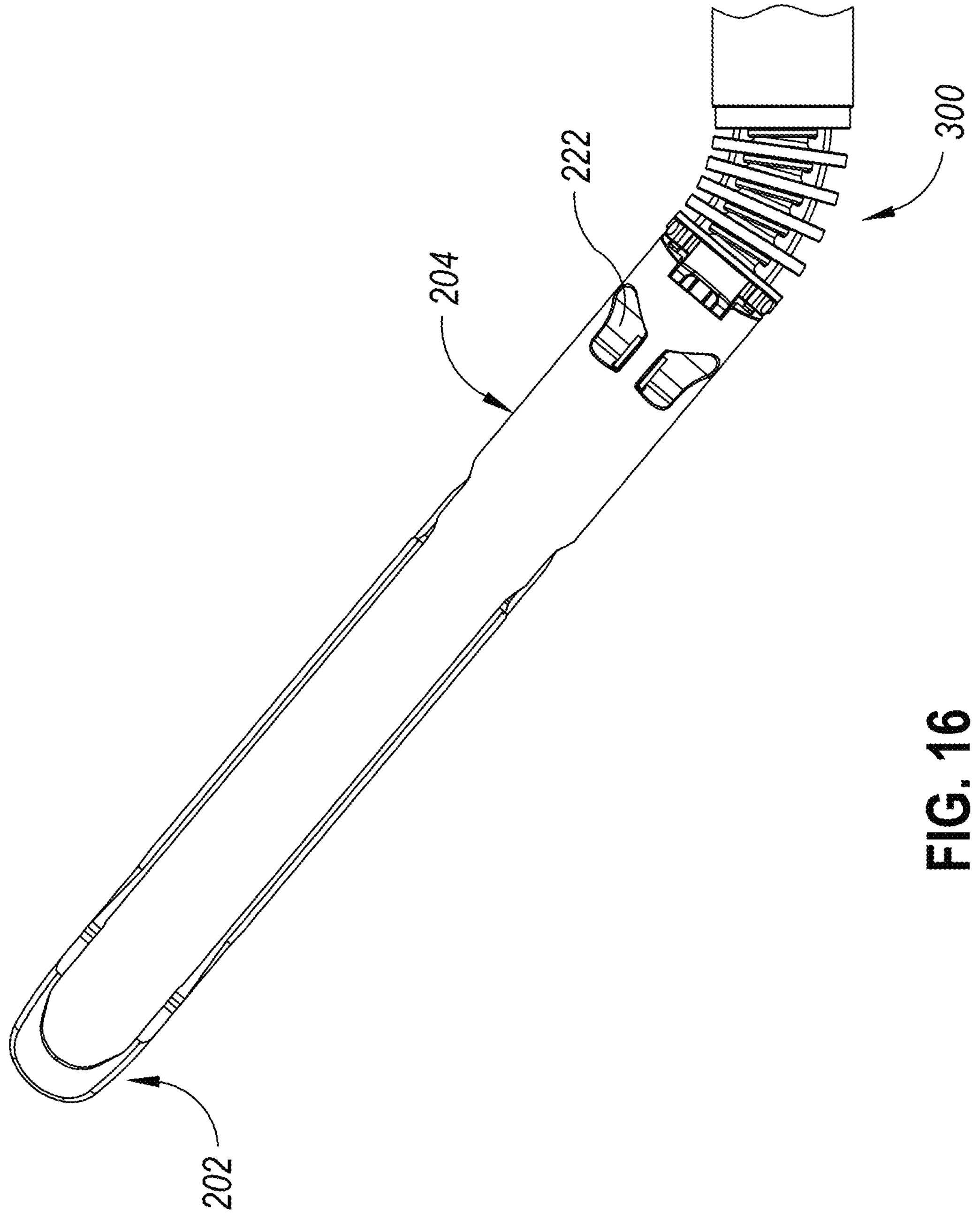
FIG. 16 is a top view of the distal end of the surgical instrument of FIG. 1, depicting the end effector articulated laterally with the anvil closed.

As shown particularly in FIGS. 10, 12, and 13, each joint disc 302 includes an articulation socket 308, an articulation pin 310 protruding outwardly from the articulation socket 308, a first push coil opening 312A defined through the articulation socket 308 and configured to receive a first push coil 508 therethrough, a second push coil opening 312B defined through the articulation socket 308 and configured to receive a second push coil 510 therethrough, and a plurality of articulation cable openings 314A-314D (e.g., a first articulation cable opening 314A, a second articulation cable opening 314B, a third articulation cable opening 314C, and a fourth articulation cable opening 314D) defined through the articulation socket 308 and configured to receive a respective articulation cable 402, 404, 406, 408 (e.g., a first articulation cable 402, a second articulation cable 404, a third articulation cable 406, and a fourth articulation cable 408) therethrough, and discussed in greater detail below. As shown in FIGS. 12 and 13, the central opening 304 is defined in the articulation pin 310 of each joint disc 302. In some versions, three articulation cable openings 314A, 314B, 314C are provided to correspond to three articulation cables 402, 404, 406, while in other versions, four articulation cable openings 314A, 314B, 314C, 314D are provided to correspond to four articulation cables 402, 404, 406, 408.

Each joint disc 302 further includes a rounded articulation pin proximal end 310A and a semi-spherical pin-receiving opening 316 defined in the articulation socket 308. As shown particularly in FIGS. 12 and 13, each rounded articulation pin proximal end 310A pivotally engages in an adjacent pin-receiving opening 316 of an adjacent joint disc 302, with the exception of a proximal-most end 310A that engages with the proximal retainer 332. The articulation pin proximal end 310A and pin-receiving opening 316 interface functions in a similar manner as a swivel bearing. Moreover, the articulation socket 308 includes a socket disc 318 and a pin retention socket 320. A pair of pins 336 are used to provide rotational coupling about a primary axis of the shaft assembly 600A from one disc 302 to the next. In other words, the pins constrain a rotational degree of freedom between adjacent joint discs 302 about the roll axis RA of the instrument 1000. In alternative versions, this feature can be integral to the joint disc 302.

The center beam assembly 306 further includes a center beam 328 that extends longitudinally through the central openings 304 of the joint discs 302. The center beam 328 includes a nitinol core 328A and a stainless-steel collar 328B wound over the nitinol core 328A that allows the center beam 328 to resiliently flex during deflection of the articulation joint 300. The wound stainless-steel collar 328B may have clockwise braiding and counterclockwise braiding to prevent unwinding thereof. The center beam assembly further includes a jack screw 330 that is threadably coupled with the proximal retainer 332 to adjust an axial compression force exerted by the center beam 328 on the array of joint discs 302, thereby enabling adjustment of a pre-load of the articulation joint 300.

The above-described articulation joint 300 forms a portion of the cable articulation subsystem 400 which allows for precise 360-degree movement of the end effector 200 about the articulation joint 300 with at least two degrees of freedom. In some versions, and as dictated by the roll subsystem 600 as well as a need to limit the amount of wrap of the articulation cables 402, 404, 406, 408, the articulation joint 300 is permitted about 320 degrees of roll within the overall system. The cable articulation subsystem 400 also includes a plurality of articulation cables 402, 404, 406, 408 each having a distal end 402A, 404A, 406A, 408A, coupled to the distal end 306B of the center beam assembly 306, and a proximal end 402B, 404B, 406B, 408B. More specifically, each distal end 402A, 404A, 406A, 408A can include a crimp that engages a cable retention opening 334A of the distal retention disc 334 to maintain its positioning. Each articulation cable is discretely manipulable to cause rotation of the articulation joint 300 and end effector 200 about at least one of a pitch axis PA and a yaw axis YA.

In some versions, three articulation cables may be provided rather than the four cables 402, 404, 406, 408 depicted herein. However, four articulation cables 402, 404, 406, 408 circumferentially spaced approximately ninety degrees from one another (as shown) provide load splitting. Additionally, in alternative versions, three and fourth articulation cable configurations may be spaced non-symmetrically relative to one another.

The shaft assembly 600A and housing 700 also form portions of the cable articulation subsystem 400. More specifically, each articulation cable 402, 404, 406, 408 extends from the articulation joint 300 and through the shaft assembly 600A to the housing 700. The proximal end 402B, 404B, 406B, 408B of each articulation cable (402, 404, 406) is movably mounted in the housing 700 which causes the above-mentioned rotation of the articulation joint 300 and end effector 200. The housing 700 includes articulation puck assemblies 702, 704, 706, 708 with rotatable capstans (not shown) about which corresponding proximal ends 402B, 404B, 406B, 408B of the articulation cables 402, 404, 406, 408 are windably mounted.

The articulation cables 402, 404, 406, 408 are routed through the shaft assembly 600A such that they are disposed between the outer shaft 602 and the inner shaft 604, with the articulation cables 402, 404, 406, 408 being able to partially wind therearound without becoming tangled. The inner shaft 604 also prevents the articulation cables 402, 404, 406, 408 from interfering with other components running down the center of the instrument 1000 (through the inner shaft 604).

The articulation cables 402, 404, 406, 408 are routed and coupled to the end effector 200 via the articulation joint 300 such that movement thereof in a proximal direction (via winding about the capstans of the housing 700) causes the end effector 200 to articulate in a predetermined manner via the articulation joint 300. For example, actuation of the first articulation cable 402 in the proximal direction causes articulation of the end effector 200 upwards and to the left, actuation of the second articulation cable 404 in the proximal direction causes rotation of the end effector 200 upwards and to the right, actuation of the third articulation cable 406 in the proximal direction causes rotation of the end effector 200 downwards and to the left, and actuation of the fourth articulation cable 408 in the proximal direction causes rotation of the end effector 200 downwards and to the right. Similarly, movement of two articulation cables simultaneously will result in blended articulation of the end effector 200. As will be appreciated by those skilled in the art, this configuration provides for the above-mentioned precise 360-degree articulation of the end effector 200 via the articulation joint 300 with at least two degrees of freedom and about 320 degrees of roll.

As shown throughout FIGS. 2, 4, 5, 8A-8D, 9A-9D, 17 and 19, the knife firing subsystem 500 includes the aforementioned knife 206, the aforementioned knife sled 236, a firing rod 502 that drives the knife 206 and/or knife sled 236, a first push rod 504, and a second push rod 506. The firing rod 502 includes a firing rod rack 530 and is driven by a firing puck assembly 712 of the housing 700. The first push rod 504 has a first push rod distal end 504A coupled to the knife sled 236 and a first push rod proximal end 504B coupled to the firing rod 502. Similarly, the second push rod has a second push rod distal end 506A coupled to the knife sled 236 and a second push rod proximal end 506B coupled to the firing rod 502. The distal ends 504A, 506A are coupled to respective upper and lower portions of the knife sled 236 (e.g., the upper knife tab 238 and the lower knife tab 246), which enables the knife 206 to be pushed evenly at its ends. In some versions, the proximal ends 504B, 506B of the push rods 504, 506 are coupled to the firing rod 502 via a differential 520.

The knife firing subsystem 500 is configured in a manner to enable articulation of the end effector 200 while still enabling proper functionality of the knife 206. To that end, the first push rod 504 includes a first flexible section in the form of a first push coil 508 and the second push rod 506 comprises a second flexible section in the form of a second push coil 510. The push coils 508, 510 route through the articulation joint 300 via the respective push coil openings 312A, 312B, and the push rods 504, 506 engage the respective tab openings 244, 252 in the knife sled 236. A first center cable 512 extends through the first push coil 508 to engage the knife sled 236 via a barrel crimp, and a second center cable 514 extends through the second push coil 510 to engage the knife sled 236 via a barrel crimp. The push coils 508, 510 provide the push rods 504, 506 sufficient stability to deliver an axial firing force to the knife 206, while not being too stiff that would prevent articulation at the joint 300. The cables 512, 514, which are engaged with the knife sled 236 as discussed above (see, e.g., FIG. 8A), prevent the push coils 508, 510 from stretching and/or elongating and serve as retraction cables when the rods 504, 506 are retracted towards the proximal end of the surgical instrument 1000. The entirety of each push rod 504, 506 does not extend through the articulation joint 300, and therefore does not need to be flexible. Accordingly, a proximal section of each push rod 504, 506 can be less flexible than the push coils 508, 510.

II. ILLUSTRATIVE TRANSLATING KNIFE LOCKOUT FEATURES

It may be desirable to inhibit firing of the surgical instrument 1000 in instances when the end effector 200 is loaded with a staple cartridge 210 that has already been fired (i.e., a "spent-cartridge" condition), and also when the end effector 200 is not loaded with any staple cartridge at all (i.e., an "absent-cartridge" condition). Attempted firings during such conditions are the result of user error and could result in unintended action on patient tissue; namely, severing the tissue without simultaneously sealing it with staples. The illustrative configurations shown and described below in connection with FIGS. 20-33B are effective to inhibit firing in each of a spent-cartridge condition and an absent-cartridge condition, and thereby protect against such unintended action on patient tissue.

A. Illustrative Lockout Assembly with Pivoting Action

Figure 20:
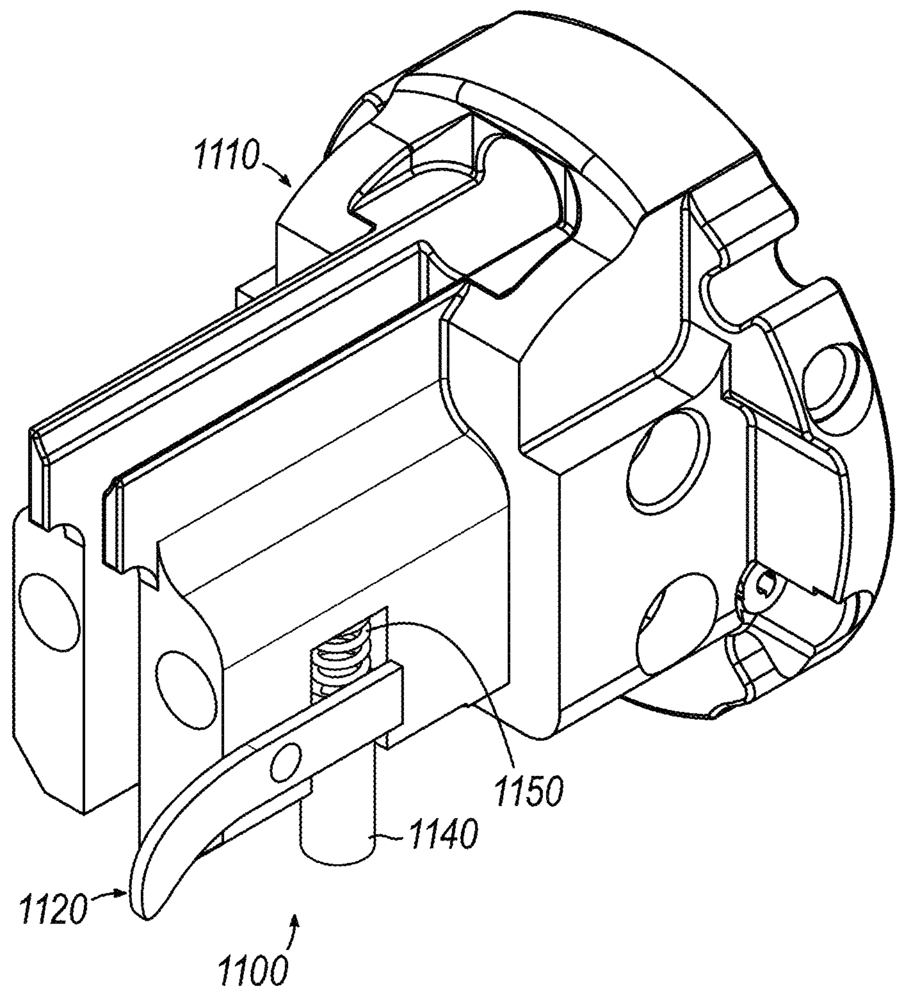
FIG. 20 is a perspective view of an illustrative lockout assembly that may be readily incorporated into the end effector of the surgical instrument of FIG. 1.

FIG. 20 depicts a lockout assembly 1100, which may be readily incorporated into end effector 200 of surgical instrument 1000 described above. For instance, in the present example, lockout assembly 1100 is incorporated into a portion of a distal retainer 1110, which may be incorporated into end effector 200 in lieu of distal retainer 324 described above. It should be understood that distal retainer 1110 of the present example is substantially similar to distal retainer 324 described above unless otherwise described herein. Although aspects of lockout assembly 1100 are described herein as being incorporated into distal retainer 1110, it should be understood that lockout assembly 1100 may be readily incorporated into other portions of end effector 200 in other examples as will be appreciated by those of ordinary skill in the art in view of the teachings herein.

Figure 21:
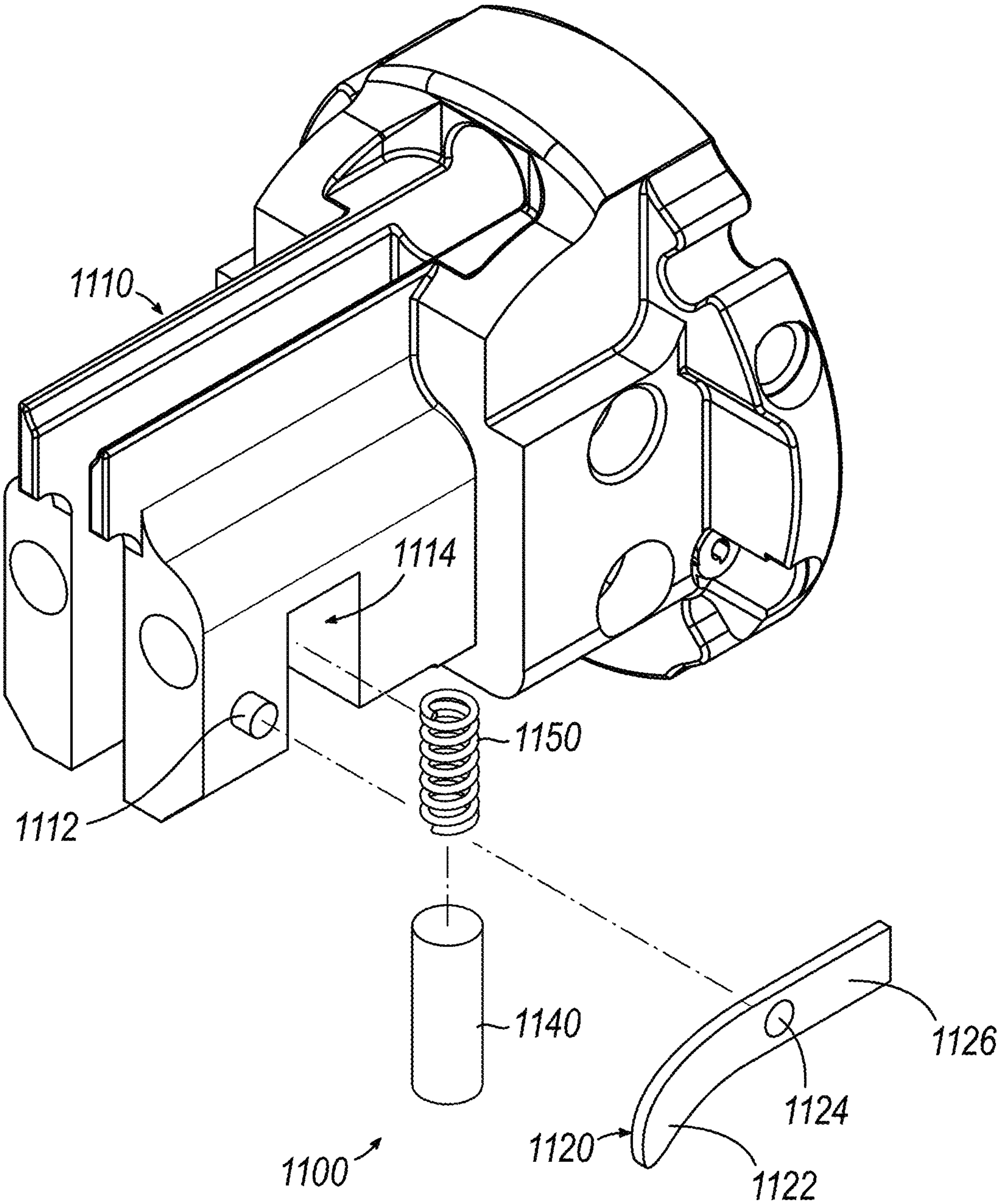
FIG. 21 is an exploded view of the lockout assembly of FIG. 20.
Figure 22:
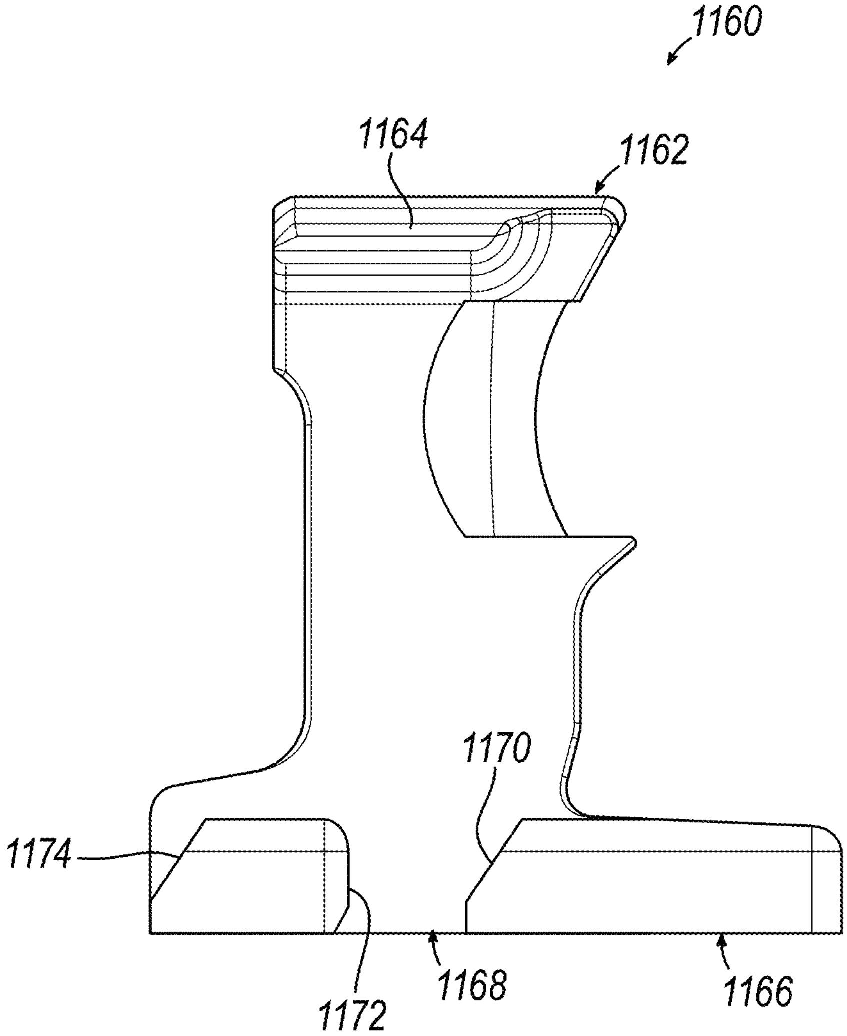
FIG. 22 is a perspective view of a knife for use with the lockout assembly of FIG. 20.

As best seen in FIGS. 20 and 21, lockout assembly 1110 includes a sensor 1120 (also referred to as a sensor element), a lockout 1140 (also referred to as a lockout element), and a basing member 1150. Sensor 1120 is configured to be engaged and/or manipulated by at least a portion of staple cartridge 210, as will be described in greater detail below. It should be understood use of the term "sensor" herein is used to encompass physical sensing mechanisms by one or more components being responsive to the physical presence of one or more other components. Of course, as will be appreciated in view of the teachings herein, sensor 1120 in some examples may additionally, or alternatively, include certain electronic sensing mechanisms.

Sensor 1120 includes an engagement portion 1122, an attachment 1124, and a manipulator 1126. Engagement portion 1122 is configured to extend from a portion of distal retainer 1110 to engage a portion of staple cartridge 210. As will be described in greater detail below, engagement portion 1122 can be driven by the presence of one or more portions of staple cartridge 210 to pivot or otherwise move sensor 1120. To facilitate such a function, engagement portion 1122 can include particular geometric shapes, which may correspond to one or more shapes and/or configurations of one or more portions of staple cartridge 210. For instance, in the present example, engagement portion 1122 is curved downwardly away from a longitudinal axis defined by sensor 1120 to extend toward a predetermined portion of staple cartridge 210. Additionally, a portion of engagement portion 1122 is tapered or necked down to provide a decreased surface area for engagement with one or more portions of staple cartridge 210.

Although engagement portion 1122 of the present example is generally flat or straight in the axial or longitudinal plane, it should be understood that in other examples, engagement portion 1122 can include one or more shaped sections or portions to facilitate engagement with staple cartridge 210 and/or cartridge sled 210A. For instance, in some examples, engagement portion 1122 can include a dog leg section. Such a dog leg section may be desirable to orient one or more features of engagement portion 1122 closer to aspects of staple cartridge 210 such as cartridge sled 210A or components associated therewith such as channels. Of course, various alternative geometric configurations may be used for engagement portion 1122, particularly where the configuration of end effector 200 and/or staple cartridge 210 is varied.

Attachment 1124 is positioned proximate to engagement portion 1122 and is generally configured to movably secure sensor 1120 to distal retainer 1110 or other suitable components of end effector 200. In the present example, attachment 1124 is configured as a bore or other structure extending through sensor 1120, which is configured to receive a corresponding pivot post 1112 extending from distal retainer 1110. Thus, in the present configuration, attachment 1124 is configured to permit a pivoting action of sensor 1120 relative to pivot post 1112 of distal retainer 1110. In other words, attachment 1124 is configured as a fixed pivot that grounds sensor 1120 with respect to distal retainer 1110 and/or other suitable structures such as cartridge jaw 202. Although attachment 1124 of the present example uses a post-bore configuration, it should be understood that in other examples various alternative configurations may be used for attachment 1124.

Manipulator 1126 extends proximally from attachment 1124 and is generally configured to manipulate lockout 1140 in response to movement of engagement portion 1122. Manipulator 1126 of the present example is configured as an elongate rectangular structure. Although not shown, it should be understood manipulator 1126 include a coupling connecting manipulator 1126 to lockout 1140. Such a coupling is generally configured as a movable pivot that can transfer movement of manipulator 1126 to lockout 1140, as will be described in greater detail below. Such a coupling may take on a variety of forms. For instance, in some examples, such a coupling may be in the form of a pivoting linkage similar to attachment 1124. In still other examples, manipulate 1126 can include a driving structure such as a finger or protrusion, while lockout 1140 can include a complementary driven structure such as a flange or protrusion. In such examples, manipulator 1126 may drive lockout 1140 through a pivoting action without being directly coupled to lockout 1140.

As best seen in FIG. 21, lockout 1140 is generally configured to respond to movement of sensor 1120 to selectively lock, interfere, block, or otherwise impede movement of a knife 1160 relative to distal retainer 1110. Lockout 1140 of the present example is generally configured as a cylindrical post or bollard. As described above, lockout 1140 is coupled to manipulator 1126 such that manipulator 1126 can drive lockout 1140 along a longitudinal axis defined by lockout 1140. In other words, lockout 1140 is vertically constrained with respect to distal retainer 1110 or other suitable portions of end effector 2000 such as cartridge jaw 202.

Lockout 1140 is generally disposed within a channel 1114 defined by distal retainer 1110. Thus, in the present example, channel 1114 is configured to vertically constrain lockout 1140 for movement along an axis defined by channel 1114. Meanwhile, sensor 1120 is laterally offset with respect to lockout 1140 and is thus positioned outside channel 1114. Channel 1114 is generally oriented perpendicularly relative to a longitudinal axis defined by distal retainer 1110. Consequently, lockout 1140 is configured to move axially, or translate, within channel 1114, also perpendicularly relative to the longitudinal axis defined by distal retainer 1110. Additionally, by being disposed within channel 1114, lockout 1140 is grounded along the length of distal retainer 1110. In other words, lockout 1140 is movable within channel 1114 vertically, but fixed within channel 1114 horizontally.

Biasing member 1150 is also generally disposed within channel 1114 between lockout 1140 and a portion of distal retainer 1110. Thus, biasing member 1150 is generally configured to bias lockout 1140 outwardly with respect to channel 1114 or downwardly. In the present example, biasing member 1150 includes a spring such as a coil spring. In other examples, biasing member 1150 can include a variety of other features configured to resiliently bias lockout 1140 away from a portion of distal retainer 1110.

Although biasing member 1150 is shown in the present example as being configured to engage a top portion of lockout 1140, it should be understood that in other examples, biasing member 1150 can be received in at least a portion of lockout 1140. For instance, in some examples, lockout 1140 can include a bore configured to receive a portion of biasing member 1150 with another portion of biasing member 1150 protruding from lockout 1140 to engage distal retainer 1110. In such configurations, lockout 1140 may be configured to retain or guide biasing member 1150.

In some examples, lockout 1140 can be configured to engage directly with knife 206 to prevent or otherwise impede proximal movement of knife 206. For instance, lockout 1140 may be driven downwardly in a proximal position relative to lower knife tab 246 to block or otherwise impede proximal movement of knife 206.

In other examples, it may be desirable to incorporate a modified version of knife 206 configured specifically for use with lockout assembly 1110. For instance, FIG. 23 depicts an alternative knife 1160 configured for use with lockout assembly 1110 in lieu of knife 206 described above. Knife 1160 of the present example is substantially similar to knife 206 described above except where otherwise described herein. Like knife 206 described above, knife 1160 of the present example includes a knife sled 1162 having an upper knife tab 1164 and a lower knife tab 1166. As similarly described above, tabs 1164, 1166 are configured to guide knife 1160 during advancement relative to end effector 200.

Unlike knife 206 described above, knife 1160 of the present example includes features to promote engagement with lockout assembly 1100. In particular, lower knife tab 1166 defines a lock recess 1168 disposed therein. As will be described in greater detail below, lock recess 1168 is generally configured to receive a portion of lockout 1140 to promote engagement between knife 1160 and lockout 1140. Thus, lock recess 1168 is generally complementary in shape and size relative to lockout 1140 so that a portion of lockout 1140) can be received therein.

To further facilitate engagement with lockout assembly 1100, lower knife tab 1166 includes one or more ramps 1170, 1174 and one or more engagement faces 1172. For instance, in the present example, lower knife tab 1166 defines a distal ramp 1170 on a distal side of lock recess 1168 and an engagement face 1172 on a proximal side of lock recess 1168. Additionally, lower knife tab 1166 further defines a proximal ramp 1170 at a proximal end of lower knife tab 1166. As will be described in greater detail below, distal ramp 1170 and proximal ramp 1174 are configured to guide lockout 1140 upwardly during some stages of operation during proximal retraction of knife 1160. Meanwhile, engagement face 1172 defines a generally flat face configured to engage lockout 1140 and thereby prevent distal movement of knife 1160. Although ramps 1170, 1174 are shown as having a particular angle in the present example, it should be understood that other suitable angles may be used in other examples.

Figure 23A:
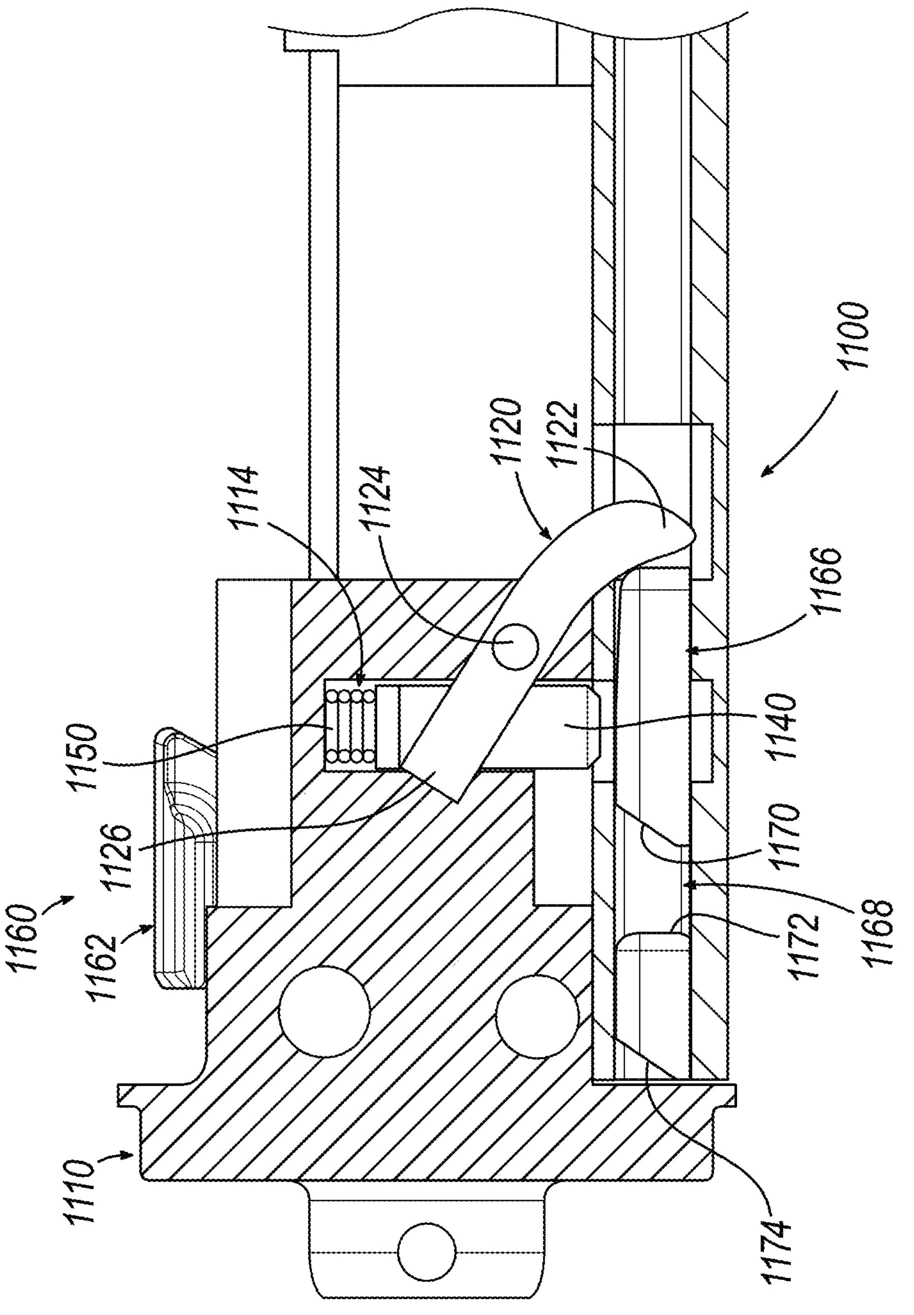
FIG. 23A is a side cross-sectional view of the lockout assembly of FIG. 20 in use with the surgical instrument of FIG. 1, the lockout assembly in an initial unlocked condition.
Figure 23B:
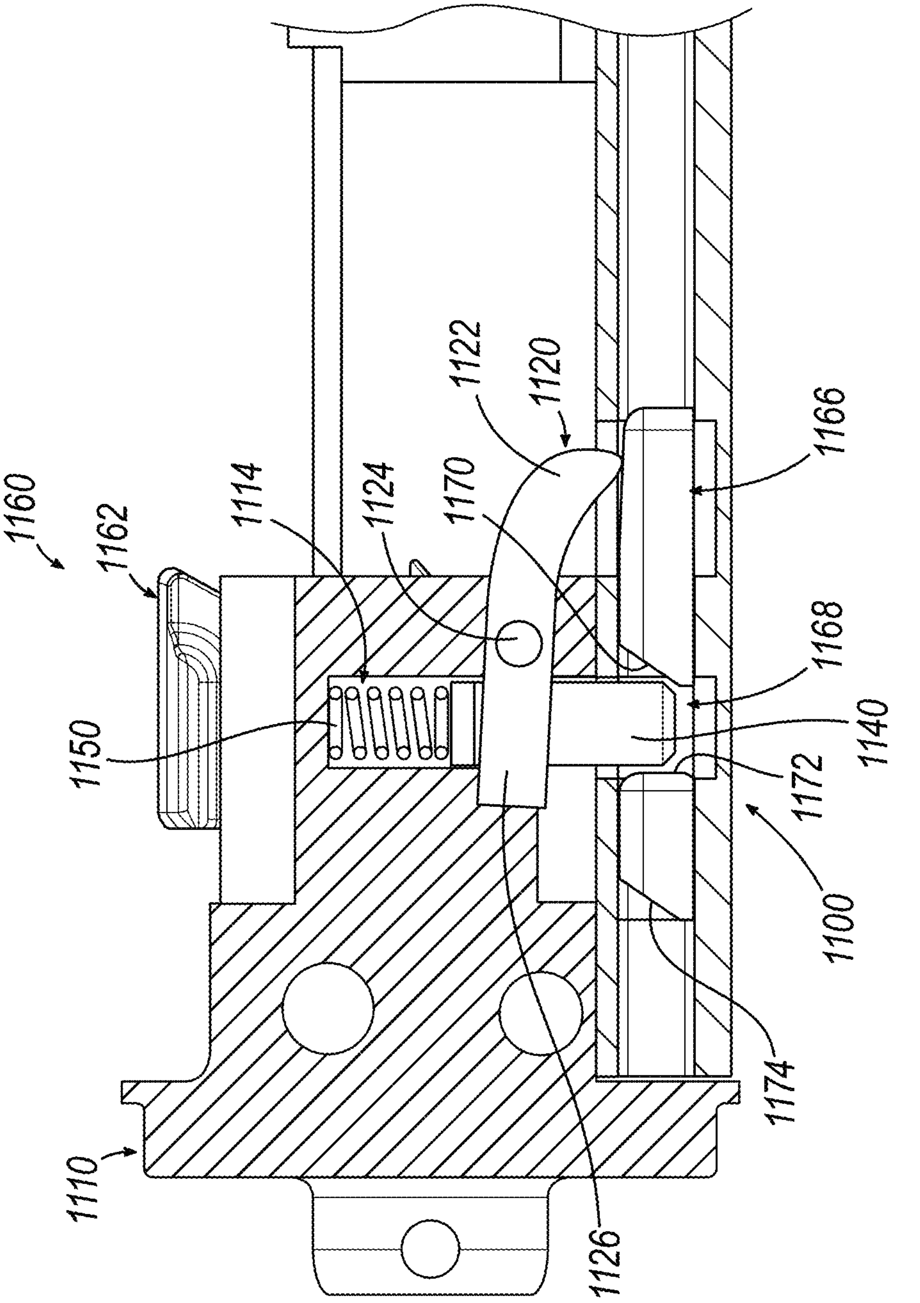
FIG. 23B is another side cross-sectional view of the lockout assembly of FIG. 20 in use with the surgical instrument of FIG. 1, the lockout assembly in a locked condition.
Figure 23C:
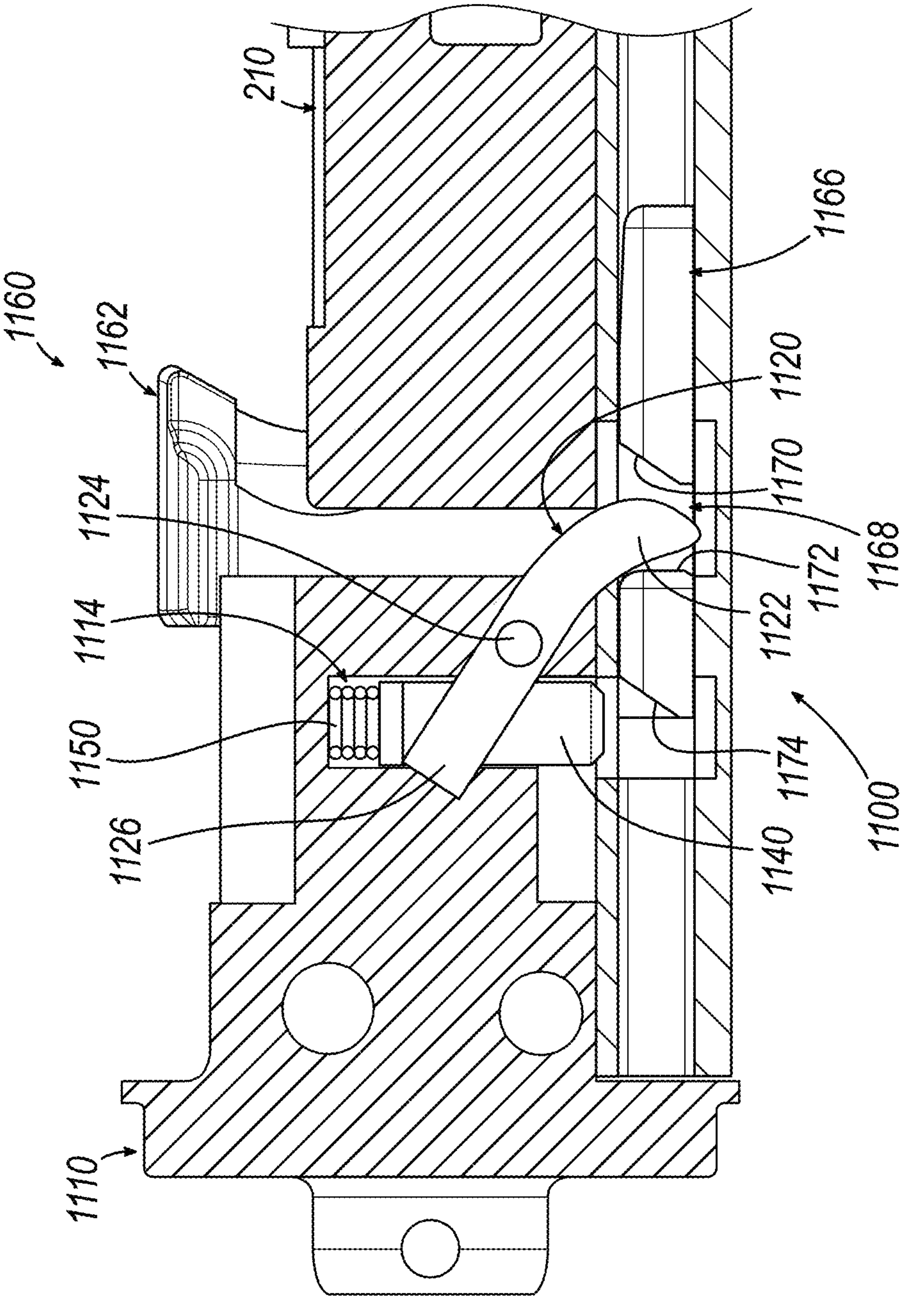
FIG. 23C is yet another side cross-sectional view of the lockout assembly of FIG. 20 in use with the surgical instrument of FIG. 1, the lockout assembly in the unlocked condition.

FIGS. 23A through 23C depict an illustrative use of lockout assembly 1100 to selectively lock distal movement of knife 1160 in certain predetermined conditions. As best seen in FIG. 23A, lockout assembly 1100 may begin in an initial unlocked position. This initial position may correspond to a condition prior to use of end effector 200. In such a condition, staple cartridge 210 is not yet inserted into end effector 200. Additionally, knife 1160 may be in an initial or home position. In this initial position, knife 1160 is disposed in its proximal-most position relative to distal retainer 1110.

With knife 1160 disposed in its proximal-most position relative to distal retainer 1110, lockout 1140 of lockout assembly 1100 rests on top of lower knife tab 1166 against the resilient bias provided by biasing member 1150. This positions lockout assembly 1100 in an unlocked position with lockout 1140 in an upward or recessed position relative to distal retainer 1110. Due to the linkage between lockout 1140 and sensor 1120, sensor 1120 is positioned with engagement portion 1122 positioned downwardly and manipulator 1126 positioned upwardly. In the present use, this also corresponds to the movable pivot between lockout 1140 and sensor 1120 being positioned above the fixed pivot between sensor 1120 and distal retainer 1110.

Once one or more operational conditions of end effector 200 are met, lockout assembly 1100 may move from the initial unlocked position described above into a locked position. As best seen in FIG. 23B, the locked position may correspond to a condition where end effector 200 remains in an absent-cartridge condition with staple cartridge 210 not disposed within end effector 200. Without the presence of staple cartridge 210, sensor 1120 is free to travel within end effector 200 subject to any forces applied by lockout 1140. Thus, upon distal movement of knife 1160, lockout 1140 may move from resting on lower knife tab 1166 to resting within lock recess 1168. As a result, lockout 1140 can translate downwardly relative to distal retainer 1110 and into lock recess 1168 of knife 1160 under the resilient bias provided by biasing member 1150. Lockout 1140 can then engage engagement face 1172 of knife 1160 preventing further distal movement of knife 1160.

As described above, sensor 1120 is generally free to travel within end effector 200 subject to any forces applied by lockout 1140. This is due to engagement portion 1122 being unrestricted by any portion of end effector 200. Thus, as lockout 1140 translates downwardly relative to distal retainer 1110, manipulator 1126 is likewise driven downwardly. This moves the movable pivot coupling lockout 1140 and sensor 1120 downwardly into substantial alignment with the fixed pivot between sensor 1120 and distal retainer 1110. As a result of this downward movement of manipulator 1126, engagement portion 1122 moves upwardly or in an opposite direction relative to manipulator 1126.

Under some circumstances, lockout assembly 1100 can be forced into the unlocked position using sensor 1120. For instance, as best seen in FIG. 23C, the presence of staple cartridge 210 within end effector 200 can act to force lockout assembly 1100 into the unlocked position. As can be seen, staple cartridge 210 may engage engagement portion 1122 of sensor 1120. As a consequence of this engagement, engagement portion 1122 may be driven downwardly, while manipulator 1126 may be driven in an opposite, upward, direction. Due to the linkage between sensor 1120 and lockout 1140, lockout 1140 can also be driven upwardly into channel 1114 of distal retainer 1110 against the resilient bias of biasing member 1150. Thus, upward movement of lockout 1140 withdraws lockout 1140 from lock recess 1168 of knife 1160, thereby permitting distal movement of knife 1160.

It should be understood that sensor 1120 can be configured to engage a variety of structures of staple cartridge 210 to force lockout assembly 1110 into the unlocked position. For instance, in some configurations, engagement portion 1122 of sensor 1120 is configured to engage cartridge sled 210A of staple cartridge 210 specifically rather than a general structure of staple cartridge 210. This configuration may be desirable in some uses to provide locking from lockout assembly 1100 in both spent-cartridge conditions and absent-cartridge conditions. Specifically, by configuring engagement portion 1122 to engage cartridge sled 210A, the unlocked position will only be forced when both staple cartridge 210 is present and cartridge sled 210A is in an initial proximal position. In such uses, it should be understood that staple cartridge 210 and/or cartridge sled 210A may include one or more features to facilitate such engagement such as channels, protrusions, and/or etc.

In the present example, the locking action provided by lockout assembly 1110 is generally in the form of a hard stop. However, it should be understood that in other examples, lockout assembly 1110 may be configured to provide only a partial or soft stop. Such partial or soft stops may be configured to only impede or apply a resistive force to movement of knife 1160, but not completely resist movement of knife 1160. This configuration may be desirable in circumstances where advancement of knife 1160 is robotically or electronically controlled, thus permitting precise detection of the advancement forces applied to knife 1160. With such precise detection, a predetermined force applied by lockout assembly 1110 can be identified and then full lockout of movement of knife 1160 can be facilitated through software or electronic control algorithms, providing increased flexibility over mechanically driven lockout configurations.

B. Illustrative Alternative Lockout Assembly with Spring Sensor

Figure 24:
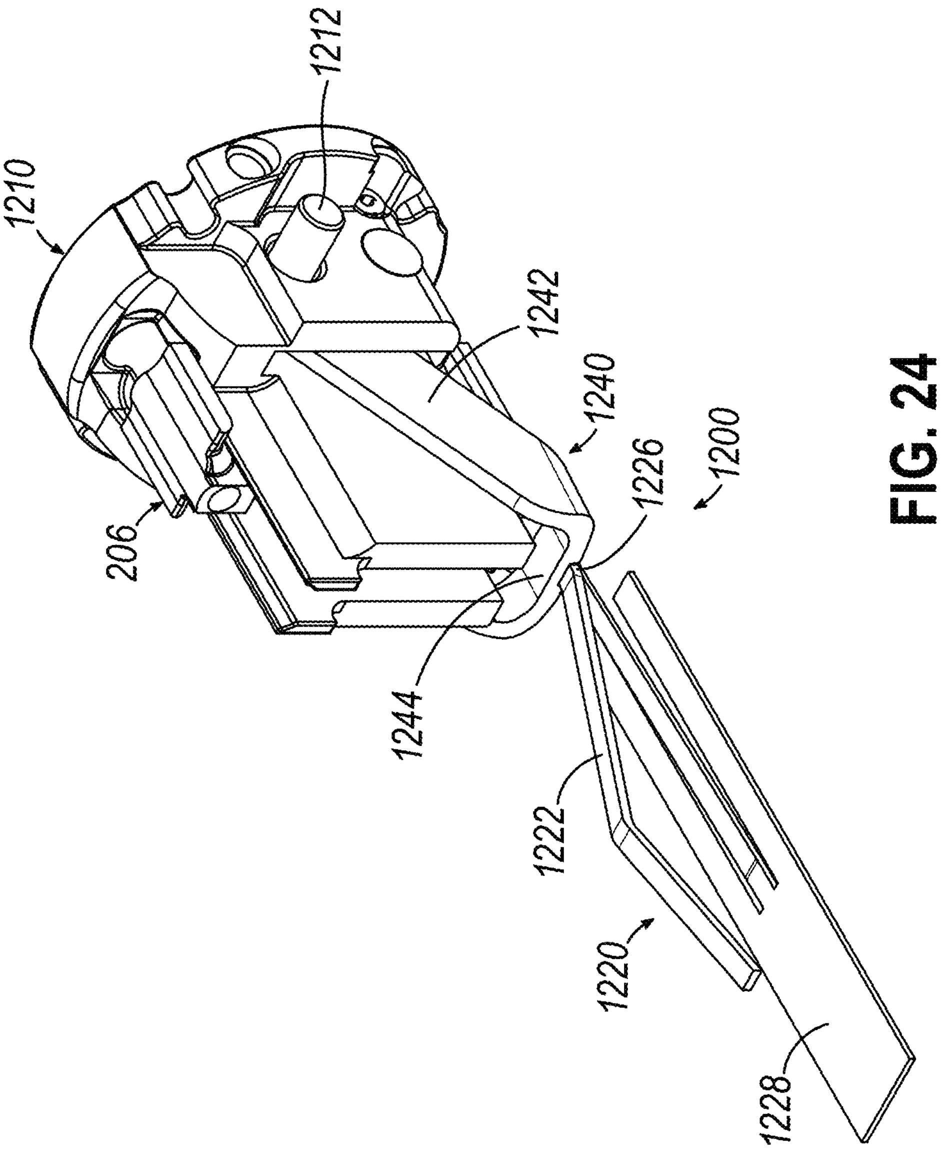
FIG. 24 is a perspective view of an illustrative alternative lockout assembly that may be readily incorporated into the end effector of the surgical instrument of FIG. 1.

FIG. 24 depicts a lockout assembly 1200, which may be readily incorporated into end effector 200 of surgical instrument 1000 described above. For instance, in the present example, lockout assembly 1200 is incorporated into a portion of a distal retainer 1210, which may be incorporated into end effector 200 in lieu of distal retainers 324, 1110 described above. It should be understood that distal retainer 1210 of the present example is substantially similar to distal retainer 324 described above unless otherwise described herein. Although aspects of lockout assembly 1200 are described herein as being incorporated into distal retainer 1210, it should be understood that lockout assembly 1200 may be readily incorporated into other portions of end effector 200 in other examples as will be appreciated by those of ordinary skill in the art in view of the teachings herein.

Lockout assembly 1210 of the present example includes a sensor 1220 (also referred to as a sensor element), and a lockout 1240 (also referred to as a lockout element). Sensor 1220 is configured to be engaged and/or manipulated by at least a portion of staple cartridge 210, as will be described in greater detail below. It should be understood use of the term "sensor" herein is used to encompass physical sensing mechanisms by one or more components being responsive to the physical presence of one or more other components. Of course, as will be appreciated in view of the teachings herein, sensor 1120 in some examples may additionally, or alternatively, include certain electronic sensing mechanisms.

Sensor 1220 includes an engagement portion 1222, a manipulator 1226, and a base 1228. In the present example, engagement portion 1222, manipulator 1226, and base 1228 are all of integral construction, although in other examples any one or more of engagement portion 1222, manipulator 1226, or base 1228 may be separate from each other. Engagement portion 1222 and manipulator 1226 are together formed of a single contiguous piece of material first extending upwardly from base 1228 and then looping around back to base 1222. In this configuration, engagement portion 1222 and manipulator 1226 together form a resilient member similar to a leaf spring shepherd's crook flat spring. Thus, it should be understood that engagement portion 1222, manipulator 1227 or both are generally of a rigid, yet flexible, material.

As will be described in greater detail below, engagement portion 1222 is configured to be driven by the presence of one or more portions of staple cartridge 210 to bend, pivot, or otherwise move at least a portion of sensor 1220. To facilitate such a function, engagement portion 1222 can define various particular geometric shapes, which may correspond to one or more shapes and/or configurations of one or more portions of staple cartridge 210. For instance, in the present example, engagement portion 1222 is curved upwardly away from a flat surface defined by base 1228 to define a peak or apex configured to engage a predetermined portion of staple cartridge 210. Of course, various alternative geometric configurations may be used for engagement portion 1222, particularly where the configuration of end effector 200 and/or staple cartridge 210 is varied.

Manipulator 1226 extends proximally from engagement portion 1222 and base 1228 and is generally configured to manipulate lockout 1240 in response to movement of engagement portion 1222. Manipulator 1226 of the present example is configured with a generally triangular or nose shape with the vertex of the triangular shape being configured to engage lockout 1240.

Optionally, in some examples, manipulator 1226 can define an opening, recess, indentation, fork, or other structure configured to receive a portion of lockout 1240. For instance, in some examples, the structure forming the vertex of the triangular shape of manipulator 1224 may continue after the vertex to form two outwardly extending protrusions. Such protrusions may engage a portion of lockout 1240 to locate manipulator 1226 relative to lockout 1240 or otherwise maintain engagement between manipulator 1226 and a predetermined portion of lockout 1240.

Base 1228 is a generally rectangular flat plate oriented below at least a portion of engagement portion 1222 and/or manipulator 1226. In the present example, base 1228 is configured to engage a portion of end effector 200 to ground engagement portion 1222 and manipulator 1226 relative to distal retainer 1210. By way of example only, in some examples, base 1228 is attached to a portion of cartridge jaw 202 within elongated channel 208 proximally of distal retainer 1210. Of course, in other examples, base 1228 can be attached to a variety of other structures of end effector (200).

Due to the integral construction of sensor 1220, at least a portion of engagement portion 1222 and/or manipulator 1226 are cutout from a portion of base 1228 to form the structures of base 1228, engagement portion 1222 and manipulator 1226 from a single piece of material. In some examples, this configuration may be desirable for ease of manufacturability. For instance, engagement portion 1222, manipulator 1226, and base 1228 may be initially formed of a single flat blank with a cutout portion for engagement portion 1222 and manipulator 1226. The cutout portion may then be bent relative to base 1228 to form the particular shapes of engagement portion 1222 and manipulator 1226, respectively. Of course, in other examples, engagement portion 1222 and/or manipulator 1226 may be formed of discrete parts secured or fastened to base 1228.

Lockout 1240 is generally configured to respond to movement of sensor 1220 to selectively lock or otherwise impede movement of knife 206, 1160 relative to distal retainer 1210. Lockout 1240 of the present example includes a pair of arms 1242 and a brake 1244 extending between respective distal ends of each arm 1242. Generally, arms 1242 are pivotable relative to distal retainer 1210 to move brake 1244 relative to knife 206, 1160 to selectively lock and unlock proximal movement of knife 206, 1160. In the present example, arms 1242 and brake 1244 are of integral construction. However, as discussed in greater detail below, in other examples arms 1242 and brake 1244 can be configured as separate discrete elements coupled together.

Each arm 1242 extends distally way from a portion of distal retainer 1210. A proximal end of each arm 1242 is pivotably secured to a portion of distal retainer 1210. In particular, distal retainer 1210 includes a pivot post 1212, which is configured to secure each arm 1242 to distal retainer 1210, while permitting at least some pivoting movement of each arm 1242 relative to distal retainer 1210. Optionally, distal retainer 1210 can define a channel 1214 corresponding to each arm 1242 and configured to receive at least a portion of each arm 1242 within the structure of distal retainer 1210. As can be seen, in the present example, pivot post 1212 extends through channels 1214 to permit coupling between distal retainer 1210 and arms 1242.

Arms 1242 are generally spaced from each other about the width of distal retainer 1210. The space between arms 1242 is generally set to provide clearance for other structures of distal retainer 1210. Thus, in other examples, different spacing between arms 1242 may be used. In such examples, spacing between arms 1242 may be defined by the width of knife 206, 1160. As will be described in greater detail below, such spacing may be desirable to permit knife 206, 1160 to pass between arms 1242 without arms 1242 directly impeding motion of knife 206, 1160.

As described above, brake 1244 extends between a respective distal end of each arm 1242. Brake 1244 generally extends horizontally between arms 1242 to provide a barrier to block movement of knife 206, 1160 in some positions, and permit movement of knife 206, 1160 in other positions. Thus, brake 1244 in the present example defines a generally rectangular cross-section. However, as will be described in greater detail below, the particular shape of brake 1244 may be varied in other examples. Due to the integral construction described above, brake 1244 is generally formed by each arm 1242 being twisted or bent from an axial orientation to a transverse orientation. In other words, arms 1242 and brake 1244 together form a generally D-shaped or C-shaped configuration.

Although not shown, it should be understood that in some examples, brake 1244 may include one or more receiving features configured to receive a portion of sensor 1220. For instance, as described above, manipulator 1226 may optionally define an opening, recess, indentation, fork, or other structure configured to receive a portion of brake 1244. In such examples, brake 1244 may likewise include a complementary feature such as a channel, recess, indentation, or the like to receive manipulator 1226. Alternatively, even where manipulator 1226 lacks such features, brake 1244 may still include one or more features complementary to manipulator 1226 to locate manipulator 1226 relative to brake 1244.

Figure 25A:
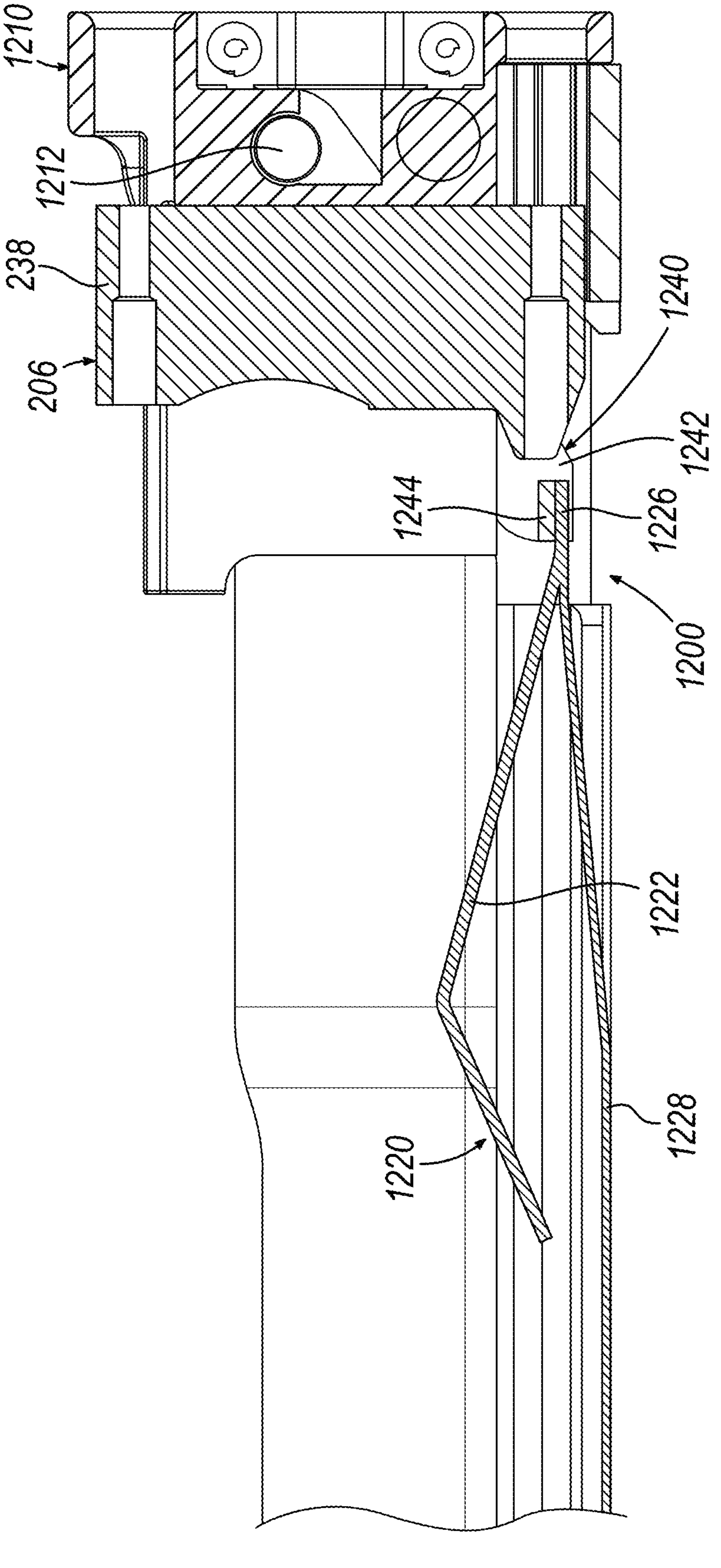
FIG. 25A is a side cross-sectional view of the lockout assembly of FIG. 24 in use with the surgical instrument of FIG. 1, the lockout assembly in a locked condition.
Figure 25B:
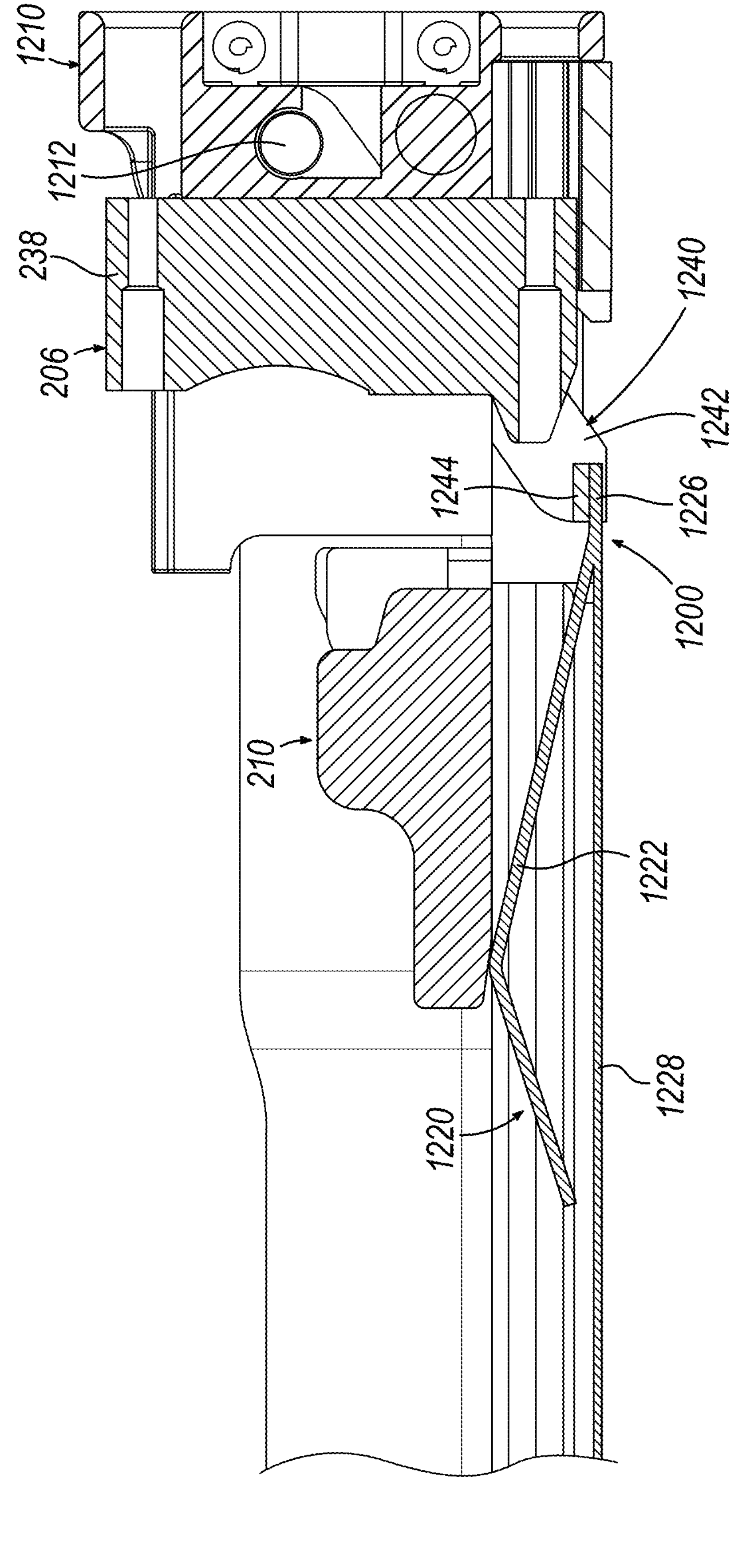
FIG. 25B is another side cross-sectional view of the lockout assembly of FIG. 24 in use with the surgical instrument of FIG. 1, the lockout assembly in an unlocked condition.

FIGS. 25A through 25B show an illustrative use of lockout assembly 1200 in combination with end effector 200 to selectively prevent proximal movement of knife 206 in certain circumstances. In the present use, lockout assembly 1200 is shown in combination with knife 206. However, it should be understood that in other uses, lockout assembly 1200 may be readily used with any other knives described herein such as knife 1160 described above.

Figure 26A:
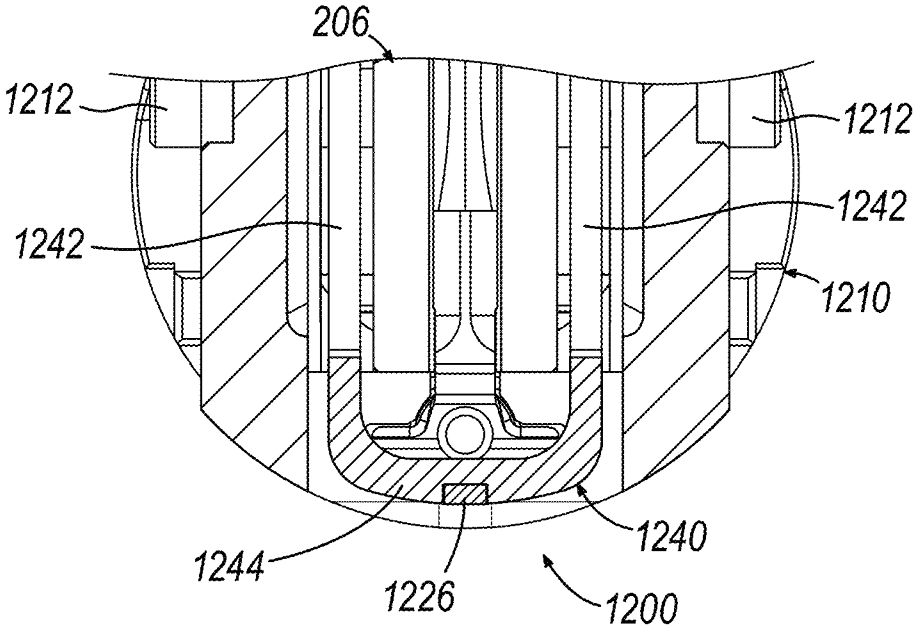
FIG. 26A is a front cross-sectional view of the lockout assembly of FIG. 24 in use with the surgical instrument of FIG. 1, the lockout assembly in the locked condition.

FIGS. 25A and 26A show lockout assembly 1200 in an initial locked condition. This locked condition may correspond to end effector being in a absent-cartridge condition where staple cartridge 210 is not disposed within end effector 200. As can be seen, in the absence of staple cartridge 210, engagement portion 1222 is freely movable within end effector 200. Due to the resilient bias provided by the combination of engagement portion 1222 and manipulator 1226, both engagement portion 1222 and manipulator 1226 can move upwardly relative to base 1228 and distal retainer 1210. As a result, manipulator 1226 can engage brake 1244 of lockout 1240 to pivot brake 1244 and arms 1242 upwardly relative to distal retainer 1210. This then positions brake 1244 within the distal travel path of knife 206, therefore preventing distal movement of knife 206.

Figure 26B:
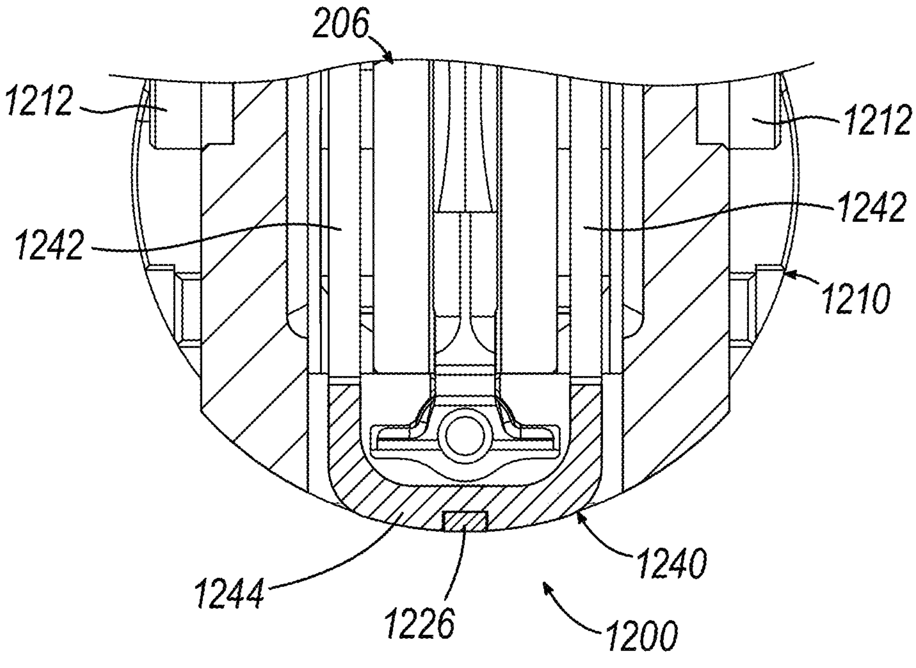
FIG. 26B is another front cross-sectional view of the lockout assembly of FIG. 24 in use with the surgical instrument of FIG. 1, the lockout assembly in the unlocked condition.

After staple cartridge 210 is positioned within end effector 200, lock assembly 1200 can be transitioned into an unlocked configuration. As best seen in FIGS. 25B and 26B, when staple cartridge 210 is inserted into end effector 200, a portion of staple cartridge 210 can engage engagement portion 1222 of sensor 1220, driving engagement portion 1222 downwardly relative to base 1228 and distal retainer 1210. As a result, manipulator 1226 is likewise moved downwardly relative to base 1228 and distal retainer 1210. As manipulator 1226 moves downwardly, brake 1244 of lockout 1240 is also permitted to move downwardly with arms 1242 pivoting relative to distal retainer 1210. This movement positions brake 1244 outside of the distal travel path of knife 206, therefore permitting distal movement of knife 206.

It should be understood that sensor 1220 can be configured to engage a variety of structures of staple cartridge 210 to force lockout assembly 1210 into the unlocked condition described above. For instance, in some configurations, engagement portion 1222 of sensor 1220 is configured to engage cartridge sled 210A of staple cartridge 210 specifically rather than a general structure of staple cartridge 210. This configuration may be desirable in some uses to provide locking from lockout assembly 1200 in both spent-cartridge conditions and absent-cartridge conditions. Specifically, by configuring engagement portion 1222 to engage cartridge sled 210A, the unlocked condition will only be forced when both staple cartridge 210 is present and cartridge sled 210A is in an initial proximal position. In such uses, it should be understood that staple cartridge 210 and/or cartridge sled 210A may include one or more features to facilitate such engagement such as channels, protrusions, and/or etc.

Figure 27:
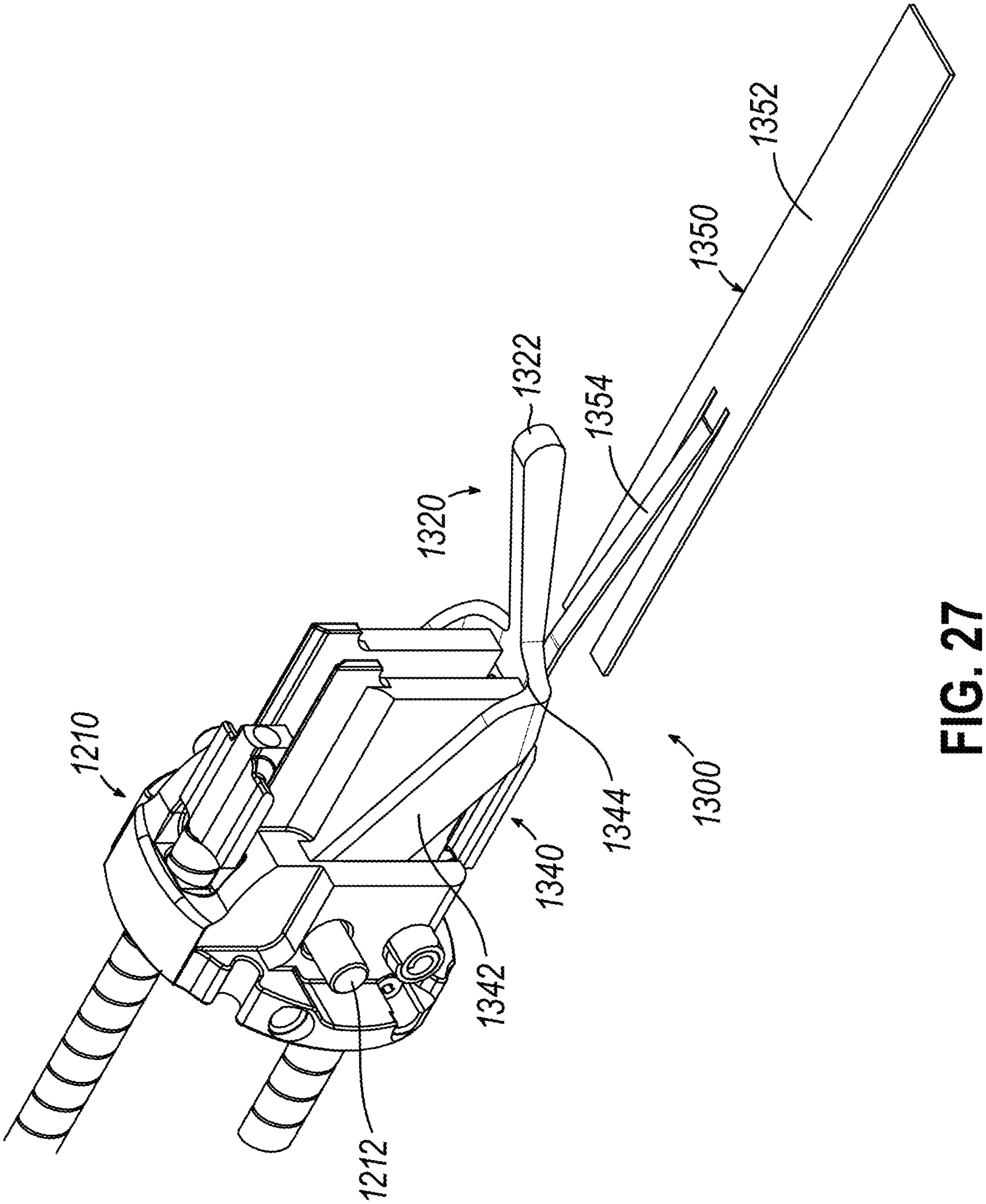
FIG. 27 is a perspective view of another illustrative alternative lockout assembly that may be readily incorporated into the end effector of the surgical instrument of FIG. 1.

In some examples, of lockout assembly 1200 described above, it may be desirable to combine certain elements of sensor 1220 and lockout 1240 into a single component. For instance, FIG. 27 shows an alternative lockout assembly 1300 that is substantially similar to lockout assembly 1200 except where as otherwise described herein.

Like lockout assembly 1200 described above, lockout assembly 1300 of the present example includes a sensor 1320 (also referred to as a sensor element), and a lockout 1340 (also referred to as a lockout element). As with sensor 1220 described above, sensor 1320 of the present example is configured to be engaged and/or manipulated by at least a portion of staple cartridge 210. However, as will be described in greater detail below, unlike sensor 1220 described above, sensor 1320 of the present example is integrated into a portion of lockout 1340 instead of being a separate component, as will be described in greater detail below.

Lockout 1340 is generally substantially similar to lockout 1240 described above. For instance, lockout 1340 of the present example is generally configured to respond to movement of sensor 1320 to selectively lock or otherwise impede movement of knife 206, 1160 relative to distal retainer 1210. As similarly described above, lockout 1340 of the present example includes a pair of arms 1342 and a brake 1344 extending between respective distal ends of each arm 1342. As with arms 1242 described above, arms 1342 are generally pivotable relative to distal retainer 1210 to move brake 1344 relative to knife 206, 1160 to selectively lock and unlock proximal movement of knife 206, 1160. In the present example, arms 1342 and brake 1344 are of integral construction. However, in other examples arms 1342 and brake 1344 can be configured as separate discrete elements coupled together.

As with each arm 1242 described above, each arm 1242 of the present example extends proximally away from a portion of distal retainer 1210. A proximal end of each arm 1342 is pivotably secured to a portion of distal retainer 1210. In particular, pivot post 1212 of distal retainer 1210 is configured to secure each arm 1342 to distal retainer 1210, while permitting at least some pivoting movement of each arm 1242 relative to distal retainer 1210 as similarly described above.

Like brake 1244 described above, brake 1344 of the present example extends between a respective distal end of each arm 1342. Brake 1344 generally extends horizontally between arms 1342 to provide a barrier to block movement of knife 206, 1160 in some positions, and permit movement of knife 206, 1160 in other positions. Thus, brake 1344 in the present example defines a generally rectangular cross-section like brake 1244 described above.

Unlike brake 1244 described above, brake 1344 of the present example includes features similar to sensor 1220 described above. In particular, engagement portion 1322 of the present example extends from brake 1344 to define sensor 1320. In the present configuration, engagement portion 1322 is integral with brake 1344 and extends at an angle relative to the upper surface of brake 1344. In this configuration, engagement portion 1322 is configured to penetrate a portion of staple cartridge 210 to engage cartridge sled 210A. Thus, unlike sensor 1220 described above, sensor 1320 of the present example omits structures similar to manipulator 1226, with engagement portion 1322 instead being directly incorporated into lockout 1340.

Lockout assembly 1300 of the present example further includes a separate biasing member 1350 to replicate the biasing functionality of engagement portion 1222 and manipulator 1226 described above. In particular, biasing member 1350 includes a base 1352 similar to base 1228 described above and a resiliently biased arm 1354 extending upwardly from base 1352. Similarly to base 1228 described above, base 1352 of the present example is configured to ground biasing member 1350 relative to end effector 200 and may be secured or attached to features of end effector 200 such as cartridge jaw 202. Meanwhile, resiliently biased arm 1354 is configured to engage brake 1344 and/or engagement portion 1322 to bias the combination of brake 1344 and engagement portion 1322 upwardly toward the locked condition.

Although a separate biasing member 1350 is used in the present example, it should be understood that in other examples, a portion of biasing member 1350 may be integrated into lockout 1340 and/or distal retainer 1210. For instance, in some examples, one or more springs may be integrated into arms 1342 to bias arms toward the upward locked condition. In addition, or in the alternative, such springs may be integrated into pivot post 1212, channels 1214, or both.

In use, it should be understood lockout assembly 1300 is used substantially similarly to lockout assembly 1200 described above. In particular, during the spent-cartridge condition or absent-cartridge condition, engagement portion 1322 is generally free to move within end effector 200. Thus, biasing member 1350 may act to drive engagement portion 1322 and brake 1344 upwardly toward the locked condition, thereby blocking the distal travel path of knife 206. However, when staple cartridge 210 is present in the unspent condition, cartridge sled 210A may engage engagement portion 1322 driving engagement portion 1322 and brake 1344 downwardly out of the distal travel path of knife 206.

C. Illustrative Alternative Lockout Assembly with Rod Spring

Figure 28:
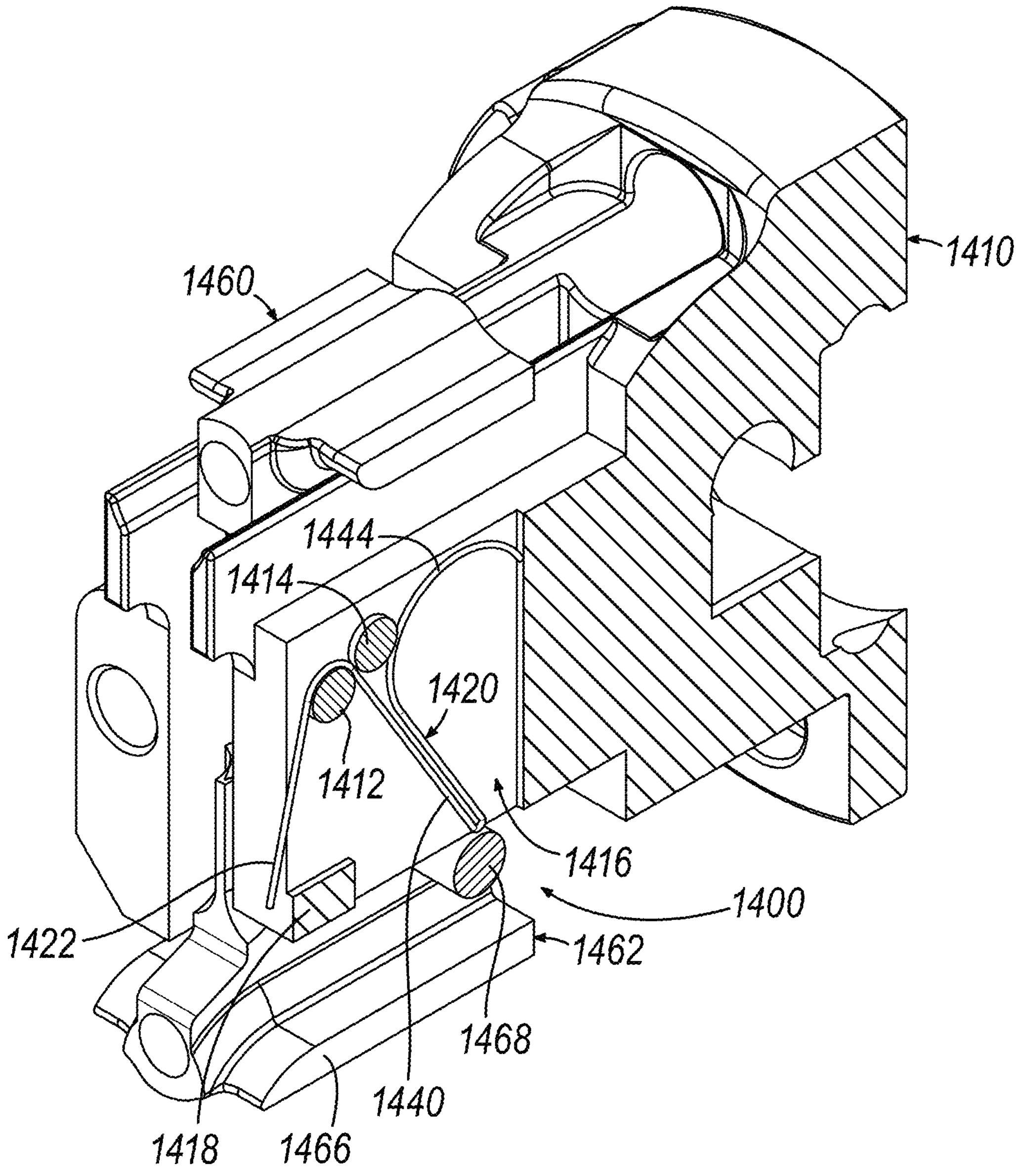
FIG. 28 is a perspective partial cross-sectional view of yet another illustrative alternative lockout assembly that may be readily incorporated into the end effector of the surgical instrument of FIG. 1.

FIG. 28 depicts a lockout assembly 1400, which may be readily incorporated into end effector 200 of surgical instrument 1000 described above. For instance, in the present example, lockout assembly 1400 is incorporated into a portion of a distal retainer 1410, which may be incorporated into end effector 200 in lieu of distal retainers 324, 1110, 1210 described above. It should be understood that distal retainer 1410 of the present example is substantially similar to distal retainer 324 described above unless otherwise described herein. Although aspects of lockout assembly 1400 are described herein as being incorporated into distal retainer 1410, it should be understood that lockout assembly 1400 may be readily incorporated into other portions of end effector 200 in other examples as will be appreciated by those of ordinary skill in the art in view of the teachings herein.

Lockout assembly 1410 of the present example includes a sensor 1420 (also referred to as a sensor element), and a lockout 1440 (also referred to as a lockout element). Sensor 1420 is configured to be engaged and/or manipulated by at least a portion of staple cartridge 210, as will be described in greater detail below. It should be understood use of the term "sensor" herein is used to encompass physical sensing mechanisms by one or more components being responsive to the physical presence of one or more other components. Of course, as will be appreciated in view of the teachings herein, sensor 1420 in some examples may additionally, or alternatively, include certain electronic sensing mechanisms.

In the present example, sensor 1420 and lockout 1440 are combined into a unitary element formed of a single piece of rod, with the rod being bent at certain locations to define elements of sensor 1420 and lockout 1440. Although the structure used here is described as being a "rod" structure, it should be understood that in other examples other suitable structures may be used such as bar or beam structures.

Sensor 1420 includes an engagement portion 1422 extending distally relative to distal retainer 1410. As will be described in greater detail below, engagement portion 1422 is generally configured to engage a portion of staple cartridge 210. Thus, the particular shape of engagement portion 1422 may be configured to engage a particular portion of staple cartridge 210. In the present example, engagement portion 1422 is defined by a straight section of rod oriented at a downwardly sloping angle. The downwardly sloping angle may be desirable in some examples to promote engagement with staple cartridge 210, while avoiding impedance of insertion of staple cartridge 210 due to binding with engagement portion 1422.

Engagement portion 1422 extends from a lower locator pin 1412 and an upper locator pin 1414 of distal retainer 1410. Proximate lower locator pin 1412, the rod forming engagement portion 1422 bends to transition into lockout 1440. In particular, the rod bends downwardly from lower locator pin 1412 toward the bottom of distal retainer 1410 and then bends about 180° to return upwardly in the vertical direction. This forms two parallel runs of rod, which define lockout 1440. As will be described in greater detail below, lockout 1440 is configured to engage a portion of a knife 1460 to lock knife 1460 based on a condition of engagement portion 1422 of sensor 1420.

Lockout assembly 1400 further includes a counterbalance 1444 extending proximally from lockout 1440. Counterbalance 1444 has a generally curved shape. The particular extension of counterbalance 1444 may have a predetermined relationship with other elements of lockout assembly 1440 such as engagement portion 1422. For instance, counterbalance 1444 is generally configured to balance the weight distribution of lockout assembly 1400 such that lockout 1440 will be positioned vertically when at rest on lower locator pin 1412. Thus, in some examples, counterbalance 1444 may define an extension similar to the extension of engagement portion 1422. Additionally, or in the alternative, in some examples, counterbalance 1444 is configured as a spring or resilient member. Such a configuration may be desirable to promote engagement between engagement portion 1422 and one or more portions of staple cartridge 210. In such examples, counterbalance 1444 may engage a portion of distal retainer 1410, thereby driving engagement portion 1422 distally.

Unlike other distal retainers 324, 1110, 1210 described above, distal retainer 1410 of the present example includes certain features to facilitate interaction with lockout assembly 1400. In particular, distal retainer 1410 defines a lockout channel 1416 and a hard stop 1418 disposed in a lower distal portion of lockout channel 1416. Lockout channel 1416 defines a width at least as wide as the width of the rod of lockout assembly 1400, although may be wider in some examples. Lockout channel 1416 is generally sized to house one or more portions of lockout assembly 1400 such as counterbalance 1444, a portion of lockout 1440 and a portion of engagement portion 1422 of sensor 1420. As will be described in greater detail below, lockout channel 1416 is further configured for one or more portions of lockout assembly 1400 to protrude therefrom such as a portion of engagement portion 1422 and/or a portion of lockout 1440.

Hard stop 1418 is defined by distal retainer 1410 in a lower distal portion of distal retainer 1410. In this position, hard stop 1418 is configured to block a lower distal segment of lockout channel 1416. As will be described in greater detail below, hard stop 1418 is generally configured to engage a portion of lockout 1440 to prevent advancement of lockout 1440 relative to hard stop 1418. Although hard stop 1418 of the present example is configured with a square or rectangular cross-section, it should be understood that other suitable cross-sectional shapes may be used in other examples such as circular, oval-shaped, triangular, and/or etc.

Figure 29:
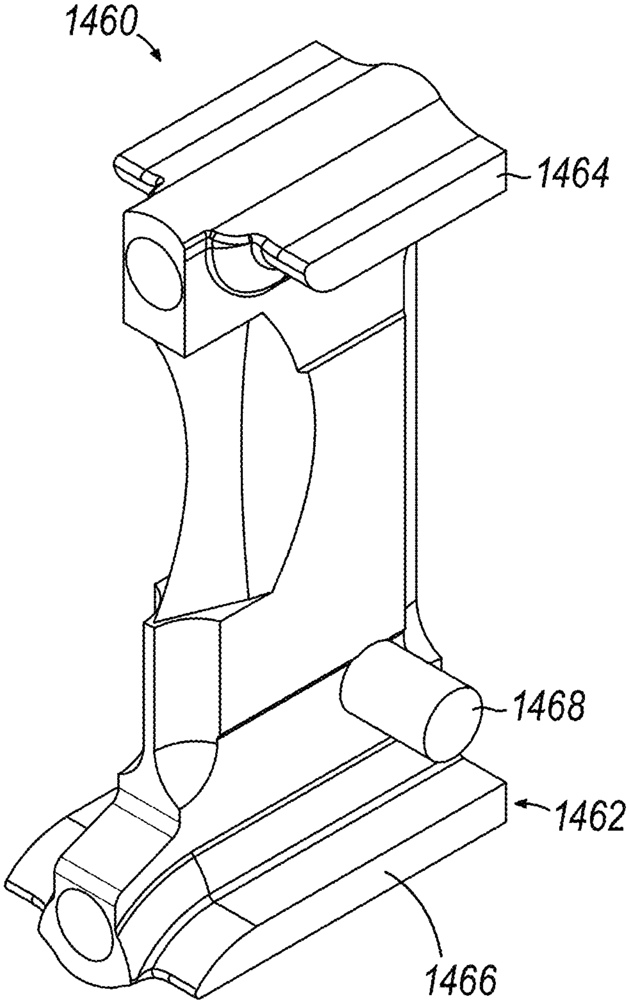
FIG. 29 is a side elevational view of a knife for use with the lockout assembly of FIG. 28.

FIG. 29 depicts an alternative knife 1460 configured for use with lockout assembly 1410 in lieu of knife 206 described above. Knife 1460 of the present example is substantially similar to knife 206 described above except where otherwise described herein. Like knife 206 described above, knife 1460 of the present example includes a knife sled 1462 having an upper knife tab 1464 and a lower knife tab 1466. As similarly described above, tabs 1464, 1466 are configured to guide knife 1460 during advancement relative to end effector 200.

Unlike knife 206 described above, knife 1460 of the present example includes features to promote engagement with lockout assembly 1400. In particular, knife 1460 of the present example includes a lock protrusion 1468 extending outwardly from a slide surface of knife 1460 corresponding to the side of end effector 200 including lockout assembly 1400. Lock protrusion 1468 is positioned above lower knife tab 1466 and proximate lower knife tab 1466. Although lock protrusion 1468 is shown as a cylindrical protrusion in the present example, it should be understood that lock protrusion 1468 may define a variety of alternative shapes in other examples such as square, D-shaped, triangular, spherical, etc.

Figure 30A:
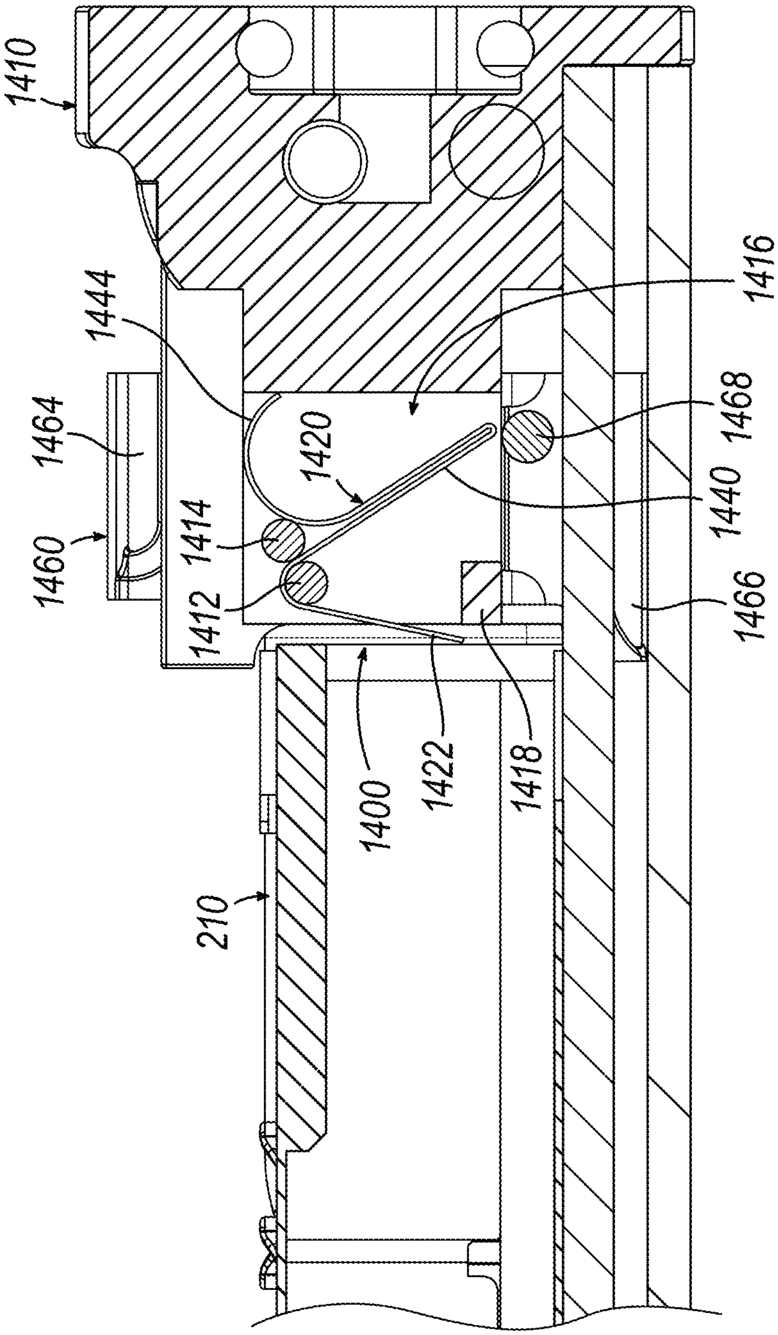
FIG. 30A is a side cross-sectional view of the lockout assembly of FIG. 28 in use with the surgical instrument of FIG. 1, the lockout assembly in an unlocked condition.
Figure 30B:
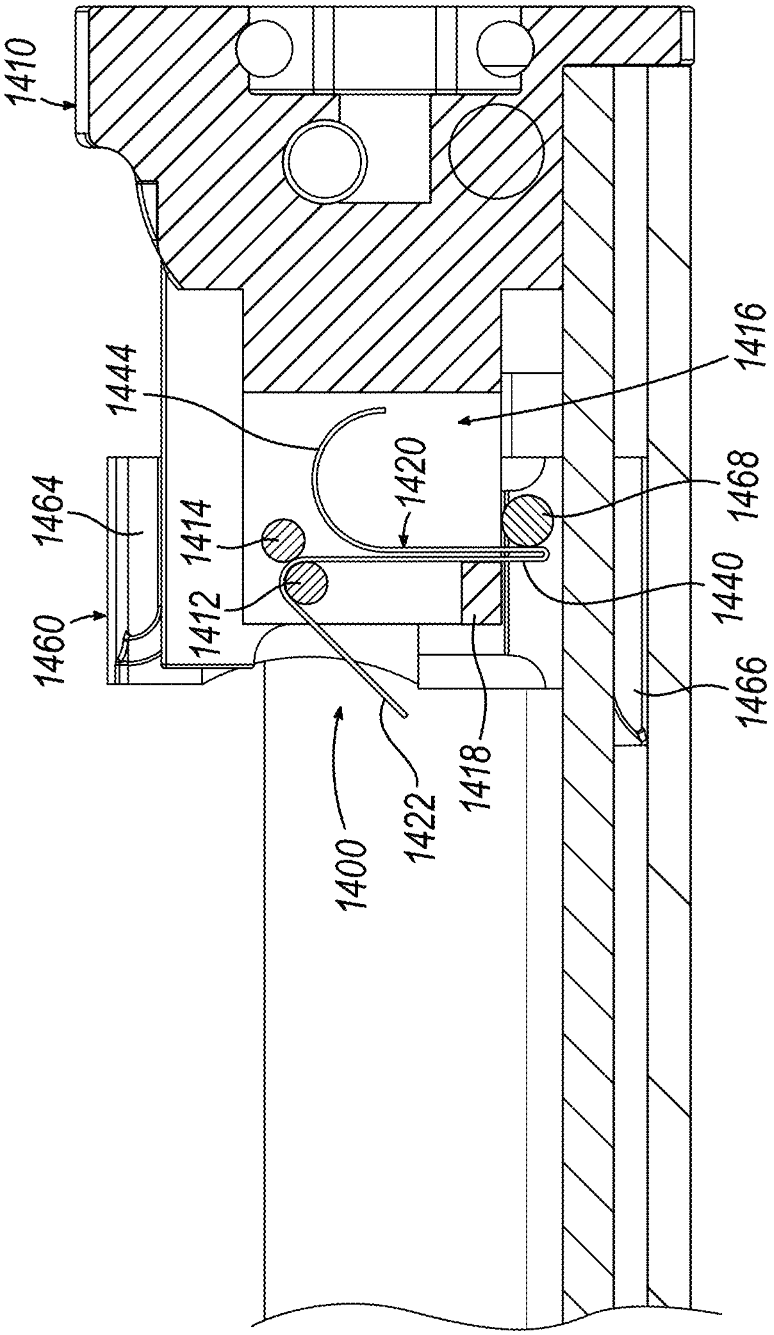
FIG. 30B is another side cross-sectional view of the lockout assembly of FIG. 28 in use with the surgical instrument of FIG. 1, the lockout assembly in a locked condition.

FIGS. 30A and 30B show an illustrative use of lockout assembly 1400 described above. As best seen in FIG. 30A, lockout assembly may begin in an initial unlocked condition. As can be seen, the initial unlocked condition corresponds to a condition where staple cartridge 210 is disposed within end effector 200. In this condition, engagement portion 1422 of sensor 1420 is engaged by at least a portion of staple cartridge 210. This engagement pivots the rod of lockout assembly 1400 about lower locator pin 1412, thereby driving lockout 1440 proximally. With lockout 1440 driven proximally, the effective projection of lockout 1440 relative to distal retainer 1410 is reduced, which moves lockout 1440 into a position that is clear of the distal advancement path of lock protrusion 1468 of knife 1460. As a result, knife 1460 can be advanced distally without interference from lockout 1440. Optionally, in examples where counterbalance 1444 is configured as a spring or resilient structure, counterbalance 1444 may also be compressed in this configuration.

Once staple cartridge 210 is removed from end effector 200 as shown in FIG. 30B, lockout assembly 1400 may transition to a locked condition. As can be seen, engagement portion 1422 of sensor 1420 is freely movable relative to distal retainer 1410 once staple cartridge 210 is removed. With engagement portion 1422 free to move, the weight of counterbalance 1444 drives pivoting of the rod of lockout assembly 1400 about lower locator pin 1412. Optionally, in examples where counterbalance 1444 is configured as a spring or resilient structure, counterbalance 1444 may positively drive pivoting of the rod of lockout assembly 1400 using engagement with digital retainer 1410. Regardless, such pivoting results in engagement portion 1422 pivoting upwardly and distally. Similarly, this also results in lockout 1440 pivoting downwardly and distally. As a result of the pivoting of lockout 1440 in particular, the effective extension of lockout 1440 with respect to distal retainer 1410 is increased. This results in lockout 1440 being positioned in the distal advancement path of lock protrusion 1468 of knife 1460, impeding distal movement of knife 1460 via engagement between lock protrusion 1468 and lockout 1440. Upon engagement between lockout 1440 and lock protrusion 1468, lockout 1440 can be driven into hard stop 1418 of distal retainer 1410. Hard stop 1418 then block further distal advancement of lockout 1440, which in turn blocks or otherwise impedes further distal advancement of knife 1460 via lock protrusion 1468.

It should be understood the lockout provided by lockout assembly 1400 in the present example may be a partial or soft lock rather than a hard lock. In particular, due to the nature of lockout assembly 1400 being formed of a rod, the maximum amount of lockout force applied by lockout assembly 1400 on knife may be limited. Thus, in such examples, robotic or other electronic control systems may detect the force applied to knife 1460 by lockout 1440 via lock protrusion 1468. Such robotic or other electronic control systems may then prevent further advancement of knife 1460 through software or other control algorithms.

It should be understood that sensor 1420 can be configured to engage a variety of structures of staple cartridge 210 to transition lockout assembly 1410 between the locked and unlocked conditions. For instance, in some configurations, engagement portion 1422 of sensor 1420 is configured to engage cartridge sled 210A of staple cartridge 210 specifically rather than a general structure of staple cartridge 210. This configuration may be desirable in some uses to provide locking from lockout assembly 1400 in both spent-cartridge conditions and absent-cartridge conditions. Specifically, by configuring engagement portion 1422 to engage cartridge sled 210A, the unlocked condition will only be established when both staple cartridge 210 is present and cartridge sled 210A is in an initial proximal position. In such uses, it should be understood that staple cartridge 210 and/or cartridge sled 210A may include one or more features to facilitate such engagement such as channels, protrusions, and/or etc.

D. Illustrative Alternative Lockout Assembly with Swing Arm

Figure 31:
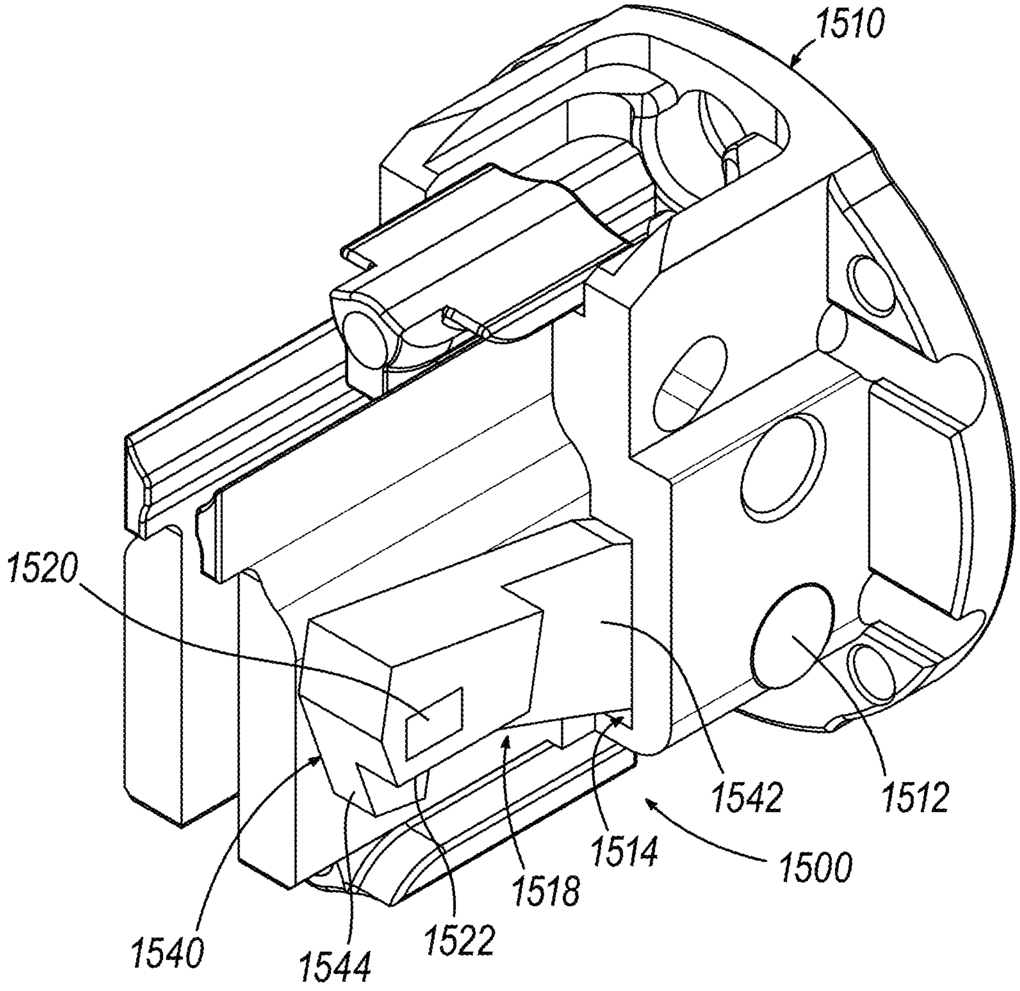
FIG. 31 is a perspective view of still another illustrative alternative lockout assembly that may be readily incorporated into the end effector of the surgical instrument of FIG. 1.

FIG. 31 depicts a lockout assembly 1500, which may be readily incorporated into end effector 200 of surgical instrument 1000 described above. For instance, in the present example, lockout assembly 1500 is incorporated into a portion of a distal retainer 1510, which may be incorporated into end effector 200 in lieu of distal retainers 324, 1110, 1210, 1410 described above. It should be understood that distal retainer 1510 of the present example is substantially similar to distal retainer 324 described above unless otherwise described herein. Although aspects of lockout assembly 1500 are described herein as being incorporated into distal retainer 1510, it should be understood that lockout assembly 1500 may be readily incorporated into other portions of end effector 200 in other examples as will be appreciated by those of ordinary skill in the art in view of the teachings herein.

Lockout assembly 1510 of the present example includes swing arm 1518, which defines both a sensor 1520 (also referred to as a sensor element, sensor portion), and a lockout 1540 (also referred to as a lockout element, lockout portion). Lockout 1540 defines an arm 1542 and a brake 1544 disposed on a distal end of arm 1542. A portion of arm 1542 is disposed within a channel 1514 defined within distal retainer 1510. Within channel 1514, arm 1542 is coupled to a pivot post 1512 of distal retainer 1510. Thus, arm 1542 is configured to pivot relative to distal retainer 1510, yet grounded relative to distal retainer 1510. Although arm 1542 of the present example is pivotably coupled to distal retainer 1510, it should be understood that in other examples, arm 1542 can be pivotably coupled to other structures of end effector 200 such as cartridge jaw 202.

Brake 1544 is disposed at a distal end of arm 1524 opposite the coupling of arm 1542 to pivot post 1512. Brake 1544 is generally defined by a downwardly extending protrusion, which extends toward a lower portion of knife 206 such as lower knife tab 246. Thus, brake 1544, or the combination of brake 1544 and arm 1524, defines an L-shaped feature that is configured to block or otherwise impede movement of knife 206 when positioned in a predetermined position relative to knife 206.

Sensor 1520 is configured to be engaged and/or manipulated by at least a portion of staple cartridge 210, as will be described in greater detail below. It should be understood use of the term "sensor" herein is used to encompass physical sensing mechanisms by one or more components being responsive to the physical presence of one or more other components. Of course, as will be appreciated in view of the teachings herein, sensor 1520 in some examples may additionally, or alternatively, include certain electronic sensing mechanisms.

Sensor 1520 protrudes laterally from a portion of lockout 1540. In particular, sensor 1520 protrudes from a distal portion of arm 1542 proximate brake 1544. Sensor 1520 of the present example defines an engagement face 1522. Engagement face 1522 is generally configured to engage a portion of staple cartridge 202 such as cartridge sled 210A, as will be described in greater detail below. It should be understood that engagement face 1522 may define a variety of shapes and configurations, which may be complementary to aspects of staple cartridge 202 and/or cartridge sled 210A. For instance, in the present example, engagement face 1522 generally defines a flat planar configuration oriented downwardly. In other examples, engagement face 1522 may optionally include angled or curved features configured to promote engagement with aspects of staple cartridge 202 and/or cartridge sled 210A.

Figure 32:
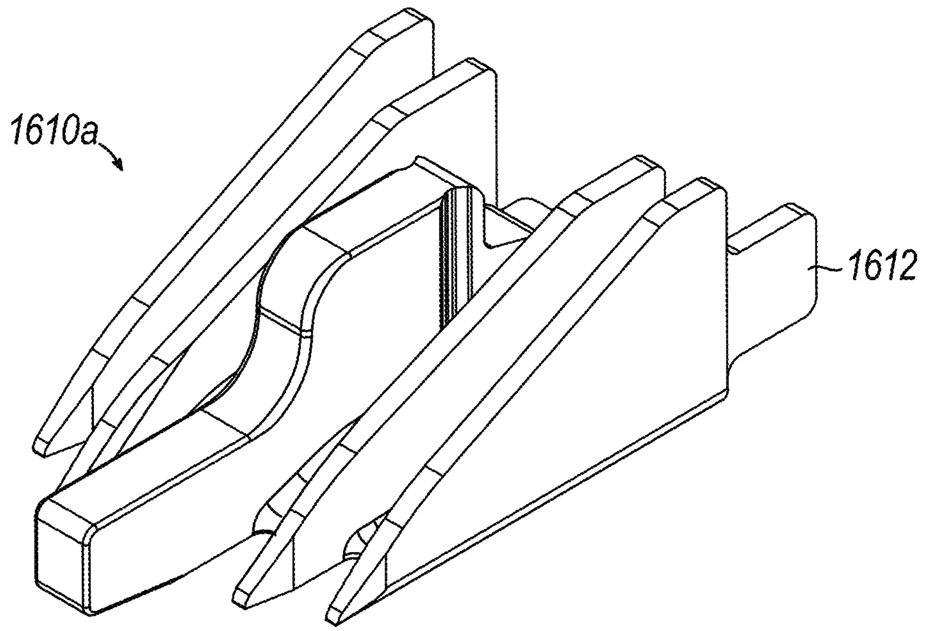
FIG. 32 is a perspective view of a cartridge sled for use with the lockout assembly of FIG. 31.

FIG. 32 depicts an alternative cartridge sled 1610A that may be readily incorporated into staple cartridge 210 for use in combination with lockout assembly 1500 described herein. Cartridge sled 1610A is substantially similar to cartridge sled 210A described above. However, unlike cartridge sled 210A described above, cartridge sled 1610A of the present example includes a drive protrusion 1612 protruding from a proximal surface of cartridge sled 1610A. Drive protrusion 1612 is generally configured to protrude proximally from a portion of staple cartridge 210 to promote engagement between cartridge sled 1610A and lockout assembly 1500. As will be described in greater detail below, drive protrusion 1612 may, for example, engage engagement face 1522 of sensor 1520 to drive lockout 1540 from a locked condition to an unlocked condition.

Figure 33A:
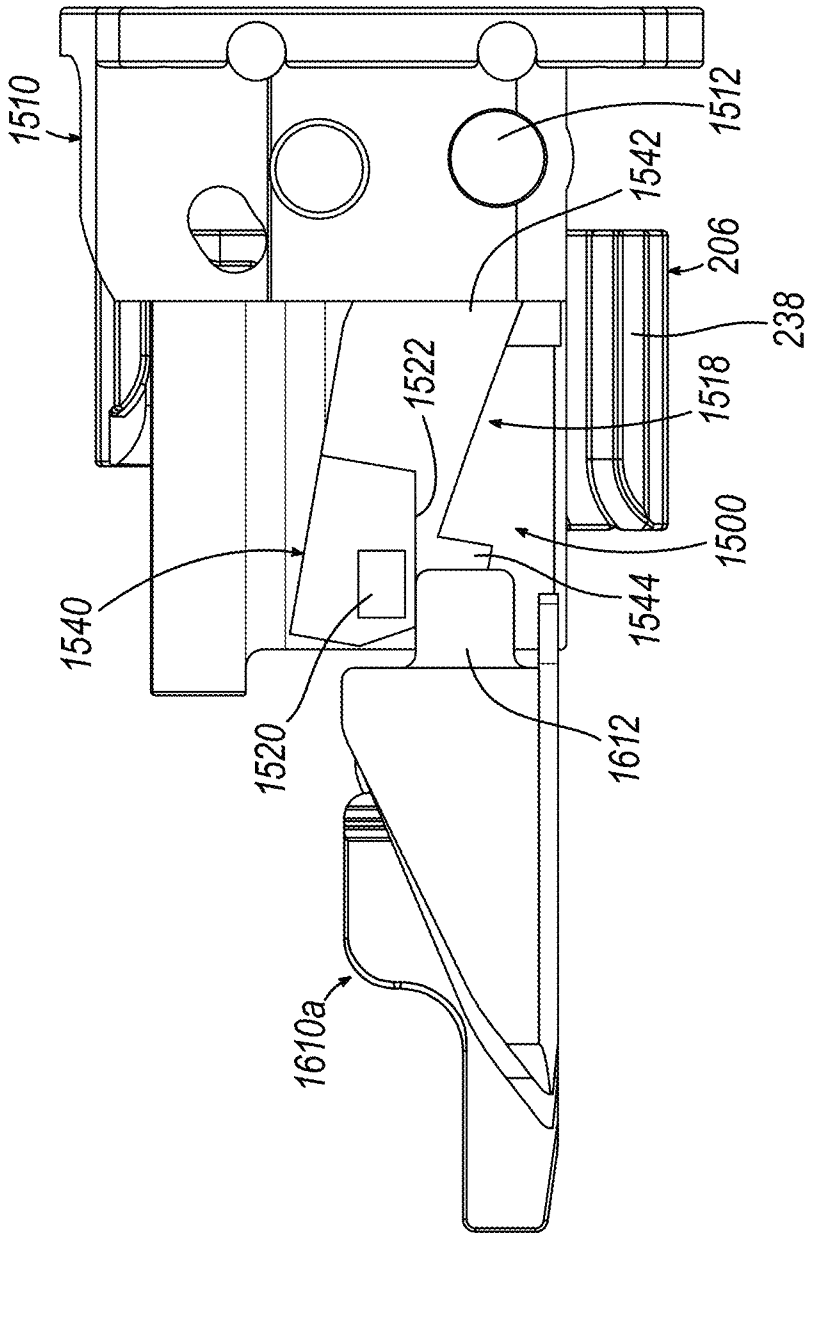
FIG. 33A is a side elevational view of the lockout assembly of FIG. 31 in use with the surgical instrument of FIG. 1, the lockout assembly in an unlocked condition.
Figure 33B:
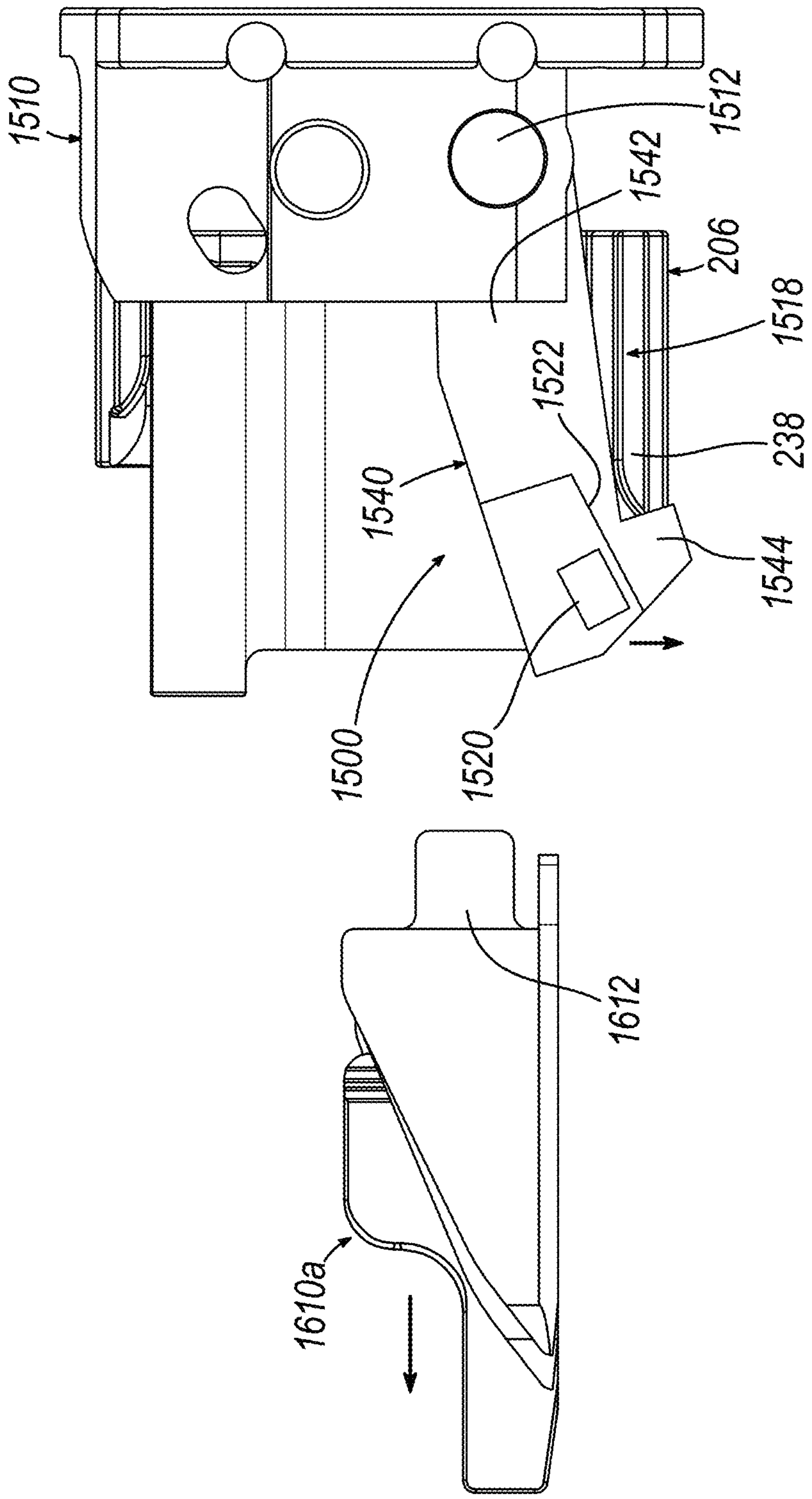
FIG. 33B is another side elevational view of the lockout assembly of FIG. 31 in use with the surgical instrument of FIG. 1, the lockout assembly in a locked condition.

FIGS. 33A through 33B depicts an illustrative use of lockout assembly 1500 to lockout advancement of knife 202 during certain operational conditions. For instance, as best seen in FIG. 33A, lockout assembly 1500 may initially being in an unlocked condition. In this condition, engagement face 1522 of sensor 1520 rests on an upper surface of drive protrusion 1612 of cartridge sled 1610A. In this condition, engagement face 1522 is substantially parallel with respect to the upper surface of drive protrusion 1612, although engagement face 1522 may be oriented at an angle in other uses. Regardless, the position of engagement face 1522 on drive protrusion 1612 pivots arm 1542 of lockout 1540 upwardly. As a result, brake 1544 is positioned above lower knife tab 238 of knife 206 and out of the distal travel path of knife 206, thereby permitting distal advancement of knife 206.

FIG. 33B depicts lockout assembly 1500 in a locked condition. In this condition, cartridge sled 1610A is positioned away from lockout assembly 1500 either by advancement of cartridge sled 1610A using knife 206 (spent-cartridge condition) or by removal of staple cartridge 210 entirely (absent-cartridge condition). Regardless, with cartridge sled 1610A positioned away from lockout assembly 1500, engagement face 1522 of sensor 1520 disengages from drive protrusion 1612, permitting downward movement of sensor 1520 and swing arm 1518 as a whole. This results in pivoting of arm 1542 downwardly, which moves brake 1544 toward lower knife tab 238 of knife 206. Brake 1544 is then positioned in the distal travel path of knife 206, preventing distal advancement of knife 206 by blocking movement of lower knife tab 238.

E. Illustrative Alternative Lockout Assembly with Pivoting Action

Figure 34:
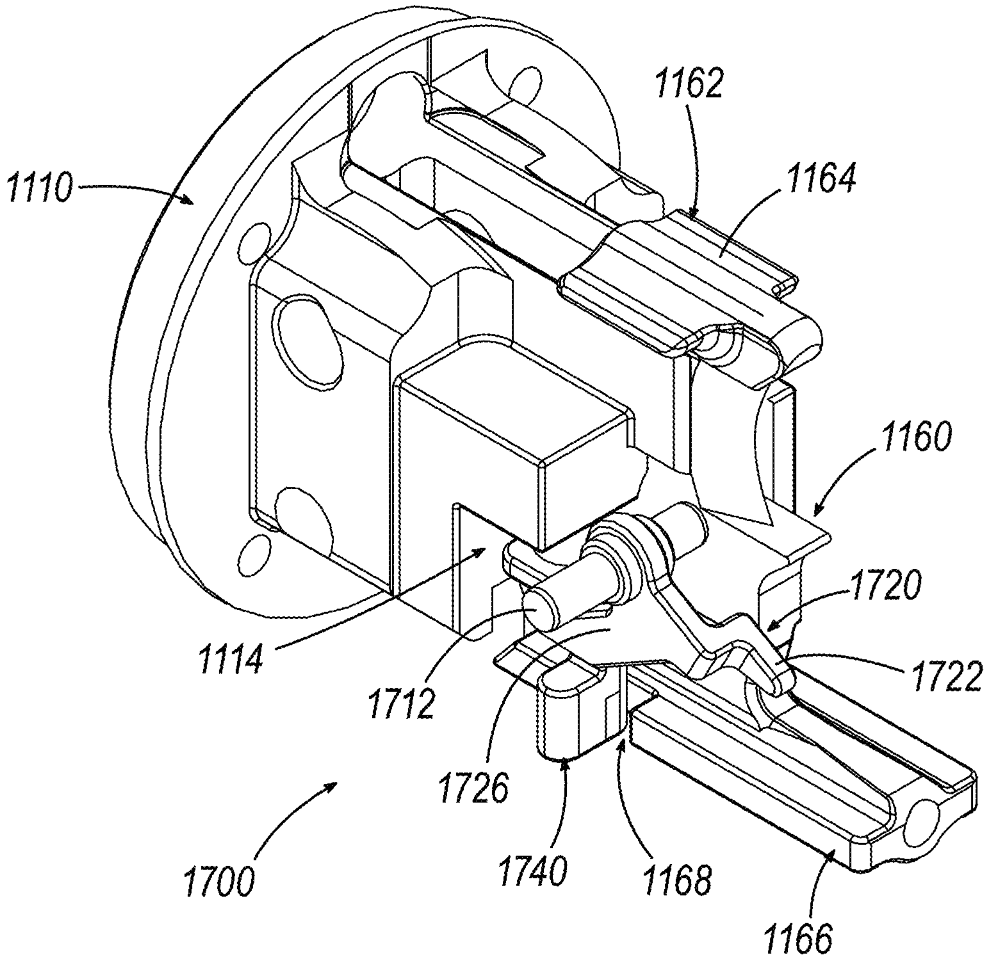
FIG. 34 is a perspective view of an illustrative lockout assembly that may be readily incorporated into the end effector of the surgical instrument of FIG. 1.

FIG. 34 depicts an alternative lockout assembly 1700, which may be readily incorporated into end effector 200 of surgical instrument 1000 described above. Lockout assembly 1700 of the present example is substantially similar to lockout assembly 1100 described above, except where otherwise described herein. For instance, like lockout assembly 1100 described above, lockout assembly 1700 of the present example is incorporated into a portion of a distal retainer 1110, which may be incorporated into end effector 200 in lieu of distal retainer 324 described above. Although aspects of lockout assembly 1700 are described herein as being incorporated into distal retainer 1110, it should be understood that lockout assembly 1700 may be readily incorporated into other portions of end effector 200 in other examples as will be appreciated by those of ordinary skill in the art in view of the teachings herein.

As with lockout assembly 1100 described above, lockout assembly 1700 includes a sensor 1720 (also referred to as a sensor element), a lockout 1740 (also referred to as a lockout element), and a basing member 1750. As with sensor 1120 described above, sensor 1720 of the present example is configured to be engaged and/or manipulated by at least a portion of staple cartridge 210. It should be understood use of the term "sensor" herein is used to encompass physical sensing mechanisms by one or more components being responsive to the physical presence of one or more other components. Of course, as will be appreciated in view of the teachings herein, sensor 1720 in some examples may additionally, or alternatively, include certain electronic sensing mechanisms.

Figure 35:
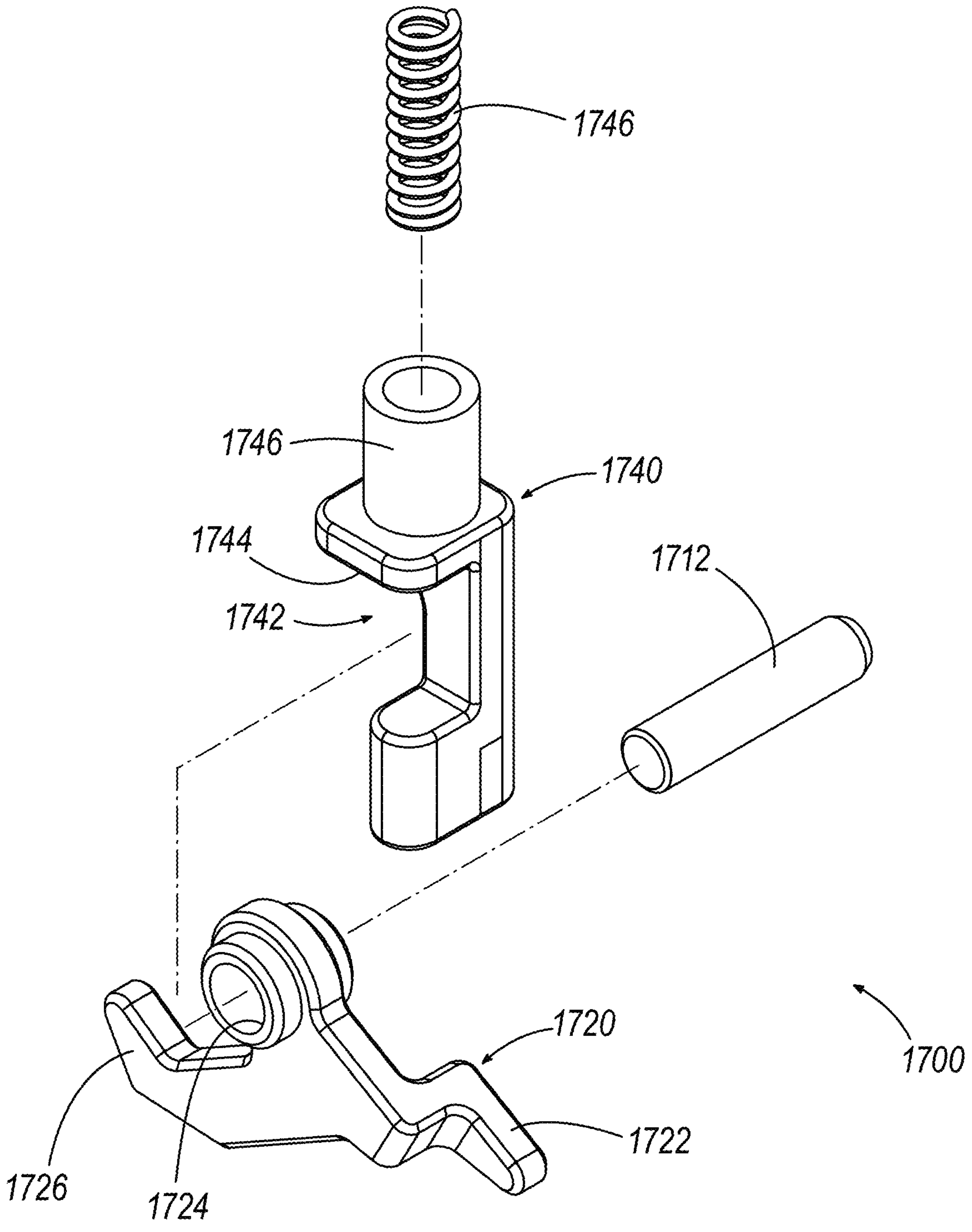
FIG. 35 is an exploded view of the lockout assembly of FIG. 34.

As best seen in FIG. 35, sensor 1720 includes an engagement portion 1722, an attachment 1724, and a manipulator 1726. Engagement portion 1722 is configured to extend distally relative a portion of distal retainer 1110 to engage a portion of staple cartridge 210. As will be described in greater detail below, engagement portion 1722 can be driven by the presence of one or more portions of staple cartridge 210 to pivot or otherwise move sensor 1720. To facilitate such a function, engagement portion 1722 can include particular geometric shapes. For instance, unlike engagement portion 1122 described above, engagement portion 1722 of the present example is angled downwardly with respect to attachment 1724 and/or manipulator 1726 to facilitate alignment with a predetermined portion of staple cartridge 210. Additionally, a portion of engagement portion 1722 is tapered or necked down to provide a decreased surface area for engagement with one or more portions of staple cartridge 210.

Unlike engagement portion 1122 described above, engagement portion 1722 of the present example includes a bent section rather than being generally straight to facilitate alignment with a predetermined portion of staple cartridge 210. In particular, engagement portion 1722 includes one or more shaped sections or portions to facilitate engagement with staple cartridge 210 and/or cartridge sled 210A. For instance, engagement portion 1722 of the present example includes a dog leg section. Such a dog leg section may be desirable to orient one or more features of engagement portion 1722 closer to aspects of staple cartridge 210 such as cartridge sled 210A or components associated therewith such as channels.

Attachment 1724 is positioned proximate to engagement portion 1722 and is generally configured to movably secure sensor 1720 to distal retainer 1110 or other suitable components of end effector 200. In the present example, attachment 1724 is configured as a ring other structure extending upwardly from engagement portion 1722 and manipulator 1726 of sensor 1120. The interior of the ring-shape of attachment 1724 is configured to receive a corresponding pivot post 1712. In some examples, pivot post 1712 may extend from distal retainer 1110 as similarly described above with respect to pivot post 1112. In other examples, pivot post 1712 can couple to other components of end effector 200 such as cartridge jaw 202. Thus, in the present configuration, attachment 1724 is configured to permit a pivoting action of sensor 1720 relative to pivot post 1712. In other words, attachment 1724 is configured as a fixed pivot that grounds sensor 1720 with respect to distal retainer 1110 and/or other suitable structures such as cartridge jaw 202. Although attachment 1724 of the present example uses a post-bore configuration, it should be understood that in other examples various alternative configurations may be used for attachment 1724.

Manipulator 1726 extends proximally relative to attachment 1724 and is generally configured to manipulate lockout 1740 in response to movement of engagement portion 1722. Like manipulator 1126, manipulator 1726 of the present example is configured as an elongate structure. However, unlike manipulator 1726 described above, manipulator 1726 also includes a curved or finger-shaped form that first curves downwardly while extending proximally away from attachment 1724 and then curves upwardly toward a portion of lockout 1740. The particular shape of manipulator 1726 in the present example is configured to provide movable pivot that can transfer movement of manipulator 1726 to lockout 1740.

Like lockout 1140 described above, lockout 1740 of the present example is generally configured to respond to movement of sensor 1720 to selectively lock, interfere, block, or otherwise impede movement of knife 1160 relative to distal retainer 1110. Lockout 1740 of the present example is generally configured as a cylindrical post or bollard. However, unlike lockout 1140 described above, lockout 1740 of the present example includes additional features to facilitate engagement between lockout 1740 and sensor 1720. For instance, lockout 1740 of the present example includes an indentation 1742 and a pivot surface 1744 oriented above indentation 1742.

Indentation 1742 is generally configured to receive at least a portion of manipulator 1726. In particular, indentation 1742 is configured as a cutout or indentation in the surface of one side of lockout 1740. In other words, a portion of lockout 1740 is narrowed to define indentation 1742. Indentation 1742 is generally desirable in the present example to provide clearance for manipulator 1726. This permits manipulator 1726 and lockout 1740 to occupy at least of the same footprint, thereby saving space within the interior of end effector 200.

Pivot surface 1744 is generally configured to engage at least a portion of manipulator 1726. In particular, pivot surface 1744 is configured as a downwardly oriented surface projecting into the space immediately above indentation 1742. In this configuration, manipulator 1726 can move within indentation 1742 to engage pivot surface 1744 to drive lockout 1740 upwardly, while otherwise being free to move within indentation.

As with lockout 1140 described above, lockout 1740 of the present example is generally disposed within channel 1114 of distal retainer 1110. Thus, as similarly described above, in the present example, channel 1114 is configured to at least vertically constrain lockout 1740 for movement along an axis defined by channel 1114. Similarly, at least a portion of sensor 1720 is laterally offset with respect to lockout 1740 and is thus generally positioned outside channel 1114. Consequently, lockout 1740 is configured to move axially, or translate, within channel 1114, also perpendicularly relative to the longitudinal axis defined by distal retainer 1110. Additionally, by being disposed within channel 1114, lockout 1740 is grounded along the length of distal retainer 1110. In other words, lockout 1740 is movable within channel 1114 vertically, but fixed within channel 1114 horizontally.

Lockout 1740 further includes a retaining collar 1746 oriented above pivot surface 1744, which is configured to receive biasing member 1750. Retaining collar 1746 defines a generally cylindrical structure with a bore therein oriented upwardly to receive biasing member 1750. Retaining collar 1746 is merely optional and may be omitted in some examples. For instance, in other examples, biasing member 1750 may instead contact an upper surface of pivot surface 1744 or lockout 1740 directly.

Like biasing member 1150 described above, biasing member 1750 of the present example is also generally disposed within channel 1114 between lockout 1740 and a portion of distal retainer 1110. Thus, biasing member 1750 is generally configured to bias lockout 1740 outwardly with respect to channel 1114 or downwardly. In the present example, biasing member 1750 includes a spring such as a coil spring. In other examples, biasing member 1750 can include a variety of other features configured to resiliently bias lockout 1740 away from a portion of distal retainer 1110.

In some examples, lockout 1740 can be configured to engage directly with knife 206 to prevent or otherwise impede proximal movement of knife 206. For instance, lockout 1740 may be driven downwardly in a proximal position relative to lower knife tab 246 to block or otherwise impede proximal movement of knife 206. However, like lockout 1140 described above, lockout 1740 of the present example can likewise be used with knife 1160. As similarly described above, knife 1160 includes features to promote engagement with lockout assembly 1700 such as lock recess 1168, one or more ramps 1170, 1174 and one or more engagement faces 1172.

It should be understood that lockout assembly 1700 may be used substantially similarly as lockout assembly 1100 described above. For instance, as similarly described above, lockout assembly 1700 may begin in an initial unlocked position similar to the unlocked position described above with respect to lockout assembly 1100. In this position, lockout 1740 rests on top of lower knife tab 1166 against the resilient bias provided by biasing member 1750. This positions lockout assembly 1100 in an unlocked position with lockout 1740 in an upward or recessed position relative to distal retainer 1110. Due to the linkage between lockout 1740 and sensor 1720, sensor 1720 is positioned with engagement portion 1722 positioned downwardly and manipulator 1726 positioned upwardly.

Similarly, lockout assembly 1700 may move from the initial unlocked position described above into a locked position. The locked position may correspond to a condition where end effector 200 remains in an absent-cartridge condition with staple cartridge 210 not disposed within end effector 200, or with end effector 200 in a spent-cartridge condition with cartridge sled 210A driven distally. Without the presence of staple cartridge 210 (or alternatively without the presence of cartridge sled 210A), sensor 1720 is free to travel within end effector 200 subject to any forces applied by lockout 1740. Thus, upon distal movement of knife 1160, lockout 1740 may move from resting on lower knife tab 1166 to resting within lock recess 1168. As a result, lockout 1740 can translate downwardly relative to distal retainer 1110 and into lock recess 1168 of knife 1160 under the resilient bias provided by biasing member 1750. Lockout 1740 can then engage engagement face 1172 of knife 1160 preventing further distal movement of knife 1160.

As similarly described above, sensor 1720 is generally free to travel within end effector 200 subject to any forces applied by lockout 1740. This is due to engagement portion 1722 being unrestricted by any portion of end effector 200. Thus, as lockout 1740 translates downwardly relative to distal retainer 1110, manipulator 1726 is likewise driven downwardly. This moves the movable pivot coupling lockout 1740 and sensor 1720 downwardly into substantial alignment with the fixed pivot between sensor 1720 and distal retainer 1110 (or cartridge jaw (202)). As a result of this downward movement of manipulator 1726, engagement portion 1722 moves upwardly or in an opposite direction relative to manipulator 1726.

Under some circumstances, lockout assembly 1700 can be forced into the unlocked position using sensor 1720. For instance, the presence of staple cartridge 210 within end effector 200 can act to force lockout assembly 1700 into the unlocked position. As similarly described above with respect to lockout assembly 1100, a portion of staple cartridge 210 such as cartridge sled 210A may engage engagement portion 1722 of sensor 1720. As a consequence of this engagement, engagement portion 1722 may be driven downwardly, while manipulator 1726 may be driven in an opposite, upward, direction. Due to the linkage between sensor 1720 and lockout 1740, lockout 1740 can also be driven upwardly into channel 1114 of distal retainer 1110 against the resilient bias of biasing member 1750. Thus, upward movement of lockout 1740 withdraws lockout 1740 from lock recess 1168 of knife 1160, thereby permitting distal movement of knife 1160.

III. EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body (700); (b) a shaft (600A) extending distally from the body; (c) an end effector (200) operatively coupled with the shaft, wherein the end effector includes: (i) a cartridge jaw (202), (ii) an anvil jaw (204) configured to cooperate with the cartridge jaw to clamp and staple tissue, (iii) a knife (206) actuatable within the cartridge jaw and having a cutting edge configured to cut tissue, and (iv) a distal retainer (1110) configured to couple the cartridge jaw to a portion of the shaft; and (d) a lockout assembly (1100) including a sensor (1120) and a lockout (1140), the lockout being vertically constrained, the sensor being associated with a first pivot (1124) and a second pivot, the first pivot being a fixed pivot grounded with respect to a channel (1114), the second pivot being a moving pivot with respect to the lockout, the lockout assembly having an unlocked position and a locked position, the second pivot being positioned above the first pivot when the lockout assembly is in the unlocked position with the lockout being configured to provide no interference with respect to actuation of the knife, the first pivot and the second pivot being positioned at substantially the same height when the lockout assembly is in the locked position.

Example 2

The apparatus of Example 1, the knife defining a lock recess (1168) disposed between a proximal portion of a lower knife tab (1166) and a distal portion of the lower knife tab, the lockout being configured for receipt within the lock recess with the lockout assembly is in the locked position.

Example 3

The apparatus of Example 2, the proximal portion of the lower knife tab defining an engagement face (1172) and a proximal ramp (1174), the engagement face being configured to engage the lockout to prevent distal advancement of the knife.

Example 4

The apparatus of Example 2, the proximal portion of the lower knife tab defining an engagement face (1172) and a proximal ramp (1174), the distal portion of the lower knife tab defining a distal ramp (1170), the engagement face being configured to engage the lockout to prevent distal advancement of the knife, the proximal ramp and the distal ramp being configured to engage the lockout to direct the lockout upwardly way from the lower knife tab.

Example 5

The apparatus of any of Examples 1 through 4, the channel being defined by a portion of the distal retainer.

Example 6

The apparatus of any of Examples 1 through 5, the distal retainer including a pivot post (1112), the first pivot associated with the sensor being pivotably secured to the pivot post.

Example 7

The apparatus of any of Examples 1 through 6, the lockout assembly further including a bias (1150), the bias being configured to bias the lockout assembly toward the locked position.

Example 8

The apparatus of Example 7, the bias being a coil spring at least partially disposed within the channel.

Example 9

The apparatus of any of Examples 1 through 8, the sensor including an engagement portion (1122) and a manipulator (1126), the engagement portion and the manipulator being disposed on opposite sides of the first pivot.

Example 10

The apparatus of Example 9, the engagement portion being configured to engage a portion of a staple cartridge (210) when the staple cartridge is disposed within the cartridge jaw.

Example 11

The apparatus of Example 9, the engagement portion including one or more shaped portions being configured to permit engagement between the engagement portion and a portion of a staple cartridge (210) when the staple cartridge is disposed within the cartridge jaw.

Example 12

The apparatus of Example 9, the engagement portion including one or more shaped portions being configured to permit engagement between the engagement portion and a portion of a cartridge sled (210A) of a staple cartridge (210) when the staple cartridge is disposed within the cartridge jaw.

Example 13

The apparatus of any of Examples 1 through 12, wherein the second pivot being a pivotable coupling between the lockout and the sensor.

Example 14

The apparatus of any of Examples 1 through 12, wherein the sensor is configured to engage a predetermined portion of the lockout to define the second pivot.

Example 15

The apparatus of any of Examples 1 through 14, wherein the sensor is laterally offset with respect to the lockout.

Example 16

An apparatus, comprising: (a) a body (700); (b) a shaft (600A) extending distally from the body; (c) an end effector (200) operatively coupled with the shaft, wherein the end effector includes: (i) a cartridge jaw (202), (ii) an anvil jaw (204) configured to cooperate with the cartridge jaw to clamp and staple tissue, (iii) a knife (206) actuatable within the cartridge jaw and having a cutting edge configured to cut tissue, and (iv) a distal retainer (1210) configured to couple the cartridge jaw to a portion of the shaft; and (d) a lockout assembly (1200) including a sensor (1220) and a lockout (1240), the sensor defining an engagement portion (1222) and a manipulator (1226), a portion of the sensor being resiliently biased to bias the manipulator (1226) toward a predetermined position, the lockout including one or more arms (1242) and a brake (1244) disposed on a distal end of the one or more arms, the one or more arms being configured to pivot relative to the distal retainer to move the brake from a locked position in a distal advancement path of the knife to an unlocked position below the knife, the manipulator being in communication with the brake to bias the brake toward the locked position.

Example 17

The apparatus of Example 16, the sensor further including a base (1228), the engagement portion and the manipulator projecting from a portion of the base.

Example 18

The apparatus of Example 17, the engagement portion and the manipulator being integral with the base.

Example 19

The apparatus of Examples 17 or 18, the base being secured to a portion of the cartridge jaw.

Example 20

The apparatus of any of Examples 16 through 19, the manipulator of the sensor being configured to directly engage the brake of the lockout.

Example 21

The apparatus of any of Examples 16 through 20, the one or more arms of the lockout including a pair of arms, the brake extending from one arm of the pair of arms to another arm.

Example 22

The apparatus of Example 21, the distal retainer defining a channel (1114) corresponding to each respective arm of the pair of arms, each arm of the pair of arms extending into the respective channel of the distal retainer.

Example 23

The apparatus of Example 21, the distal retainer defining a channel (1114) corresponding to each respective arm of the pair of arms, each arm of the pair of arms extending into the respective channel of the distal retainer and being pivotably secured to a pivot post (1112) disposed within each channel.

Example 24

The apparatus of any of Examples 21 through 23, the pair of arms being separated from each other by a width, the width being greater than a width defined by the knife.

Example 25

The apparatus of any of Examples 16 through 24, the engagement portion of the sensor being configured to engage a cartridge sled (210A) of a staple cartridge (210) disposed within the cartridge jaw, the engagement portion of the sensor being responsive to the cartridge sled to drive the manipulator downwardly away from the cartridge sled.

Example 26

An apparatus, comprising: (a) a body (700); (b) a shaft (600A) extending distally from the body; (c) an end effector (200) operatively coupled with the shaft, wherein the end effector includes: (i) a cartridge jaw (202), (ii) an anvil jaw (204) configured to cooperate with the cartridge jaw to clamp and staple tissue, (iii) a knife (206) actuatable within the cartridge jaw and having a cutting edge configured to cut tissue, and (iv) a distal retainer (1410) configured to couple the cartridge jaw to a portion of the shaft; and (d) a lockout assembly (1400) including a rod defining a sensor portion (1420) and a lockout portion (1440), the sensor defining an engagement portion (1422), the lockout portion extending downwardly with respect to the engagement portion, the engagement portion being configured to engage a portion of a staple cartridge (210) disposed in the cartridge jaw to pivot the lockout portion with respect to the distal retainer to pivot the lockout portion from a locked position in a distal translation path of the knife to an unlocked position outside of the distal translation path of the knife.

Example 27

The apparatus of Example 26, the rod being a single unitary part.

Example 28

The apparatus of Examples 26 or 27, the rod defining a circular cross-section.

Example 29

The apparatus of any of Examples 26 through 28, the distal retainer defining a lockout channel (1416) and a hard stop (1418) disposed within a portion of the lockout channel, at least a portion of the rod being disposed within the lockout channel.

Example 30

The apparatus of Example 29, the engagement portion of the sensor portion extending outwardly from the lockout channel of the distal retainer.

Example 31

The apparatus of any of Examples 26 through 30, the rod further defining a counterbalance, the counterbalance being disposed on a side of the rod opposite the sensor portion.

Example 32

The apparatus of any of Examples 26 through 31, the engagement portion of the sensor portion being configured to engage a cartridge sled (210A) of the staple cartridge.

Example 33

An apparatus, comprising: (a) a body (700); (b) a shaft (600A) extending distally from the body; (c) an end effector (200) operatively coupled with the shaft, wherein the end effector includes: (i) a cartridge jaw (202), (ii) an anvil jaw (204) configured to cooperate with the cartridge jaw to clamp and staple tissue, (iii) a knife (206) actuatable within the cartridge jaw and having a cutting edge configured to cut tissue, and (iv) a distal retainer (1510) configured to couple the cartridge jaw to a portion of the shaft, the distal retainer defining a channel (1514) in a portion thereof; and (d) a lockout assembly (1400) including a swing arm (1518) defining a sensor portion (1520) and a lockout portion (1540), the lockout portion defining an arm and a brake, the arm at least partially disposed within the channel of the distal retainer and being configured to pivot within the channel, the brake being configured to block distal translation of the knife in response to pivoting of the arm within the channel, the sensor portion projecting from a portion of the lockout portion and defining an engagement face configured to engage a portion of a staple cartridge disposed in the cartridge jaw to disengage the brake from the knife.

Example 34

The apparatus of Example 33, the distal retainer including a pivot post (1512), the arm of the lockout portion being pivotably secured to the pivot post.

Example 35

The apparatus of Examples 33 or 34, the arm being configured to pivot downwardly with respect to the distal retainer upon disengagement between the engagement face of the sensor portion and the staple cartridge.

Example 36

The apparatus of any of Examples 33 through 35, the engagement face of the sensor portion being configured to lay flat against a cartridge sled of the staple cartridge when engaging the portion of the staple cartridge.

The following clauses also relate to various non-exhaustive ways in which the teachings herein may be combined or applied.

1. An apparatus, comprising:
(a) a body;
(b) a shaft extending distally from the body;
(c) an end effector operatively coupled with the shaft, wherein the end effector includes:
(i) a cartridge jaw,
(ii) an anvil jaw configured to cooperate with the cartridge jaw to clamp and staple tissue,
(iii) a knife actuatable within the cartridge jaw and having a cutting edge configured to cut tissue, and
(iv) a distal retainer configured to couple the cartridge jaw to a portion of the shaft; and
(d) a lockout assembly including a sensor and a lockout, the lockout being vertically constrained, the sensor being associated with a first pivot and a second pivot, the first pivot being a fixed pivot grounded with respect to a channel, the second pivot being a moving pivot with respect to the lockout,
the lockout assembly having an unlocked position and a locked position, the second pivot being positioned above the first pivot when the lockout assembly is in the unlocked position with the lockout being configured to provide no interference with respect to actuation of the knife, the first pivot and the second pivot being positioned at substantially the same height when the lockout assembly is in the locked position.

2. The apparatus of clause 1, the knife defining a lock recess disposed between a proximal portion of a lower knife tab and a distal portion of the lower knife tab, the lockout being configured for receipt within the lock recess with the lockout assembly is in the locked position.

3. The apparatus of clause 2, the proximal portion of the lower knife tab defining an engagement face and a proximal ramp, the engagement face being configured to engage the lockout to prevent distal advancement of the knife.

4. The apparatus of clause 2, the proximal portion of the lower knife tab defining an engagement face and a proximal ramp, the distal portion of the lower knife tab defining a distal ramp, the engagement face being configured to engage the lockout to prevent distal advancement of the knife, the proximal ramp and the distal ramp being configured to engage the lockout to direct the lockout upwardly way from the lower knife tab.

5. The apparatus of clause 1, the channel being defined by a portion of the distal retainer.

6. The apparatus of clause 1, the distal retainer including a pivot post, the first pivot associated with the sensor being pivotably secured to the pivot post.

7. The apparatus of clause 1, the lockout assembly further including a bias, the bias being configured to bias the lockout assembly toward the locked position.

8. The apparatus of clause 7, the bias being a coil spring at least partially disposed within the channel.

9. The apparatus of clause 1, the sensor including an engagement portion and a manipulator, the engagement portion and the manipulator being disposed on opposite sides of the first pivot.

10. The apparatus of clause 9, the engagement portion being configured to engage a portion of a staple cartridge when the staple cartridge is disposed within the cartridge jaw.

11. The apparatus of clause 9, the engagement portion including one or more shaped portions being configured to permit engagement between the engagement portion and a portion of a staple cartridge when the staple cartridge is disposed within the cartridge jaw.

12. The apparatus of clause 9, the engagement portion including one or more shaped portions being configured to permit engagement between the engagement portion and a portion of a cartridge sled of a staple cartridge when the staple cartridge is disposed within the cartridge jaw.

13. The apparatus of clause 1, wherein the second pivot being a pivotable coupling between the lockout and the sensor.

14. The apparatus of clause 1, wherein the sensor is configured to engage a predetermined portion of the lockout to define the second pivot.

15. The apparatus of clause 1, wherein the sensor is laterally offset with respect to the lockout.

16. An apparatus, comprising:
(a) a body;
(b) a shaft extending distally from the body;
(c) an end effector operatively coupled with the shaft, wherein the end effector includes:
(i) a cartridge jaw,
(ii) an anvil jaw configured to cooperate with the cartridge jaw to clamp and staple tissue, (iii) a knife actuatable within the cartridge jaw and having a cutting edge configured to cut tissue, and (iv) a distal retainer configured to couple the cartridge jaw to a portion of the shaft; and (d) a lockout assembly including a sensor and a lockout, the sensor defining an engagement portion and a manipulator, a portion of the sensor being resiliently biased to bias the manipulator toward a predetermined position, the lockout including one or more arms and a brake disposed on a distal end of the one or more arms, the one or more arms being configured to pivot relative to the distal retainer to move the brake from a locked position in a distal advancement path of the knife to an unlocked position below the knife, the manipulator being in communication with the brake to bias the brake toward the locked position.

17. The apparatus of clause 16, the sensor further including a base, the engagement portion and the manipulator projecting from a portion of the base.

18. The apparatus of clause 17, the engagement portion and the manipulator being integral with the base.

19. The apparatus of clause 17, the base being secured to a portion of the cartridge jaw.

20. An apparatus, comprising:

(a) a body;

(b) a shaft extending distally from the body;

(c) an end effector operatively coupled with the shaft, wherein the end effector includes:

(i) a cartridge jaw, (ii) an anvil jaw configured to cooperate with the cartridge jaw to clamp and staple tissue, (iii) a knife actuatable within the cartridge jaw and having a cutting edge configured to cut tissue, and (iv) a distal retainer configured to couple the cartridge jaw to a portion of the shaft; and (d) a lockout assembly including a rod defining a sensor portion and a lockout portion, the sensor defining an engagement portion, the lockout portion extending downwardly with respect to the engagement portion, the engagement portion being configured to engage a portion of a staple cartridge disposed in the cartridge jaw to pivot the lockout portion with respect to the distal retainer to pivot the lockout portion from a locked position in a distal translation path of the knife to an unlocked position outside of the distal translation path of the knife.

IV. MISCELLANEOUS

It should be understood that any one or more of the teachings, expressions, versions, examples, etc. described herein may be combined with any one or more of the other teachings, expressions, versions, examples, etc. that are described herein. The above-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 18/650,562, entitled "Surgical Stapler with Firing Lockout Feature Coupled to End Effector Knife," filed Apr. 30, 2024; published as U.S. Pat. Pub. No. 2025/0331853 on Oct. 30, 2025 and/or U.S. patent application Ser. No. 18/650,653, entitled "Surgical Stapler with Firing Lockout Feature Coupled to End Effector Jaw," filed Apr. 30, 2024. published as U.S. Pat. Pub. No. 2025/0331854 on Oct. 30, 2025. The disclosure of each of the above patent references is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:

(a) a body;

(b) a shaft extending distally from the body;

(c) an end effector operatively coupled with the shaft, wherein the end effector includes:

(i) a cartridge jaw, (ii) an anvil jaw configured to cooperate with the cartridge jaw to clamp and staple tissue, (iii) a knife actuatable within the cartridge jaw and having a cutting edge configured to cut tissue, and (iv) a distal retainer configured to couple the cartridge jaw to a portion of the shaft; and (d) a lockout assembly including a sensor and a lockout, the lockout being vertically constrained, the sensor being associated with a first pivot and a second pivot, the first pivot being a fixed pivot grounded with respect to a channel, the second pivot being a moving pivot with respect to the lockout, the lockout assembly having an unlocked position and a locked position, the second pivot being positioned above the first pivot when the lockout assembly is in the unlocked position with the lockout being configured to provide no interference with respect to actuation of the knife, the first pivot and the second pivot being positioned at substantially the same height when the lockout assembly is in the locked position.

2. The apparatus of claim 1, the knife defining a lock recess disposed between a proximal portion of a lower knife tab and a distal portion of the lower knife tab, the lockout being configured for receipt within the lock recess with the lockout assembly is in the locked position.

3. The apparatus of claim 2, the proximal portion of the lower knife tab defining an engagement face and a proximal ramp, the engagement face being configured to engage the lockout to prevent distal advancement of the knife.

4. The apparatus of claim 2, the proximal portion of the lower knife tab defining an engagement face and a proximal ramp, the distal portion of the lower knife tab defining a distal ramp, the engagement face being configured to engage the lockout to prevent distal advancement of the knife, the proximal ramp and the distal ramp being configured to engage the lockout to direct the lockout upwardly way from the lower knife tab.

5. The apparatus of claim 1, the channel being defined by a portion of the distal retainer.

6. The apparatus of claim 1, the distal retainer including a pivot post, the first pivot associated with the sensor being pivotably secured to the pivot post.

7. The apparatus of claim 1, the lockout assembly further including a bias, the bias being configured to bias the lockout assembly toward the locked position.

8. The apparatus of claim 1, the bias being a coil spring at least partially disposed within the channel.

9. The apparatus of claim 1, the sensor including an engagement portion and a manipulator, the engagement portion and the manipulator being disposed on opposite sides of the first pivot.

10. The apparatus of claim 9, the engagement portion being configured to engage a portion of a staple cartridge when the staple cartridge is disposed within the cartridge jaw.

11. The apparatus of claim 9, the engagement portion including one or more shaped portions being configured to permit engagement between the engagement portion and a portion of a staple cartridge when the staple cartridge is disposed within the cartridge jaw.

12. The apparatus of claim 9, the engagement portion including one or more shaped portions being configured to permit engagement between the engagement portion and a portion of a cartridge sled of a staple cartridge when the staple cartridge is disposed within the cartridge jaw.

13. The apparatus of claim 1, wherein the second pivot being a pivotable coupling between the lockout and the sensor.

14. The apparatus of claim 1, wherein the sensor is configured to engage a predetermined portion of the lockout to define the second pivot.

15. The apparatus of claim 1 , wherein the sensor is laterally offset with respect to the lockout.

16. An apparatus, comprising:

(a) a body;

(b) a shaft extending distally from the body;

(c) an end effector operatively coupled with the shaft, wherein the end effector includes:

(i) a cartridge jaw, (ii) an anvil jaw configured to cooperate with the cartridge jaw to clamp and staple tissue, (iii) a knife actuatable within the cartridge jaw and having a cutting edge configured to cut tissue, and (iv) a distal retainer configured to couple the cartridge jaw to a portion of the shaft; and (d) a lockout assembly including a sensor and a lockout, the sensor defining an engagement portion and a manipulator, a portion of the sensor being resiliently biased to bias the manipulator toward a predetermined position, the lockout including one or more arms and a brake disposed on a distal end of the one or more arms, the one or more arms being configured to pivot relative to the distal retainer to move the brake from a locked position in a distal advancement path of the knife to an unlocked position below the knife, the manipulator being in communication with the brake to bias the brake toward the locked position.

17. The apparatus of claim 16, the sensor further including a base, the engagement portion and the manipulator projecting from a portion of the base.

18. The apparatus of claim 17, the engagement portion and the manipulator being integral with the base.

19. The apparatus of claim 17, the base being secured to a portion of the cartridge jaw.

20. An apparatus, comprising:

(a) a body;

(b) a shaft extending distally from the body;

(c) an end effector operatively coupled with the shaft, wherein the end effector includes:

(i) a cartridge jaw, (ii) an anvil jaw configured to cooperate with the cartridge jaw to clamp and staple tissue, (iii) a knife actuatable within the cartridge jaw and having a cutting edge configured to cut tissue, and (iv) a distal retainer configured to couple the cartridge jaw to a portion of the shaft; and (d) a lockout assembly including a rod defining a sensor portion and a lockout portion, the sensor portion defining an engagement portion, the lockout portion extending downwardly with respect to the engagement portion, the engagement portion being configured to engage a portion of a staple cartridge disposed in the cartridge jaw to pivot the lockout portion with respect to the distal retainer to pivot the lockout portion from a locked position in a distal translation path of the knife to an unlocked position outside of the distal translation path of the knife.

* * * * *